United States Patent [19]

Schwartz et al.

[11] Patent Number: 4,898,694

[45] Date of Patent: Feb. 6, 1990

[54] 17-HYDROXY-STEROIDS

[76] Inventors: Arthur G. Schwartz, 220 Locust St., Philadelphia, Pa. 19106; Marvin L. Lewbart, 546 E. Saint Andrews Dr., Media, Pa. 19063

[21] Appl. No.: 126,369

[22] Filed: Nov. 25, 1987

[51] Int. Cl.$^4$ ................................................. C07J 9/00
[52] U.S. Cl. .................................... 260/397.5; 540/94
[58] Field of Search .................. 260/397.5; 540/94; 514/172, 182

[56] References Cited

U.S. PATENT DOCUMENTS

| | | | |
|---|---|---|---|
| 2,232,735 | 2/1941 | Schoeller et al. | 260/397.5 |
| 2,243,887 | 6/1941 | Serini et al. | 260/397.5 |
| 2,266,778 | 12/1941 | Logemann et al. | 260/397.5 |
| 2,267,257 | 12/1941 | Ruzicka | 260/397.5 |
| 2,267,258 | 12/1941 | Ruzicka | 260/397.5 |
| 2,312,344 | 3/1943 | Logemann | 260/397.5 |
| 2,357,364 | 9/1944 | Stavely | 260/397.5 |
| 2,368,199 | 1/1945 | Butenandt et al. | 260/397.5 |
| 2,833,793 | 5/1958 | Dodson et al. . | |
| 2,838,500 | 6/1958 | Campbell et al. | 260/397.5 |
| 2,844,602 | 7/1958 | Ringold et al. | 260/397.5 |
| 2,911,418 | 11/1959 | Johns et al. . | |
| 2,927,119 | 3/1960 | Ellis et al. | 260/397.5 |
| 2,936,312 | 5/1960 | Babcock et al. | 260/397.5 |
| 2,969,379 | 1/1961 | Babcock et al. | 260/397.5 |
| 3,082,223 | 3/1963 | Bowers et al. | 260/397.5 |
| 3,148,198 | 9/1964 | Goldkamp . | |
| 3,176,030 | 3/1965 | Huffman | 260/397.5 |
| 3,187,023 | 6/1965 | Robinson | 260/397.5 |
| 3,189,624 | 6/1965 | Fried et al. | 260/397.5 |
| 3,200,113 | 8/1965 | Christiansen et al. | 260/397.5 |
| 3,254,099 | 5/1966 | Jolles et al. | 260/397.5 |
| 3,257,428 | 6/1966 | Klimstra | 260/397.5 |
| 3,282,969 | 11/1966 | Boswell, Jr. | 260/397.5 |
| 3,310,470 | 3/1967 | Schulze et al. | 514/182 |
| 3,357,888 | 12/1967 | Campbell et al. | 514/182 |
| 3,380,886 | 4/1968 | Campbell et al. | 514/182 |
| 3,391,166 | 7/1968 | Klimstra | 260/397.5 |
| 3,463,798 | 8/1969 | Godtfredsen et al. | 260/397.5 |
| 3,471,480 | 10/1969 | Fritsch et al. . | |
| 3,501,504 | 3/1970 | Klimstra | 260/397.5 |
| 3,505,364 | 4/1970 | Mehrhof et al. | 260/397.5 |
| 3,716,530 | 2/1973 | Krubiner | 260/397.5 |
| 3,976,691 | 8/1976 | Middleton et al. . | |
| 4,344,941 | 8/1982 | Weichert et al. | 514/172 |
| 4,628,052 | 12/1986 | Peat et al. . | |

FOREIGN PATENT DOCUMENTS

| | | | |
|---|---|---|---|
| 0909205 | 9/1972 | Canada | 260/397.5 |
| 133995 | 3/1985 | European Pat. Off. . | |
| 210665 | 2/1987 | European Pat. Off. . | |
| 0198704 | 7/1938 | Fed. Rep. of Germany | 260/397.5 |
| 1064058 | 8/1959 | Fed. Rep. of Germany | 260/397.5 |
| 1084720 | 7/1960 | Fed. Rep. of Germany | 260/397.5 |
| 1239306 | 4/1964 | Fed. Rep. of Germany . | |
| 2035738 | 6/1970 | Fed. Rep. of Germany . | |
| 2705917 | 2/1977 | Fed. Rep. of Germany . | |
| 1261864 | of 1961 | France | 260/397.5 |
| 1327004 | of 1963 | France | 260/397.5 |

(List continued on next page.)

OTHER PUBLICATIONS

Chang et al., "The Anabolic and Androgenic Activities of 17-alpha-methytestosterone and Related Steroids in Castrated Rats and Mice", Chem. Absts., 62:4295h, (1965).

(List continued on next page.)

Primary Examiner—H. M. S. Sneed
Assistant Examiner—J. Saba
Attorney, Agent, or Firm—Scully, Scott, Murphy & Presser

[57] ABSTRACT

Compounds of the formulae:

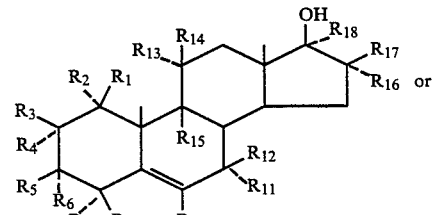

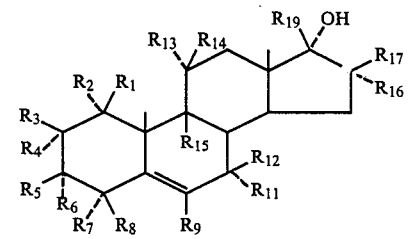

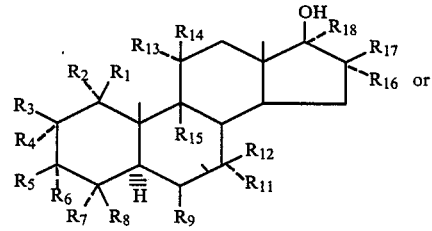

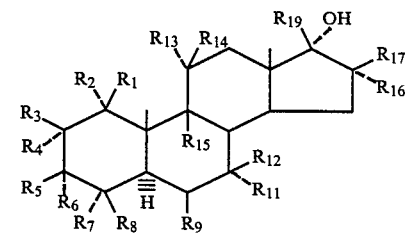

are useful as anti-cancer, anti-obesity, anti-diabetic, anti-coronary agents, anti-aging agents, anti-hypolipidemic agents and anti-autoimmune agents.

101 Claims, No Drawings

FOREIGN PATENT DOCUMENTS

| | | | |
|---|---|---|---|
| 2317934 | 2/1977 | France . | |
| 7104485 | 10/1971 | Netherlands | 260/397.5 |
| 0390910 | 8/1965 | Switzerland | 260/397.5 |
| 989503 | 8/1963 | United Kingdom . | |
| 1087920 | 10/1967 | United Kingdom | 260/397.5 |

OTHER PUBLICATIONS

Bernassau et al., "Circular Dichroism of Olefins. IV. A Semiquantititative Paredictaion of the Intensity of the Cotton Effect of Allyl Alcohols and Ethers", Chem. Absts., 92:181401.

Beloeil et al., "Stereochemistry of Gaseous Anions: OH-Negative Chemical Ionization of 17-R-5-Alpha, 14-Beta-Androstant-14,17-Diol", J. Am. Chem. Soc., 105:1355-1359, (1983).

Martin Bohl, "Molecular Mechanics Investigation on Side-Chain Conformations of a 17-Alpha-ethyl-1-7-Beta-Hydroxy Steroid with Regard to Receptor Binding", Chem. Absts., 107:33341, (1987).

Hanson et al., *Perkin Transactions I*, (1977), pp. 499–501.

Chemical Abstracts, 89, 1058656, (1978).

Numazawa et al., *Steroids*, 32, 519–527, (1978).

Abou-Gharbia et al., *Journal of Pharmaceutical Sciences*, 70, 1154, (1981).

Pashko et al., *Carcinogenesis*, 2, 717–721, (1981).

Pashko et al., *Carcinogenesis*, 5, 463–466, (1984).

Raineri and Levy, *Biochemistry*, 9, 2233, (1970).

Robinson et al., *J. Org. Chem.*, 28, 975, (1963).

Neef et al., *J. of Org. Chem.*, 43, 4679–4680, (1978).

Gordon et al., *Cancer Research*, 46, 3389–3395, (1986).

Julian et al., in *JACS*, 70, 3872–3876, (1948).

Ross et al., in *J. Chem. Soc.*, 25, (1945).

Denny et al., *J.C.S. Perkin I*, 486–492.

Shoppe et al., *J. Chem. Soc. C*, 2767, 2770, (1969).

Kirk, *J.C.S. Perkin I*, 787, (1980).

Numazawa et al., *Steroids*, 385, 403, (1985).

17-HYDROXY-STEROIDS

BACKGROUND OF THE INVENTION

This invention relates to novel steroids and more particularly to androsterone derivatives useful as anti-cancer, anti-obesity, anti-diabetic, and hypolipidemic agents and useful for combatting coronary diseases.

Dehydroepiandrosterone (DHEA) and DHEA-sulfate are major adrenal secretory products in humans. The plasma concentration of DHEA-sulfate, which next to cholesterol, is the most abundant steroid in humans, undergoes the most marked age-related decline of any known steroid.

Although DHEA-sulfate is the main precursor of placental estrogen and may be converted into active androgens in peripheral tissue, there is no obvious biological role for either DHEA or DHEA-sulfate in the normal individual. Several retrospective and prospective studies suggest that women with sub-normal levels of these steroids may be predisposed to develop breast cancer. For example, see Brownsey, et al., "Plasma dehydroepiandrosterone sulfate levels in patients with benign and malignant breast disease," Eur. J. Cancer, 8, 131-137 (1972); Bulbrook, et al., "Relation between urinary androgen and corticoid excretion and subsequent breast cancer," Lancet, 2, 395-398 (1971); Rose, et al., "Plasma dehydroepiandrosterone sulfate, androstenedione and cortisol, and urinary free cortisol excretion in breast cancer," Eur. J. Cancer, 13, 43-47 (1977); Wang, et al., "Studies of the sulfate esters of dehydroepiandorsterone and androsterone in the blood of women with breast cancer," Eur. J. Cancer, 10, 477-482 (1974); and Zumoff, et al., "Abnormal 24-hr mean plasma concentrations of dehydroisoandrosterone and dehydroisoandrosterone sulfate in women with primary operable breast cancer," Cancer Research, 41, 3360-3363, September, 1981.

It has also been established that DHEA is a potent non-competitive inhibitor of mammalian glucose-6-phosphate dehydrogenase (G6PDH). For example, see Oertel, et al., "The effects of steroids on glucose-6-phosphate dehydrogenase," J. Steroid Biochem., 3, 493-496 (1972) and Marks, et al., "Inhibition of mammalian glucose-6-phosphate dehydrogenase by steroids," Proc. Nat'l Acad. Sci, USA, 46, 477-452 (1960). Moreover, Yen, et al., "Prevention of obesity in A$^{vy}$/a mice by dehydroepiandrosterone," Lipids, 12, 409-413 (1977), reported that long-term administration of DHEA to VY-A$^{vy}$/a mice prevented the development of obesity without suppressing appetite.

Furthermore, it is also known that the long-term treatment of C3H mice with DHEA, in addition to reducing weight gain without suppressing appetite, markedly inhibits spontaneous breast cancer development and may delay the rate of aging. It has been observed that DHEA antagonizes the capacity of the tumor promoter, 12-0-tetradecanoylphorbol-13-acetate, to stimulate $^3$H-thymidine incorporation in mouse epidermis and in a cultured rat kidney epithelial cell line. See, Schwartz, "Inhibition of spontaneous breast cancer formation in female C3H-A$^{vy}$/a mice by long-term treatment with dehydroepiandrosterone, Cancer Res., 39, 1129-1132 (1979); and Schwartz, et al., "Dehydroepiandrosterone: an anti-obesity and anti-carcinogenic agent," Nut. Cancer 3, 46-53 (1981).

Ben-David, et al., "Anti-hypercholesterolemic effect of dehydroepiandrosterone in rats," Proc. Soc. Expt. Biol. Med., 125, 1136-1140 (1967) have observed that DHEA treatment has an anti-hypercholesterolemic effect in mice, while Coleman, et al. (Diabetes 31, 830, 1982) report that administration of DHEA produces a marked hypoglycemic effect in C57BL/KsJ-db/db mice. The latter authors suggest that the therapeutic effect of DHEA might result from its metabolism to estrogens.

It is further known that DHEA and 16α-bromoepiandrosterone are inhibitors of Epstein-Barr virus-induced transformation of human lymphocytes and that 16α-bromoepiandrosterone is a more potent inhibitor of mammalian G6PDH than DHEA. See, Schwartz, et al. Carcinogenis, Vol. 2 No. 7, 683-686 (1981).

While DHEA has been found effective in the afore-described manners, there is however, evidence of an estrogenic effect after prolonged administration. DHEA is not an estrogen per se but is well known to be convertible into estrogens. In addition, the therapeutic dose of DHEA is rather high. It would therefore be highly desirable to provide steroids, which while having the same afore-described advantage of DHEA are more potent and do not produce an estrogenic effect.

Besides DHEA, other steroids are known in the art.

Great Britain Pat. No. 989,503 to Burn, et al. discloses 6,16β-dimethyl-3β-hydroxyandrost-5-en-17-ones.
These compounds are disclosed to be useful as possessing pituitary inhibiting action.

U.S. Pat. No. 2,833,793 to Dodson, et al. discloses 1β,3β-dihydroxy-5-androsten-17-one as an androgenic and anabolic agent.

U.S. Pat. No. 2,911,418 to Johns, et al. discloses 16α-chloro-3β-hydroxyandrost-5-en-17-one and 3β-hydroxy-16α-iodoandrost-5-en-17-one as an anti-androgen.

Goldkamp, et al. in U.S. Pat. No. 3,148,198 disclose that 16α,16β-difluoro-3β-hydroxyandrost-5-en-17-one possess androgenic properties.

French application No. FR-A 2,317,934 discloses the following compounds:
3β-hydroxy-16ξ-methylandrost-5-en-17-one
3β-hydroxy-16ξ-ethylandrost-5-en-17-one
3β-hydroxy-16ξ-isopropylandrost-5-en-17-one U.S. Pat. No. 3,976,691 discloses the following compounds:

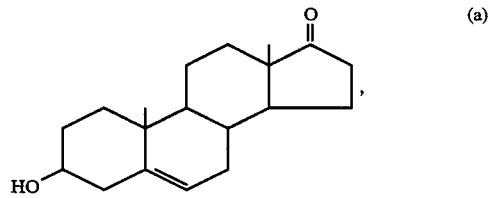

(a)

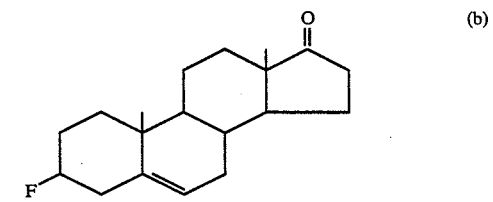

(b)

U.S. Pat. No. 3,471,480 to Fritsch, et al. discloses the following compounds which are useful as progestational agents:
(a) 3β-iodo-Δ$^5$-6-methyl-17-oxoandrostene (b) 3β-chloro-Δ⁵-6-methyl-17-oxoandrostene
(c) 3β-hydroxy-Δ⁵-6-methyl-17-oxoandrostene Hanson, et al. in *Perkin Transactions I*, 1977, pp. 499-501, disclose 3β,4β-dihydroxyandrost-5-en-17-one. No utility is disclosed.

Chemical Abstract 89:105866b discloses that 3β-hydroxy-5α-androstan-17-one can be hydroxylated in the 15α-position. Furthermore, said reference teaches that hydroxylation of 3β-hydroxy-5α-androsten-17-one gave both the 7α and 7β-hydroxyisoandrosterones.

Numazawa, et al. in *Steroids*, 32, 519-527 disclose 3β,16α-dihydroxyandrost-5-en-17-one. No utility is disclosed.

German Pat. No. 2,035,738 discloses 7α-Methyl-3β-hydroxy-5-androsten-17-one and 6,7α-dimethyl-3β-hydroxy-5-androsten-17-one.

German Pat. No. 2 705917 discloses 3β,16β-dihydroxy-5-androsten-17-one.

The Annual Report of the Fels Research Institute, pp. 32-33, (1979-1980) discloses the following compounds as having tumor-preventive, anti-obesity and anti-aging qualities:

3β-hydroxy-16α-bromo-5α-androstan-17-one
3β-hydroxy-16α-chloro-5α-androstan-17-one
3β-hydroxy-16α-fluoro-5α-androstan-17-one
3β-hydroxy-16α-iodo-5α-androstan-17-one
3β-hydroxy-16α-bromoandrost-5-ene-17-one
16α-bromoandrostan-17-one Abou-Gharbia, et al. in *Journal of Pharmaceutical Sciences*, 70, 1154-1156 (1981) disclose the syntheses of:
3β-hydroxy-16α-chloro-5α-androstan-17-one,
3β-hydroxy-16α-fluoro-5α-androstan-17-one,
3β-hydroxy-16α-bromo-5α-androstan-17-one,
3β-hydroxy-16α-iodo-5α-androstan-17-one.

Pashko, et al. in *Carcinogenesis*, 2, 717-721 (1981) disclose that 16α-Br-epiandrosterone is more active than DHEA in inhibiting G6PDH and in reducing the rate of [³H] thymidine incorporation into mouse breast epithileum and epidermis. The authors suggest that this compound may be useful in suppressing breast cancer development.

Neef, et al. in *Journal of Org. Chem.*, 43, 4679-4680 disclose the syntheses of 3β-hydroxy-16α-methyl-5-androsten-17-one and 3β-hydroxy-16β-methyl-5-androsten-17-one.

Robinson, et al. in *Journal of Org. Chem.*, 28, 975-980 (1963) disclose the synthesis of 3β-hydroxy-16α, 16β-difluoro-5-androsten-17-one; 16-formyl-5-androstene-3β-ol-17-one; 16,16-Difluoro-17-α-methyl-5-androstene-3β,17β-diol; 16,16-difluoro-4-androsten-17β-ol-3-one; 16,16-difluoro-17α-ethynyl-5-androsten-3β,17β-diol; 16,16-difluoro-17α-methyl-4-androsten-17β-ol-3-one; 16,16-difluoro-17α-ethynyl-4-androsten-17β-ol-3-one and 16,16-Difluoro-17α-vinylandrost-4-en-17β-ol-3-one.

Raineri, et al. in *Biochemistry*, 9, 2233-2243 (1970) tested the inhibitory activity of the following steroids on NADP and NAD linked activity of glucose 6-phosphate dehydrogenase:

5α-Androstane-3β,17β-diol
3β-hydroxy-5α-androstan-17-one
3β-hydroxy-5α-androstan-16-one
3β-hydroxy-5β-androstan-17-one
3α-hydroxy-5α-androstan-17-one
11β-hydroxy-5α-androstan-17-one
3α-hydroxy-4α-methyl-5α-androstan-17-one
3α-hydroxy-7α-methyl-5α-androstan-17-one
3β-hydroxy-7α-methyl-5-androsten-17-one
3β-hydroxy-16α-bromo-5α-androstan-17-one
3β-hydroxy-5β-pregnan-20-one
3β-hydroxy-5α-pregnen-20-one
3β,17α-dihydroxy-5α-pregnan-20-one
3β,21-dihydroxy-5-pregnen-20-one
3β-hydroxy-6-methyl-5-pregnen-20-one
3β-hydroxy-16α-bromo-5-pregnen-20-one Gordon, et al. in *Cancer Research* 46, 3389-3395 (1986) disclose that DHEA, 16α-bromoepiandrosterone, epiandrosterone, 3β-hydroxy-5α-pregnan-20-one, 5α-androstan-17-one and 5α-androstan-3β,16α-diol-17-one are inhibitors of glucose 6-phosphate dehydrogenase. Furthermore, said reference discloses that testosterone, 17β-Estradiol, 5-androstene-3β,17β-diol, testosterone, dehydroepiandrosterone-3-sulfate and 5α-androstan-17β-ol are noninhibitors of glucose-6-phosphate dehydrogenase. The reference suggests that there is a general correlation between the structure requirements for blocking differentiation to adipocytes and inhibiting glucose-6-phosphate dehydrogenase.

Julian, et al. in *JACS*, 70, 3872-3876 (1948) disclose the preparation of 16-dimethylaminomethyldehydroisoandrosterone, 16-methylenedehydroisoandrosterone acetate and 16-methyltestosterone.

Ross, et al. in *J. Chem. Soc.*, 25, (1945) disclose the synthesis of 16-isopropylidene-5-androstene-17-one. Peat in U.S. Pat. No. 4,628,052 disclose compositions containing the following compounds as the active ingredient:

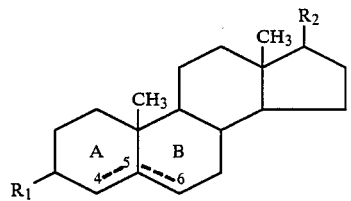

Wherein R₁ is O or OH and R₂ is O, or OH; and which may contain one double bond in ring A and/or ring B or tocopherol;

The compounds are alleged to be useful in treating rheumatoid-arthritis, osteoarthritis and arthritis associated with psoriasis and with lupus and other autoimmune diseases and also for treating non-specific joint pain associated with stress.

SUMMARY OF THE INVENTION

The present invention relates to novel steroids which are useful as cancer-preventive agents, anti-obesity agents, anti-hyperglycemic agents, anti-aging agents, and anti-hypercholesterolemic agents and which are useful at combatting autoimmune diseases.

Moreover, the present invention is directed to novel steroids useful as anti-cancer, anti-obesity, anti- Finally, the present invention is directed to the process for the treatment and/or prevention of cancer, obesity, aging, diabetes and hyperlipidemia.

Therefore, the present invention provides novel steroids of the general formulae:

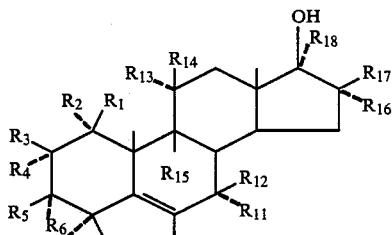

or

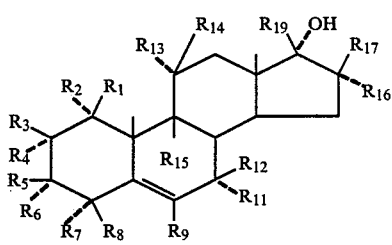

wherein $R_1, R_2, R_3, R_4, R_5, R_6, R_7, R_8, R_{11}, R_{12}, R_{13}, R_{14}, R_{15}, R_{16}$ and $R_{17}$ are each independently hydrogen, lower alkyl, halogen, hydroxy or lower alkoxy;

$R_9$ is hydrogen, lower alkyl or halogen; and $R_{18}$ and $R_{19}$ are each independently hydrogen, lower alkyl, lower alkenyl, lower alkynyl, formyl, lower alkanoyl or epoxy, with the proviso that when $R_{18}$ or $R_{19}$, whichever is present, is ethynyl or methyl, $R_{16}$ and $R_{17}$ are both fluoro and $R_1, R_2, R_3, R_4, R_6, R_7, R_8, R_9, R_{10}, R_{11}, R_{12}, R_{13}, R_{14}$ and $R_{15}$ are hydrogen, then $R_5$ is other than hydroxy; and with the further proviso that when $R_1, R_2, R_3, R_4, R_6, R_7, R_8, R_9, R_{10}, R_{11}, R_{12}, R_{13}, R_{14}, R_{15}, R_{16}, R_{17}$ and $R_{18}$ are all hydrogen, then $R_5$ is other than hydroxy.

Further objectives are accomplished herein by providing novel steroids of the formulae:

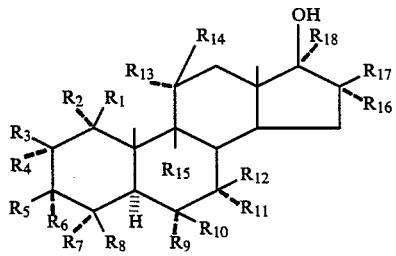

or

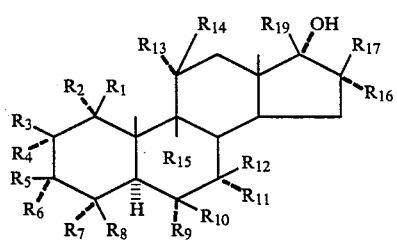

wherein $R_1, R_2, R_3, R_4, R_5, R_6, R_7, R_8, R_{11}, R_{12}, R_{13}, R_{14}$ and $R_{15}$ are each independently hydrogen, lower alkyl, halogen, hydroxy or lower alkoxy;

$R_9$ and $R_{10}$ are independently hydrogen, lower alkyl or halogen; and $R_{18}$ and $R_{19}$ are each independently hydrogen, lower alkyl, lower alkenyl, lower alkynyl, formyl, lower alkanoyl or epoxy, with the proviso that when $R_1$–$R_{17}$ are all hydrogen, then $R_{18}$ or $R_{19}$, whichever is present, is other than hydrogen and with the further proviso that when $R_1, R_2, R_3, R_4, R_6, R_7, R_8, R_9, R_{10}, R_{11}, R_{12}, R_{13}, R_{14}, R_{15}, R_{16}$ and $R_{17}$ are all hydrogen, and either $R_{18}$ or $R_{19}$, whichever is present is hydrogen or

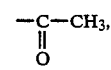

then $R_5$ is other than hydroxy.

The present invention is also directed to processes for the treatment and/or prophylaxis of cancer, obesity, aging, diabetes and hyperlipidemia and autoimmune diseases, such as lupus erthematosus or Coomb's positive hemolytic anemia, comprising administering to a host, e.g., mammals, a therapeutically effective amount of the afore-identified steroids.

More particularly, the steroids of the present invention have the general formulae:

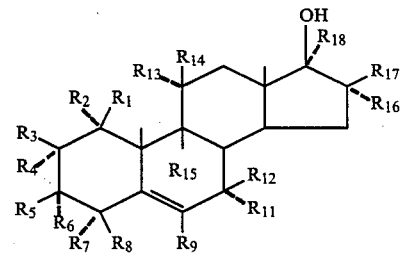

or

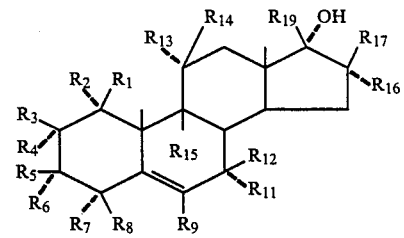

or

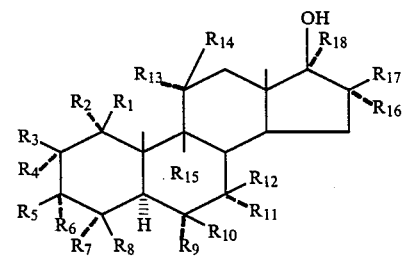

or

-continued

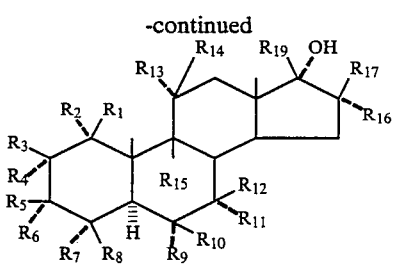

wherein $R_1$–$R_{19}$ are as defined hereinbefore. The $R_1$–$R_{15}$ substituents are designated as being in the α-position by means of a broken line (—) joining the substituent to the steroid nucleus, the substituents are designated as being in the β-position by means of a solid line (—) joining the substituent to the steroid nucleus and in those cases in which the substituent may be either in the α- or β- position the substituents are indicated as being joined to the steroid nucleus by a wavy line. Furthermore, in accordance with I.U.P.A.C. nomenclature, the carbon atoms of the steroids of the present invention are numbered as follows and the steroids have the designated I.U.P.A.C. stereochemistry:

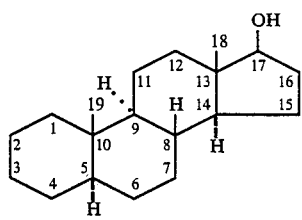

In accordance with the present invention, it has been surprisingly discovered that steroids having a certain structure, described hereinabove and hereinafter in more detail, are characterized with significant pharmacological properties without toxic or undesirable estrogenic effects. That is, it has been quite unexpectedly discovered that the steroids of the present invention are useful as cancer preventive, anti-obesity, anti-diabetic, anti-aging, anti-autoimmune and anti-hypercholesterolemic agents, but unlike DHEA are more potent and exhibit very little or no estrogenic effect. Furthermore, unlike DHEA, compounds of the present invention do not induce liver enlargement and increased catalase activity.

In the present invention, the alkyl groups are preferably lower alkyl, which may be straight or branched chain, and which contain up to 6 carbon atoms. Examples include methyl, ethyl, propyl, isopropyl, butyl, isobutyl, pentyl, amyl and the like. A preferred alkyl group contains 1-3 carbons. The most preferred alkyl group is methyl.

The alkoxy groups are preferably lower alkoxy, which may be straight or branched chain and which contain up to 6 carbon atoms. Examples include methoxy, ethoxy, propoxy, isopropoxy, butoxy, isobutoxy, pentoxy and the like. An especially preferred alkoxy group contains 1-3 carbons. The most preferred alkoxy group is methoxy.

The halo atoms are preferably Br, F or Cl, especially F.

Moreover, it is preferred that at most one of the other substituents, $R_1$, $R_2$, $R_3$, $R_4$, $R_7$, $R_8$, $R_9$, $R_{11}$, $R_{12}$, $R_{13}$, $R_{14}$, or $R_{15}$, or $R_{10}$, whenever present, are other than hydrogen. In the most preferred embodiment $R_1$, $R_2$, $R_3$, $R_4$, $R_7$, $R_8$, $R_9$, $R_{11}$, $R_{12}$, $R_{13}$, $R_{14}$, $R_{15}$ or $R_{10}$, whenever present, are hydrogen.

Preferred substituents for $R_{16}$ and $R_{17}$ include hydrogen, halogen, especially fluorine, and lower alkyl, especially methyl.

It is preferred that $R_{18}$ and $R_{19}$ are independently hydrogen, methyl, ethyl, ethenyl, ethynyl, formyl, acetyl or epoxy.

Preferred $R_5$ and $R_6$ are hydrogen and lower alkyl. It is especially preferred that $R_6$ is hydrogen and $R_5$ is hydrogen or lower alkyl. The preferred lower alkyl is methyl.

Additional variations in the structural formula representing the instant compounds can be effected without significantly altering the therapeutic properties. For example, the alkyl moieties can be substituted by one or more of a variety of substituents, such as hydroxy, halogen, alkyl and the like.

The preferred embodiments of the compounds of Formulae I and II have the formula:

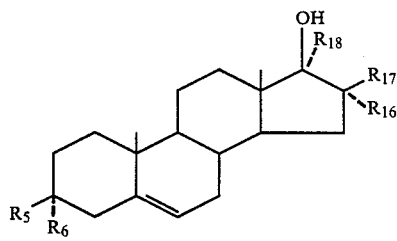

V or

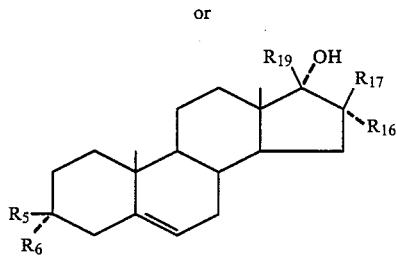

VI wherein
$R_5$ and $R_6$ are independently hydrogen or lower alkyl; and
$R_{16}$ and $R_{17}$ are each independently hydrogen, lower alkyl, halogen, hydroxy or lower alkoxy; and
$R_{18}$ and $R_{19}$ are each independently hydrogen, lower alkyl, lower alkenyl, lower alkynyl, formyl, lower alkanoyl or epoxy, Especially preferred compounds of Formula V have the formula:

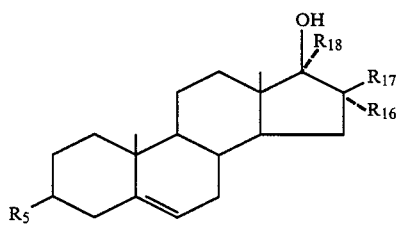

VII wherein $R_5$, $R_{16}$, $R_{17}$ and $R_{18}$ have the same definition as in Formula V.

Especially preferred compounds of Formula VI have the formula:

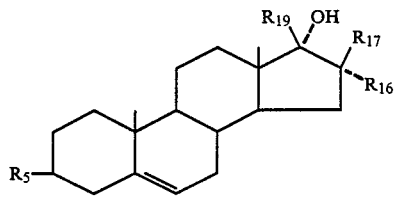

wherein $R_5$, $R_{16}$, $R_{17}$ and $R_{19}$ have the same definitions as in Formula VI.

The preferred embodiments of the compounds of Formulae III and IV have the formulae:

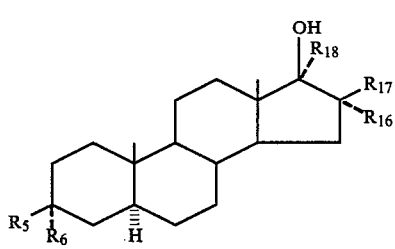

or

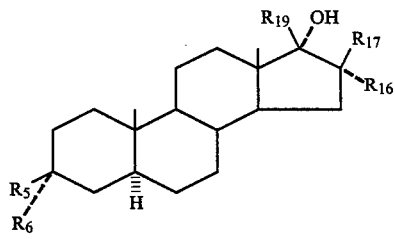

wherein $R_5$ and $R_6$ are independently hydrogen or lower alkyl;

$R_{16}$ and $R_{17}$ are each independently hydrogen, lower alkyl, halogen, hydroxy or lower alkoxy; and $R_{18}$ and $R_{19}$ are each independently hydrogen, lower alkyl, lower alkenyl, lower alkynyl, formyl, lower alkanoyl or epoxy, with the proviso that when $R_1$–$R_{17}$ are hydrogen, then $R_{18}$ is other than hydrogen.

Especially preferred compounds of Formula IX have the formula:

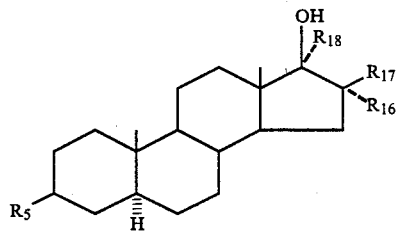

wherein $R_5$, $R_{16}$, $R_{17}$ and $R_{18}$ have the same definition as that in Formula IX.

Especially preferred compounds of Formula X have the formula:

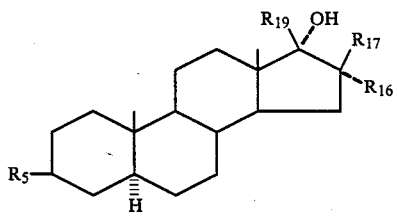

wherein $R_5$, $R_{16}$, $R_{17}$ and $R_{19}$ have the same definitions as that in Formula X.

The procedures described hereinbelow are representative of the processes for preparing compounds of the present invention. Furthermore, the procedures described hereinbelow are also applicable to those steroids which have additional substituents than those depicted hereinbelow. If substituents on the steroidal ring are themselves reactive under the reaction conditions then these substituents can themselves be protected according to chemical techniques known in the art may be employed. Examples of many of these possible groups may be found in "Protective Groups in Organic Synthesis," by J. W. Green, John Wiley and Sons, 1981.

If more than one substituent is to be added to the steroidal ring, the substituents can be added in any order, except it is preferred that halogens are added last.

Finally, the procedures described hereinbelow are applicable to all the steroids of the present invention, regardless of whether a double bond is present in the 5,6 position of the steroidal ring. Moreover, the steroids of Formula III and IV can be prepared from the corresponding steroids of Formula I and II by techniques known to one skilled in the art, e.g., by catalytic hydrogenation using, e.g, $H_2$/Pd, $H_2$/Pt or $H_2$/Ni.

The steroids of the present invention may be prepared in accordance with conventional organic synthesis from known compounds or readily preparable intermediates.

An exemplary general procedure for the synthesis of 17-hydroxy androstenes and androstanes is as follows:

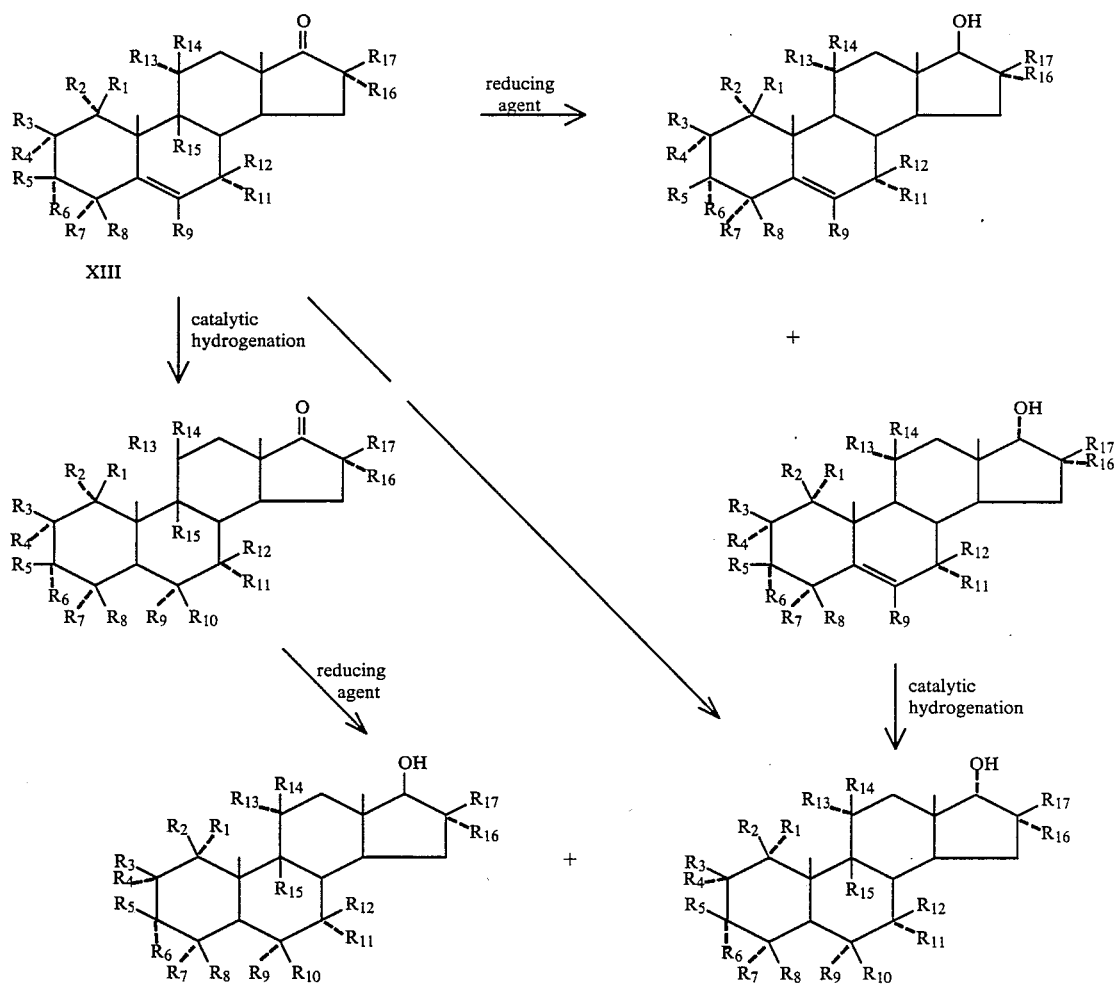

wherein $R_1$–$R_9$ and $R_{11}$–$R_{17}$ are as defined herein and $R_{10}$ is hydrogen.

As shown by the reactions in Scheme I the 17-hydroxy compounds are prepared by reducing the carbonyl

group at C-17. The catalyst that is used depends upon the product desired. For example, if 5-androstene-17-ol is the desired product, then the catalyst system should selectively reduce the carbonyl group at C-17 at a faster rate than the double bond in position C-5-C-6, so that the reaction can be terminated before the catalyst reduces the olefin functionality. There are a number of reducing agents which can reduce ketones faster than olefins. The most commonly used are the metal hydrides, such as lithium aluminum hydride, sodium borohydride, LiAlH$_3^-$, diisobutylaluminum hydride, LiBH(sec-Bu)$_3$, LiAlH(OMe)$_3$ and the like. The reductions should be run in suitable solvents, which dissolve the reactants, but is inert to both reactants and products. When using aluminum hydrides such as LiAlH$_4$, common solvents include ether and tetrahydrofuran dioxanes. On the other hand, when NaBH$_4$ is the reducing agent, the reaction can take place in tetrahydrofurans, dioxanes, ethers, as well as water or alcoholic solvents. For example, sodium borohydride in ethanol as well as NaBH$_4$ and LiCl in diglyme selectively reduce the keto group without affecting the olefinic functionality. Other reducing agents include BH$_3$CN$^-$ in HMPT, isopropyl alcohol and aluminum isopropoxide (Meerwein-Pondorf-Verley reagent) and the like. It is preferable that these reactions are run at temperatures ranging about room temperature to about $-50°$ C. These reagents are commonly used in organic synthesis and one skilled in the art can readily determine the reaction conditions necessary for the reductions.

On the other hand, when preparing 5-androstane-17-ols from 5-androstane-17-ones, the reducing agents discussed hereinabove can be used. In addition, other reducing agents, such as catalytic hydrogenation, i.e., hydrogen over platinum, nickel, palladium, ruthenium; bis 3-methyl-2-butylborane (disiamylborane) in THF, BH$_3$-THF; and NaBH$_4$+BF$_3$ diglyme, and the like can be used. This latter group of reducing agents are also capable of reducing both the carbonyl groups and the alkene functionality of 5-androstene-17-one, thereby forming the 5-androstane-17-ol directly.

If R$_{18}$ or R$_{19}$ is other than hydrogen, then said group can be added to the steroidal ring concomitant with C-17 carbonyl reduction to hydroxy. Organometallic reagents, such as Grignard reagents, and other reagents containing active metals, such as alkyl lithiums, alkyl copper and the like can effect such transformation as shown in the exemplary Scheme II:

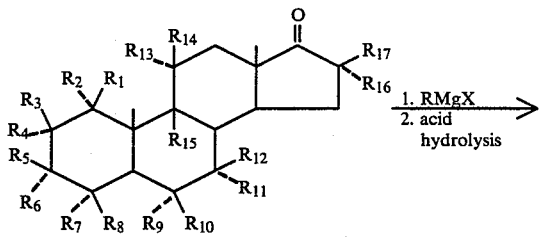

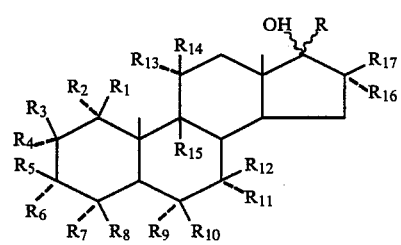

wherein $R_1$–$R_{17}$ are as defined hereinabove, except none are hydroxy, R is as defined hereinabove and $R_{18}$ and X are halide.

The reaction is run in a solvent that will dissolve both reactants and is inert to both reactants and products. Solvents include, but are not limited to, ethers, tetrahydrofurans, dioxane, and the like. The reaction can safely take place at temperatures ranging from −100° C. to room temperature but it is preferred that temperatures below 0° C. be employed.

The second step, the hydrolysis step, not only quenches the Grignard reagent, but also yields the 17-hydroxy compound from the intermediate formed from the reaction of the ketone and the Grignard. The hydrolysis step is usually carried out by the addition of dilute acid, such as hydrochloric acid or sulfuric acid. Additionally, an aqueous solution of ammonium chloride can be used.

For the addition of acetylenic groups, a Group IA metal, such as sodium or lithium may be used. Vinylalanes prepared and used in accordance with the procedure by Newman, *Tetrahedral Letters,* 1971, 4571, can be used for the addition of vinyl groups. Alternatively, the alkenyl derivative can be prepared by catalytic reduction of the alkyne substituent prepared hereinabove.

The aldehyde functionality can be prepared as follows:

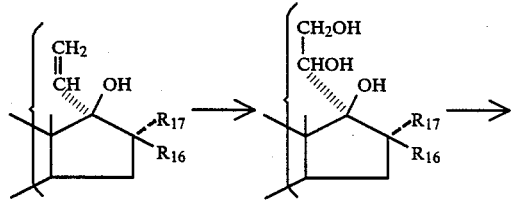

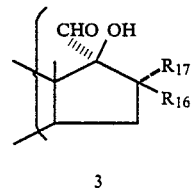

These diagrams only focus on the D ring of the molecules. It is to be understood that the A, B, C rings are attached and contain the substituents $R_1$–$R_{15}$ as indicated hereinabove. The 17α-ethynyl-17-β-ol derivative is prepared as described hereinabove. Said compound is reacted with a syn-hydroxylation agent, such as osmium tetroxide or alkaline potassium permanganate to afford a triol (2). Oxidative cleavage of the intermediate with periodic acid or lead tetraacetate produces the 17α-ol-17β-ol (3).

The 17β-ol-17α-ol can be prepared by the following method:

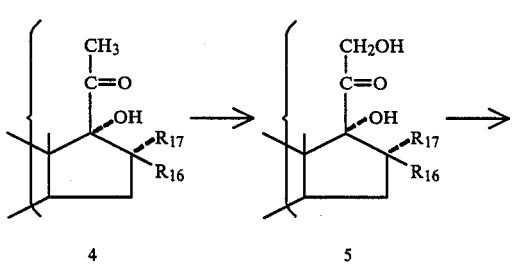

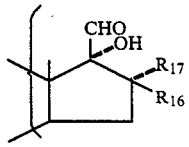

Sequential bromination, acetoxylation and deacetoxylation of the 17α-ol-17β-alkylcarbonyl such as 17α-hydroxy-17β-methylcarbonyl (4) produces the α-ketol (5). Reduction thereof with sodium borohydride followed by oxidative cleavage with periodic acid or lead tetraacetate, affords the desired product (6).

The α-epoxy-β-ol and β-epoxy-α-ol derivatives can be prepared as follows:

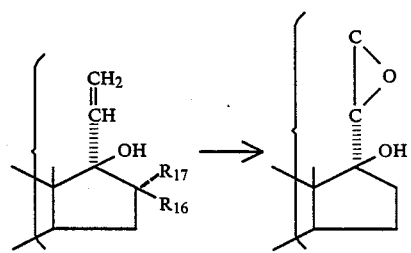

The 17α-ethynyl-17-β-ol derivative prepared in accordance with the procedures described herein is reacted with a peracid, such as m-chlorobenzoic acid to afford 8.

The β-epoxy-α-ol derivative can be prepared by the following method:

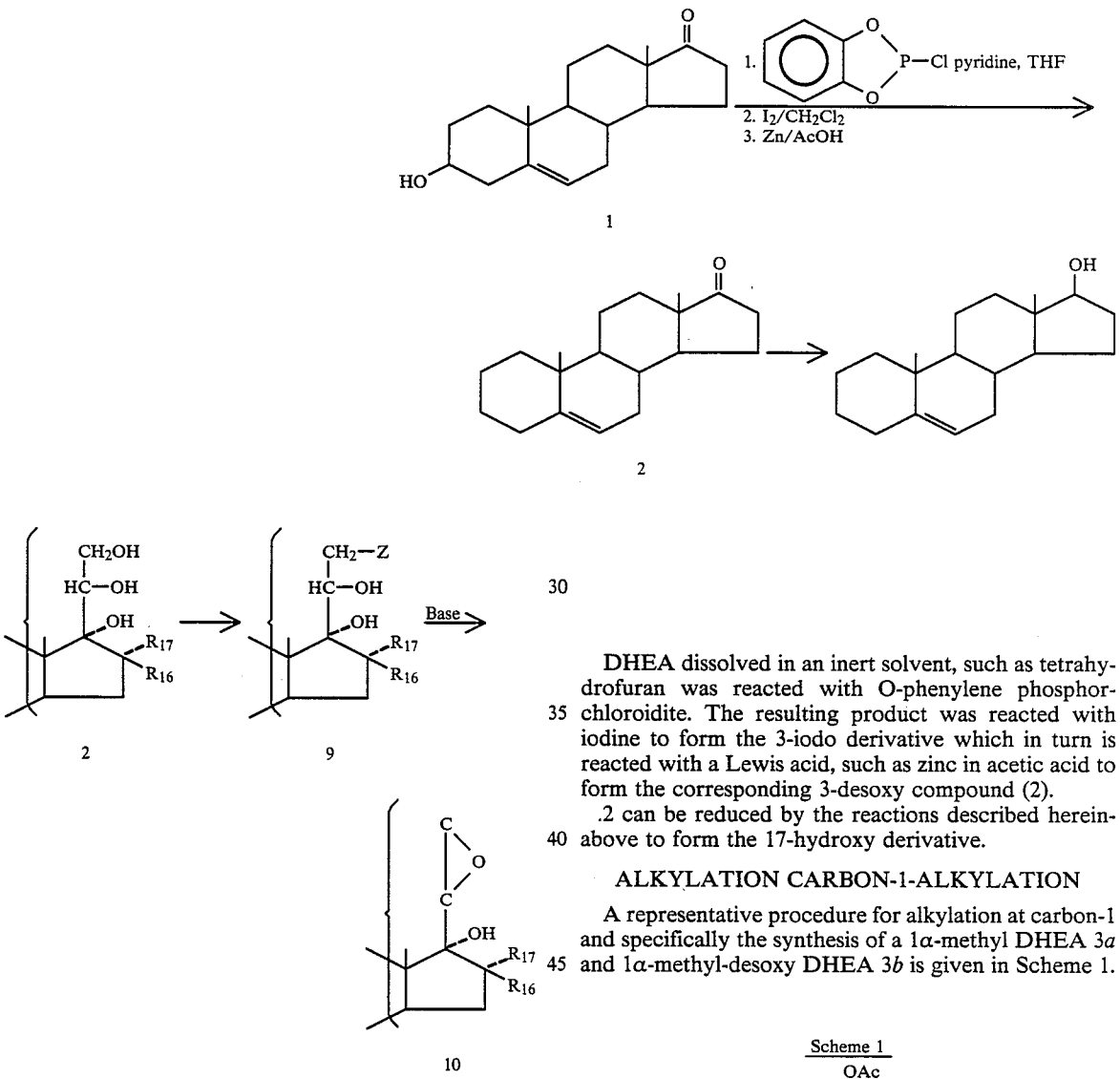

wherein Z is a good leaving group.

The glycerol 2 was prepared in accordance with the procedure described hereinabove. The hydroxy group on the β-carbon is converted to a good leaving group, such as tosylate or mesylate or halide, e.g., chlorides or bromides. Alkaline treatment of 9 affords the 20-21-epoxide (10).

When any one of the groups $R_1$–$R_{17}$ is hydroxy, then the hydroxy group can be protected according to chemical techniques known in the art. A variety of protecting groups known in the art may be employed. Examples of many of these possible groups may be found in "Protectice Groups in Organic Synthesis," by J. W. Green, John Wiley and Sons, 1981. For example, the hydroxy group can be converted to its methyl ether.

The starting materials in the syntheses described hereinabove can be prepared by using the appropriate procedures exemplified hereinbelow.

Preparation of 3-Desoxy Compounds

The 3-desoxy compounds are prepared from the corresponding 3-hydroxy compounds by techniques known in the art. For example, DHEA dissolved in an inert solvent, such as tetrahydrofuran was reacted with O-phenylene phosphorchloroidite. The resulting product was reacted with iodine to form the 3-iodo derivative which in turn is reacted with a Lewis acid, such as zinc in acetic acid to form the corresponding 3-desoxy compound (2).

.2 can be reduced by the reactions described hereinabove to form the 17-hydroxy derivative.

ALKYLATION CARBON-1-ALKYLATION

A representative procedure for alkylation at carbon-1 and specifically the synthesis of a 1α-methyl DHEA 3a and 1α-methyl-desoxy DHEA 3b is given in Scheme 1.

Scheme 1

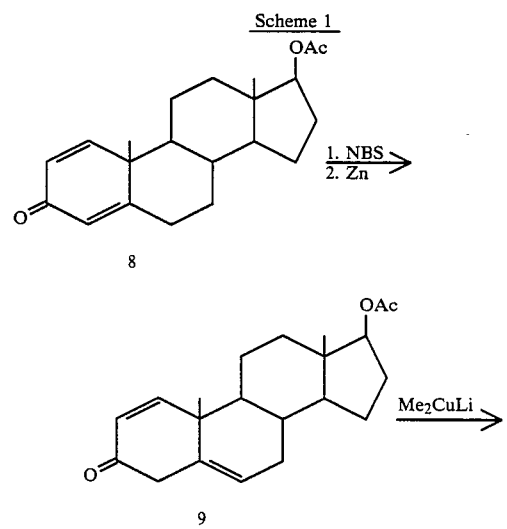

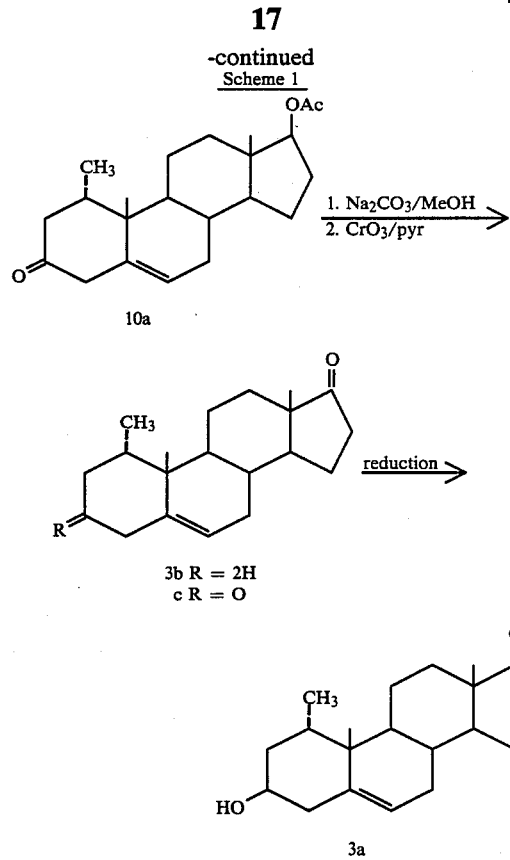

dium borohydride in 95% ethanol yielded 2α-methyl-3β,17β-dihydroxy-5-androsten-17-acetate (5). Protection of the 3-hydroxy group as a tetrahydropyranyl ether followed by hydrolysis of the 17-acetate yielded 2α-methyl-3β,17β-dihydroxy-5-androsten-3-tetrahydropyranyl ether 7. Oxidation of the C-17 hydroxy group in 7 followed by hydrolysis of the tetrahydropyranyl ether with hydrochloric acid and aqueous acetone yielded 3β-hydroxy-2α-methylandrost-5-en-17-one (9).

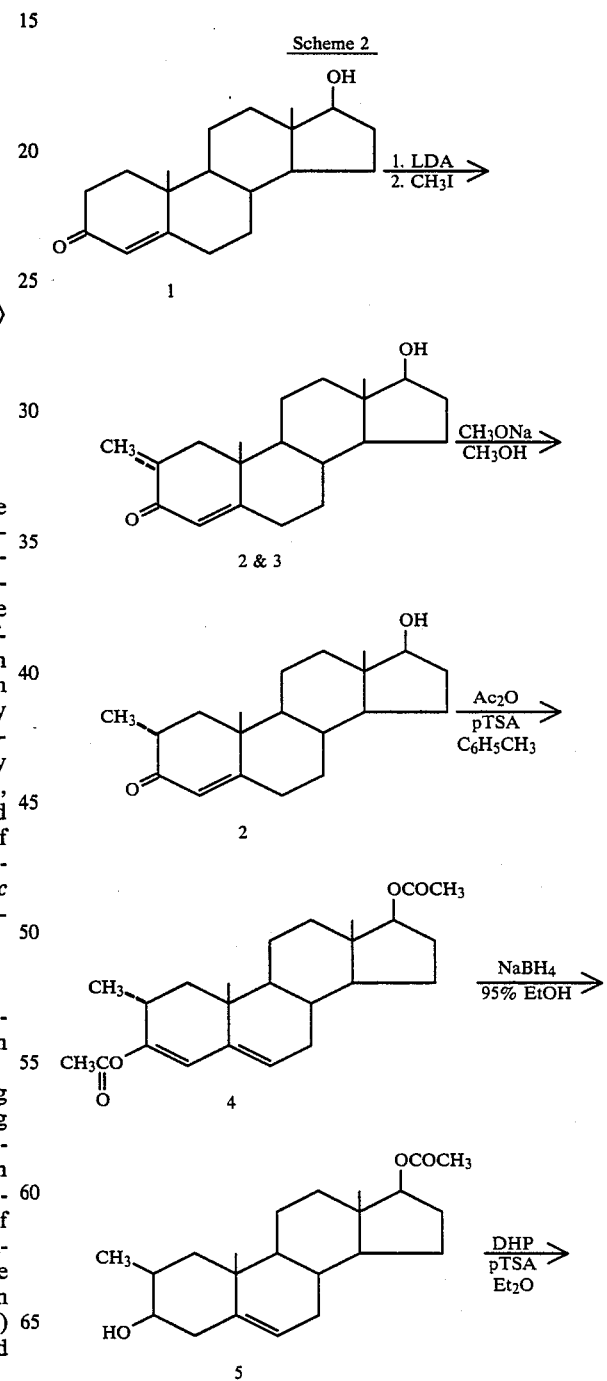

Allylic bromination (e.g. with N-bromosuccinimide (NBS)) of 17β-acetoxyandrosta-1,4-dien-3-one 8 followed by treatment with zinc affords the non-conjugated enone 9. 1,4-Alkylation with lithiodimethyl cuprate provides the 1α-methyl ketone 10a. At this stage the 10a may be converted to a methylene by Wolff-Kishner reduction or the Huang Minlon modification thereof. These vigorous reaction conditions result in hydrolysis of the resulting carbon-17 acetate thereby yielding the hydroxy desoxy derivative, 17β-hydroxy-1α-methylandrost-5-ene (3b). Both 10a and its desoxy derivative can be converted via standard reactions, i.e., hydrolysis of the 17-acetate with sodium carbonate and methanol followed by chromium trioxide oxidation of the resulting 17-alcohol to the carbon-17 ketone. Selective reduction of the carbon-3 ketone, 3,17-diketone 3c using sodium borohydride pyridine (pyr) yields 1α-methyl dehydroepiandrosterone 3a.

CARBON-2-ALKYLATIONS

The following procedures are illustrative for alkylation at carbon-2 and are figuratively illustrated in Scheme 2 below.

Alkylation of testosterone (I) with an alkylating agent, such as methyl iodide, in the presence of a strong base, such as t-BuOK, sodium t-pentoxide, lithium diisopropylamide (LDA), Na NH₂, Et₂Ni, n-butyl lithium and the like gives a mixture of the 2α- and 2β-alkyl-17-β-hydroxy-4-androsten-3-one (2 and 3). Treatment of the mixture with a strong base, such as sodium methoxide in methanol, epimerizes the 2β-axial alkyl to the 2-α-equitorial configuration (2). Acetylation of 2 with an acetylating agent, such as acetic anhydride (Ac₂O) and p-toluenesulfonic acid (p-TSA) in toluene afforded 2α-methyl-3,17β-dihydroxy-3,5-androstadien-3,17-diacetate (4). Treatment of the diacetate (4) with so-

19
-continued
Scheme 2

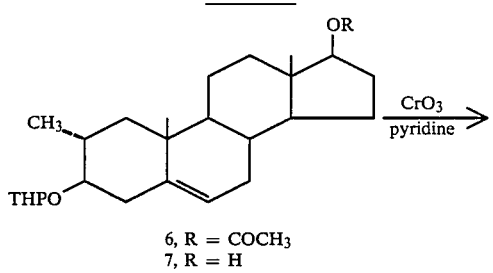

6, R = COCH₃
7, R = H

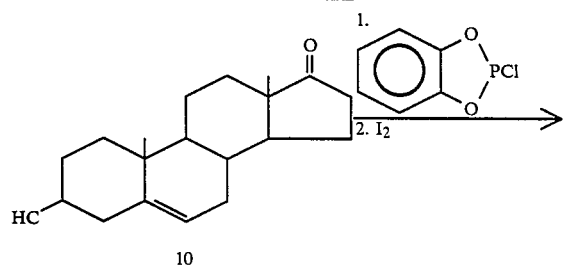

20
-continued
SCHEME 3

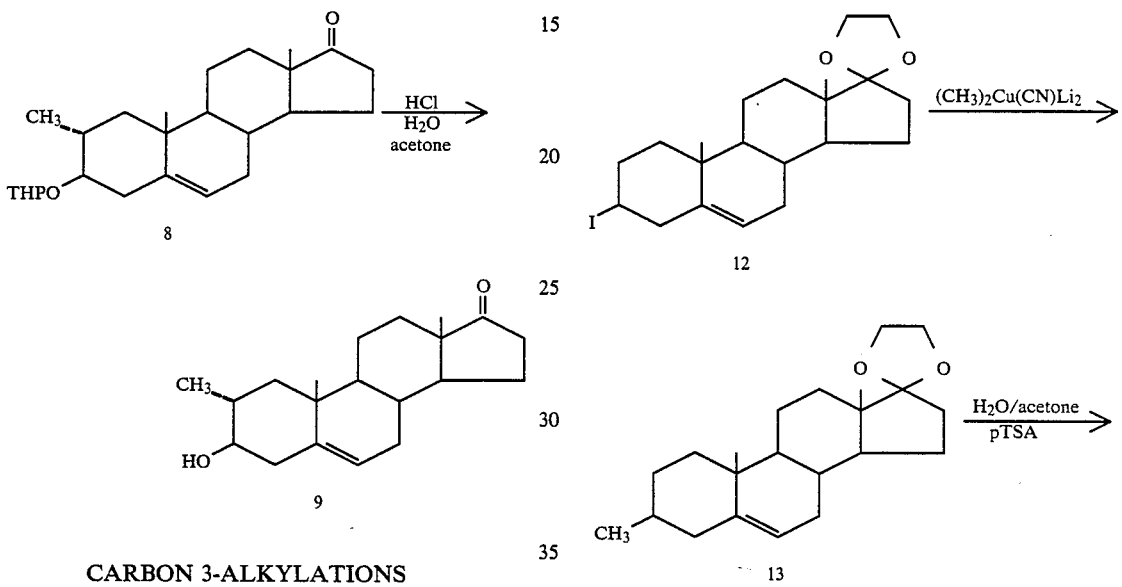

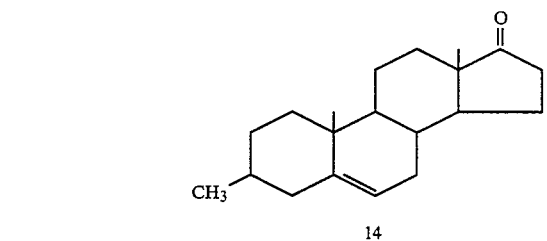

Similarly, by using 3α-Hydroxyandrost-5-en-17-one, the 3α-methylandrost-5-en-17-one was prepared.

CARBON 3-ALKYLATIONS

The schematic for carbon 3-alkylations are shown figuratively in scheme 3 below.

Synthesis of dehydroepiandrosterone with a methyl group replacing the hydroxyl group at carbon-3 is shown below in scheme 3. The methyl configuration at carbon-3 is β, as determined by X-ray analysis. 3β-Hydroxy-5-androst-en-17-one (10) was iodinated at carbon-3 with O-phenylenephosphorochloridite followed by decomposition of the resulting phosphite ester with iodine. 3β-Iodoandrost-5-en-17-one (11) was ketalized, then alkylated with a mixture of methyl lithium and cuprous cyanide in tetrahydrofuran to yield 3β-methylandrost-5-en-17-ethylene ketal (13). Hydrolysis of the ketal afforded 3β-methylandrost-5-en-17-one (14).

ALKYLATION AT CARBON-4

A procedure for carbon-4 alkylation and the synthesis of 4α-methyl DHEA is given in Scheme 4.

SCHEME 3

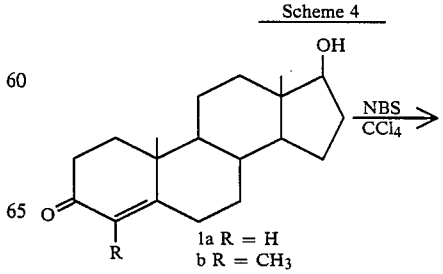

1a R = H
b R = CH₃

-continued
Scheme 4

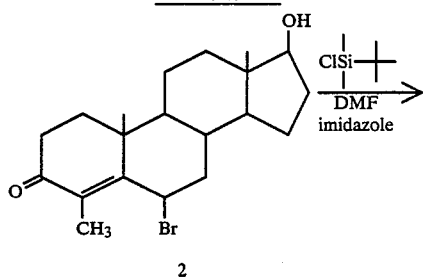
2

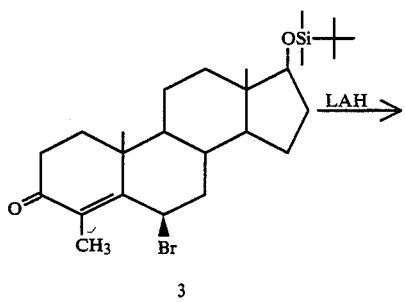
3

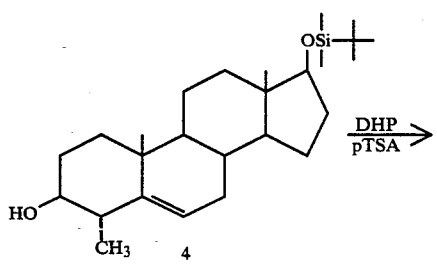
4

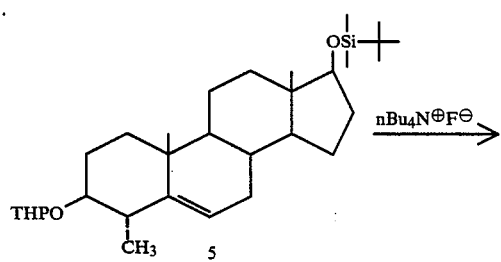
5

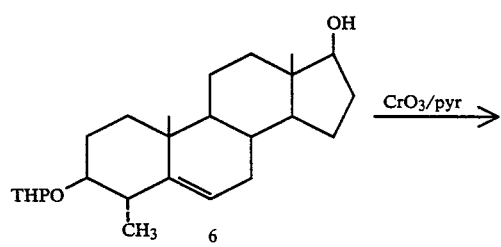
6

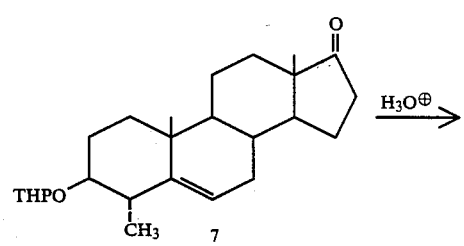
7

-continued
Scheme 4

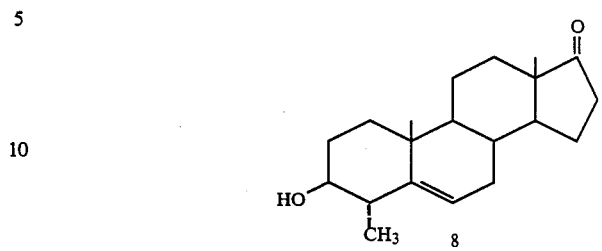
8

With reference to Scheme 4, alkylation of testesterone 1a using potassium t-butoxide and methyl iodide yielded 4-methyltestosterone 1b. Allylic bromination of 4-methyltestosterone using N-bromosuccinimide in carbon tetrachloride yields the 6β-bromo-4-methylandrost-4-en-17β-ol-3-one 2. Protection of the C-17 alcohol as its t-butyldimethyl silyl derivative yields 3. Lithium aluminum hydride reduction of the ketone in 3 with concomitant double bond migration and loss of bromide should yield 4. Protection of the C-3 alcohol as a tetrahydropyranyl ether, followed by deprotection and oxidation of the C-17 alcohol should yield the C-17 ketone 7. Removal of the C-3 tetrahydropyranyl ether yields 4α-methyl dehydroepiandrosterone 8.

ALKYLATION AT CARBON-6

Steroids may be alkylated at carbon-6 using the method of U. Stache and W. Fritsch, Liebigs Analen 1966, 697, 204.

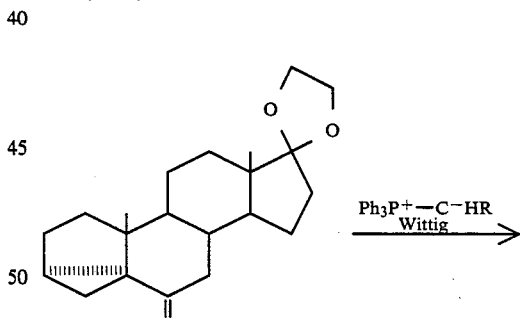
1

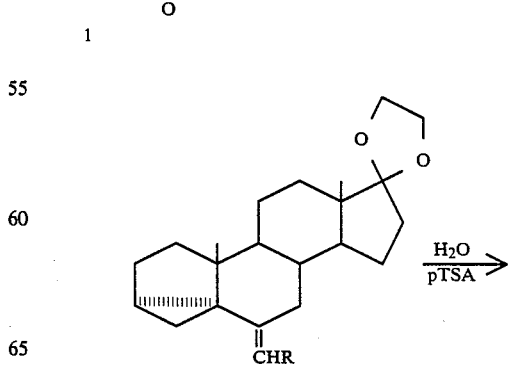
2

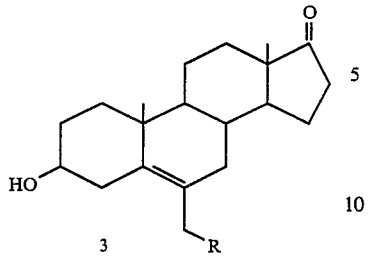

3α,5-Cyclosteroids such as 3α,5-cyclo-5α-androstan-6,17-dione 17 ketal 1 are readily available by solvolysis of steroidal 5-ene-3β-tosylates and mesylates followed by oxidation of the C-6 hydroxyl group. Methylenation of 1 affords 6-methylene-3α,5-cyclo-5α-androstan-17-one 17-ketal 2 (R=H). Treatment of 2 with aqueous acid results in the addition of water and the formation of 3β-hydroxy-6-methylandrost-5-en-17-one, 3 (R=H). Alkenylated derivatives of 3 may be synthesized starting with the appropriated substituted Wittig reagent, such as $Ph_3P^{\oplus}$—$CH^{\ominus}$—$CH=CH_2$.

Alkylation at C-7

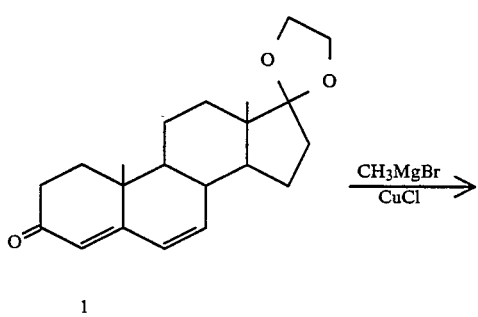

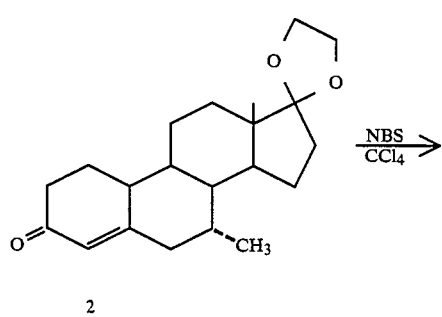

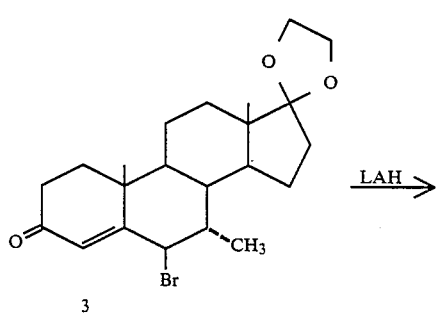

Alkylation at C-7

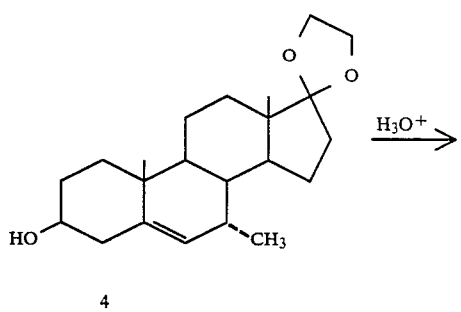

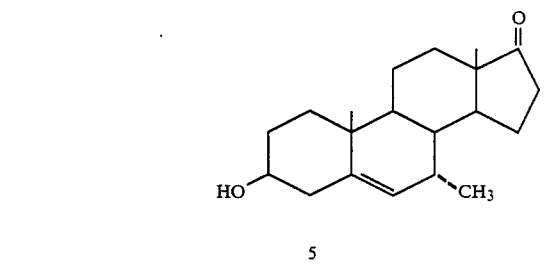

Alkylation of androsta-4,6-dien-3,17-dione 17 ketal 1 with methyl magnesium bromide in the presence of cuprous chloride, proceeds via conjugate addition to yield 7α-methylandrost-5-en-3,17-dione 17 ketal 2. Allylic bromination of 2 using N-bromosuccinimide in carbon tetrachloride yields the 6β-bromo-7α-methylandrost-4-en-3,17-dione 17 ketal 3. Lithium aluminum hydride reduction of the ketone in 3 with concomitant double bond migration and loss of bromide should yield 4. Deprotection of the C-17 ketone with aqueous acid yields 3β-hydroxy-7α-methylandrost-5-en-17-one, 5. Higher homologues may be synthesized using the substituted Grignard reagent i.e. R=CH₃, C₂H₅, C₃H₇. The 7β-epimer can be synthesized by treatment of 2 with DDQ--dichlorodicyanoquinone to generate another olefin at C-7. Catalytic reduction of this olefin should occur from the α face of the steroid to yield the 7β-methyl steroid i.e. 7β-methylandrost-5-en-3,17-dione 17 ketal. Following the same sequence as above yields 3β-hydroxy-7β-methylandrost-5-en-17-one.

Alkylation at Carbon-11

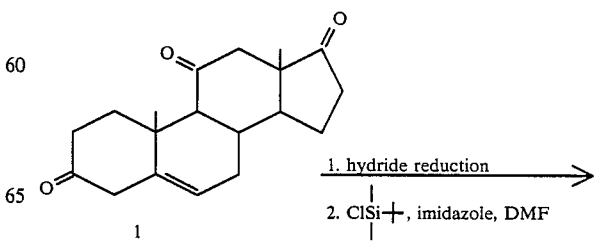

Alkylation at Carbon-11

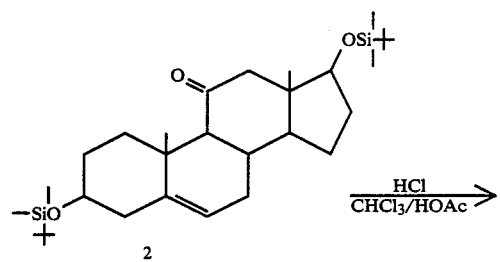

2

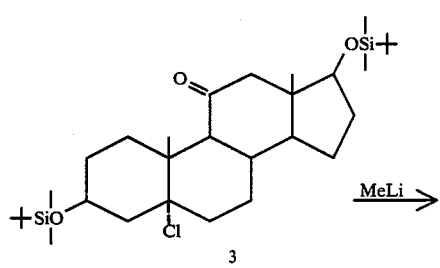

3

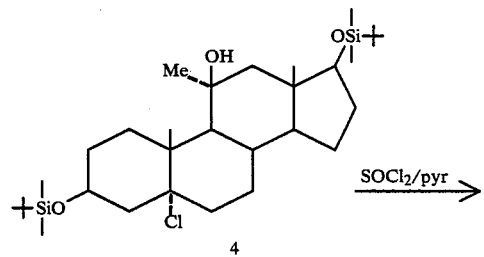

4

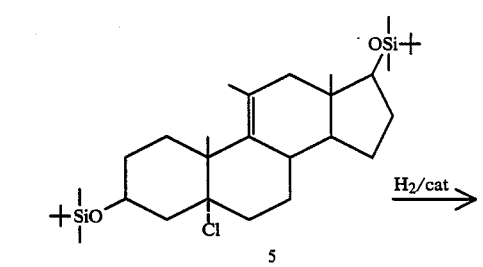

5

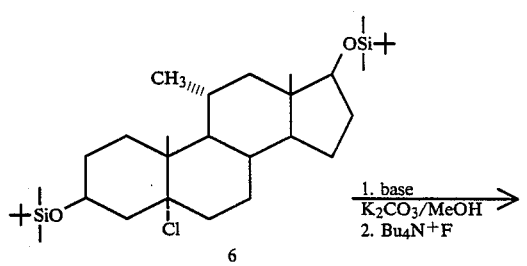

6

-continued
Alkylation at Carbon-11

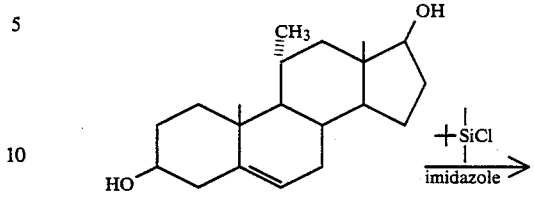

7

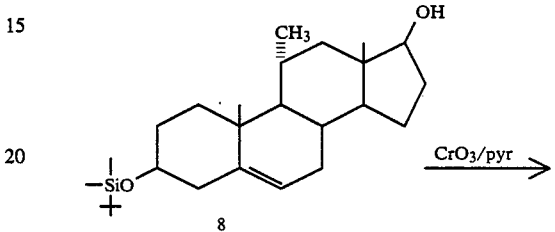

8

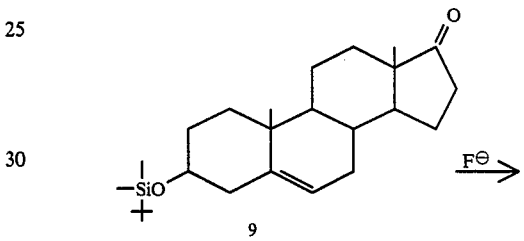

9

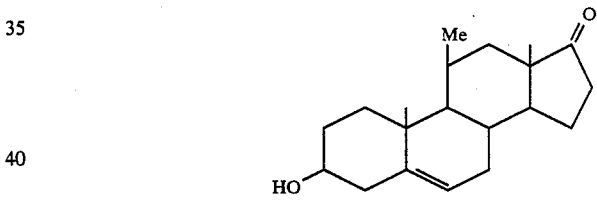

10

Due to the hindered nature of the C-11 ketone, selective reduction of androst-5-en-3,11,17-trione 1 with hydride should yield the C-3, C-17 dihydroxy steroid 2a, R=H which is protected as its bis(dimethyl-tert-butylsilyl)ether 2b R=Si(CH$_3$)$_2$t-Bu. Addition of hydrogen chloride across the C-5 olefin affords 5α-chloro-3β,17β-dihydroxyandrost-5-en-11-one 3,17-bis(dimethyl-t-butylsilyl) ether 3. Alkylation with methyl lithium proceeds from the less hindered α face to yield 5α-chloro-11α-methylandrostan-3β,11β,17β-triol-3,17-bis(dimethyl-t-butylsilyl) ether 4. Dehydration of the methylcarbinol 4 with thionyl chloride in pyridine provides the olefin 5. Catalytic hydrogenation of 5 gives the saturated 11α-methyl-5αchloro-bis (silyl) ether 6. Treatment of the chloro silyl ether 6 with base followed by tetrabutyl ammonium fluoride affords 11α-methylandrost-5-en-3β,17β-diol 7. Selective silylation yields 11α-methylandrost-5-en-3β,17β-diol 3-dimethyl t-butylsilyl ether 8. Oxidation of the C-17 alcohol in 8 yields 9 and deprotection of the 3-alcohol yields 11α-methylandrost-5-en-3β-ol-17-one 10. (11α-methyl DHEA).

Alkylation at Carbon-16

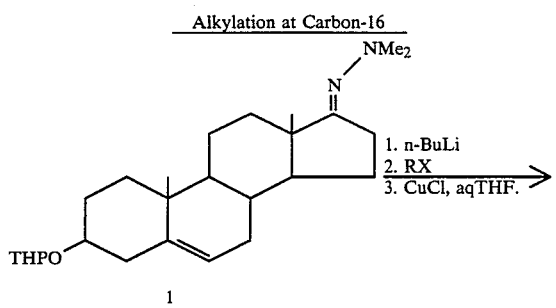

The following procedure is illustrative for the preparation of 16-methyl derivatives of 3β-methyl-5-androsten-17-ones.

As shown supra, 3β-methyl-5-androsten-17-one 2 was prepared from DHEA (1).

Treatment of 2 with lithium diisopropylamide in tetrahydrofuran at −78° C. generated an enolate which was smoothly alkylated with excess methyl iodide to afford 3β,16α-dimethylandrost-5-en-17-one 3, along with small amounts of the 16β-methyl and 16,16-dimethyl derivatives 4 and 5, respectively.

SCHEME

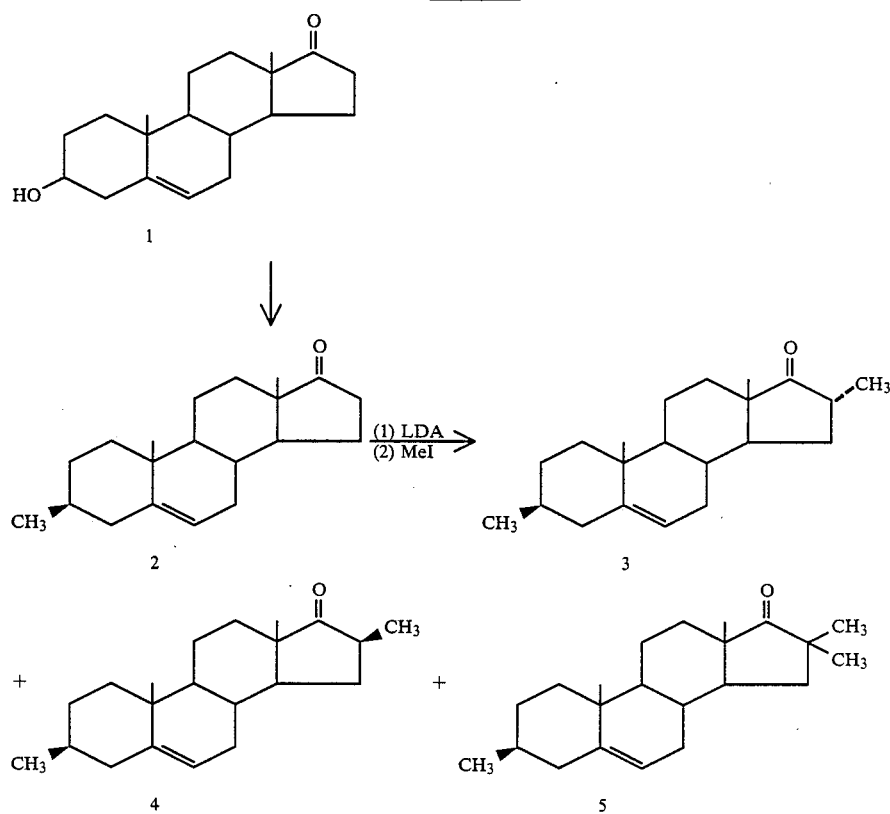

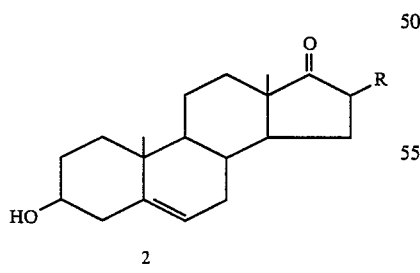

Alkylation of the 17-ketodimethylhydrazone of DHEA 3-tetrahydropyranyl ether using n-butyl lithium as the base followed by an alkyl halide RX, afforded the 16α-alkylated steroid. Hydrazone cleavage with cuprous chloride in aqueous tetrahydrofuran led to regeneration of the C-17 ketone and concomitant cleavage of the tetrahydropyranyl ether resulting in the 16α-alkyl-3β-hydroxy-androst-5-en-17-one 2.

The following procedures illustrate hydroxylation at Carbon-1, 2, 4, 7, 11 or 16.

C-1 HYDROXYLATION

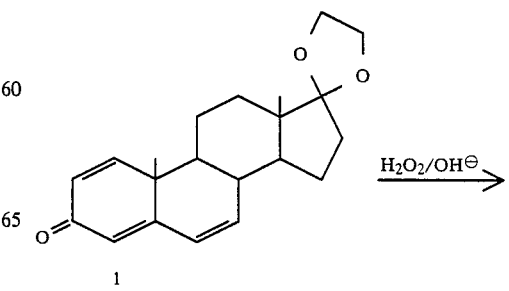

-continued
C-1 HYDROXYLATION

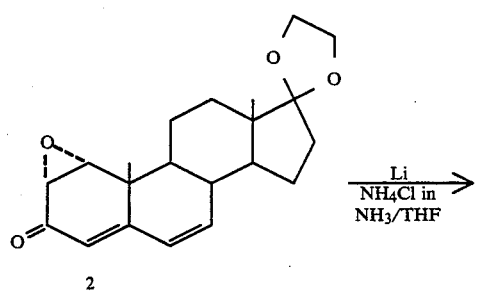

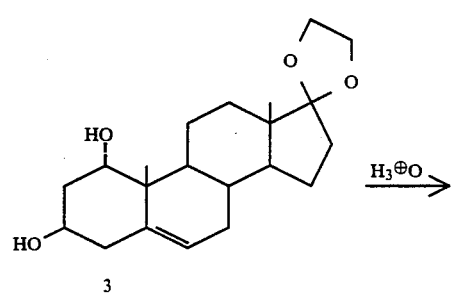

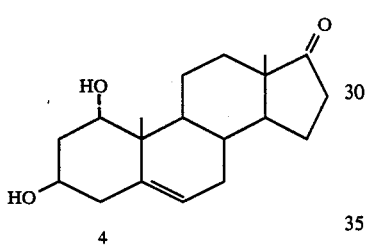

Alkaline hydrogen peroxide epoxidation of androsta-1,4,6-triene-3,17-dione 17-ketal 1 with basic hydrogen peroxide yields the 1α,2α-epoxide 2. Treatment of 1α,-2α-epoxyandrosta-4,6-dien-3,17-dione 17-ketal 2 with a large excess each of lithium metal and ammonium chloride in ammonia-tetrahydrofuran (1:1) under reflux leads to 1α,3β-dihydroxyandrost-5-en-17-one 17-ketal 3. Hydrolysis of the ketal affords 1α,3β-dihydroxyandrost-5-en-17-one, 4. Also, fermentation of DHEA with *penicillium aspergillus* affords 4, i.e. *penicillium aspergillus* may be able to 1α-hydroxylate other substrates.

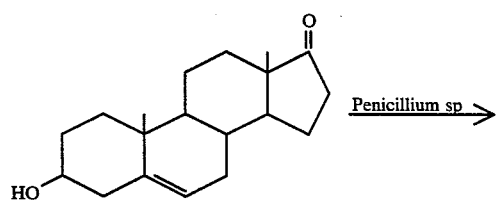

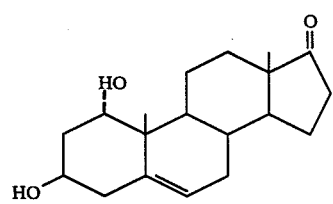

Dodson, R. M., Goldkamp, A. M., and Muir, R. D., JACS, 1957, 79, 3921.

Dodson, R. M., Goldkamp, A. M., and Muir, R. D., JACS, 1960, 82, 4026.

Penicillium hydroxylates DHEA at C-1 in the α-position. Therefore, other substrates that look like DHEA should by hydroxylated at C-1 by this enzyme.

C-2 Hydroxylation
2α,3β-dihydroxyandrost-5-en-17-one

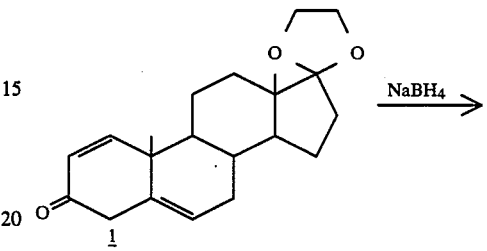

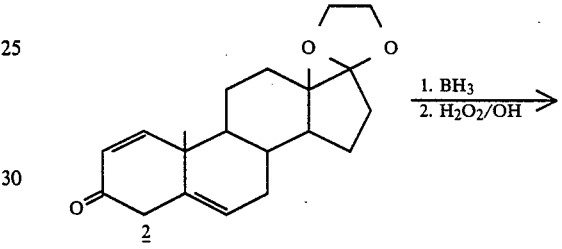

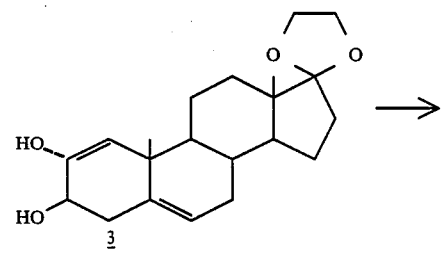

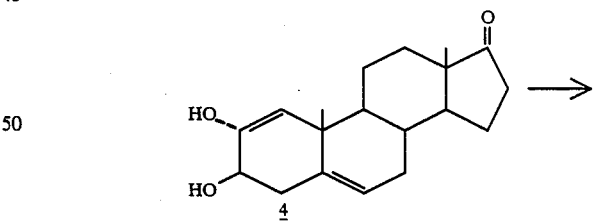

Reduction of androsta-1,5-dien-3,17-dione-17-ketal 1 with sodium borohydride yields 3β-hydroxyandrosta-1,5-diene-17-one 17-ketal 2. Hydroxylation of the C-1 double bond by hydroboration followed by oxidation with alkaline hydrogen peroxide affords 2α,3β-dihydroxyandrost-5-en-17-one 17-ketal 3. Deprotection of the C-17 ketone with aqueous acid yields 2α,3β-dihydroxyandrost-5-en-17-one, 4.

Carbon-4 Hydroxylation

31

-continued

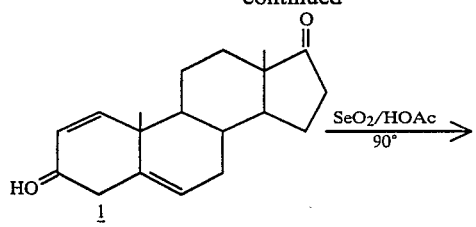

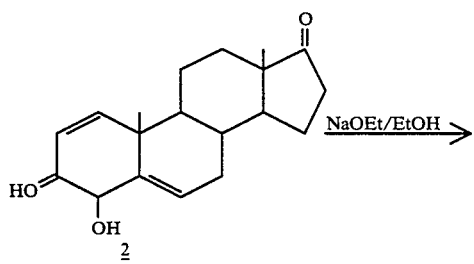

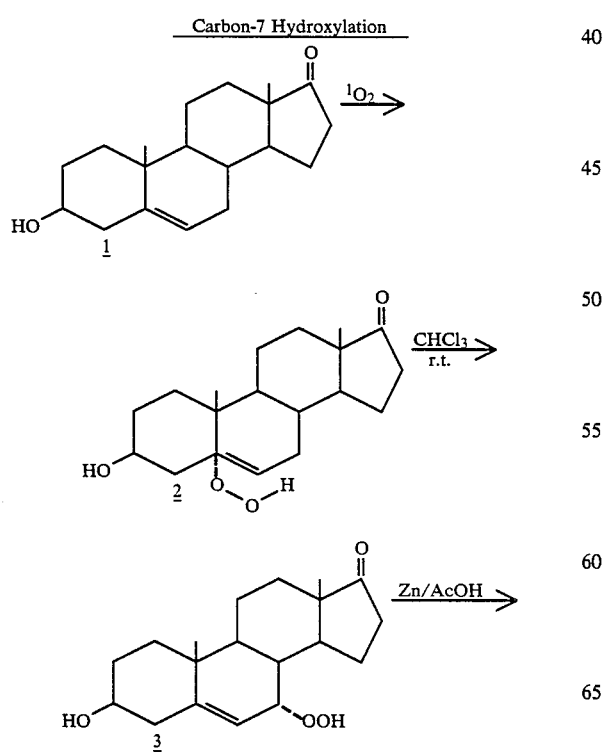

Selenium dioxide oxidation of 3β-hydroxyandrost-5-en-17-one yields 3β,4β-dihydroxyandrost-5-en-17-one 2. The axial C-4 alcohol may be epimerized to the equatorial position by reaction with sodium ethoxide in ethanol to yield 3β,4α-dihydroxyandrost-5-en-17-one, 3.

Carbon-7 Hydroxylation

32

-continued

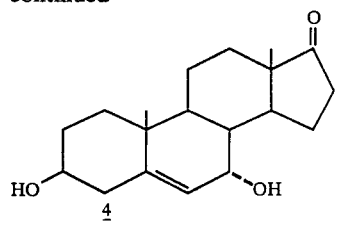

3β-Hydroxyandrost-5-en-17-one (DHEA) 1 reacts with singlet oxygen to yield 5α-hydroperoxy-3β-hydroxyandrost-6-en-17-one 2. This hydroperoxide undergoes a rearrangement when in chloroform solution to yield 7α-hydroperoxy-3β-hydroxyandrost-5-en-17-one, 3. Treatment of the hydroperoxide with zinc and acetic acid yields 3β,7α-dihydroxy-androst-5-en-17-one, 4.

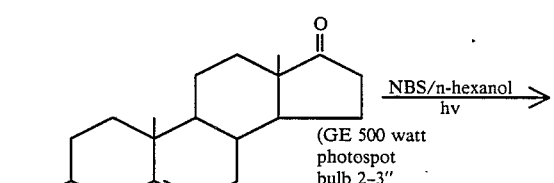

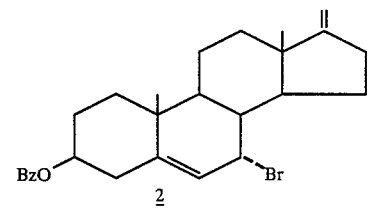

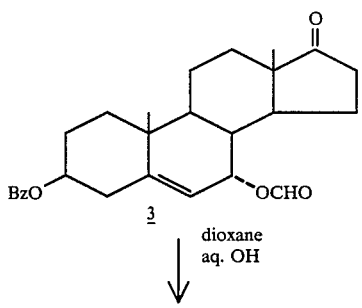

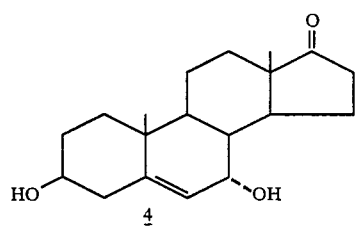

Alternatively, irradiation for approximately 15 minutes of 3β-benzyloxy-5-androsten-17-one 1 in the presence of NBS produces the 7-αBromo-3β-benzyloxy-5- androsten-17-one 2. The light source is provided by a G.E. 500 watt photospot bulb, which is placed 2-3" from the flask. Reaction of 2 with sodium formate in the presence of methyl t-butyl ether produces the formate ester 3. Substitution with aqueous base, such as OH⁻, results in the 3,7-dihydroxy-5-androsten-17-one 4.

Carbon-11 Hydroxylation

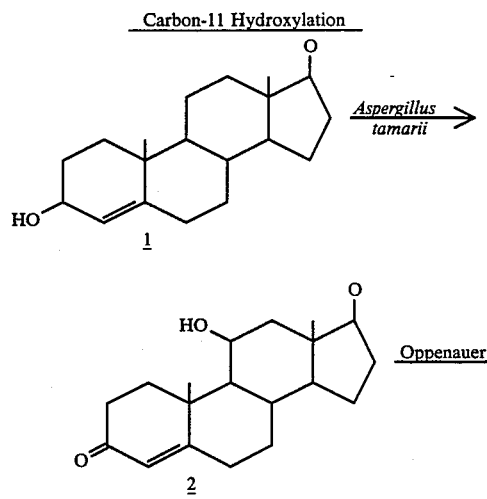

D. R. Brannon, J. Martin, A. C. Ochlschlager, N. N. Durham, and L. H. Zalkow, J. Org. Chem. 1965, 30, 760.

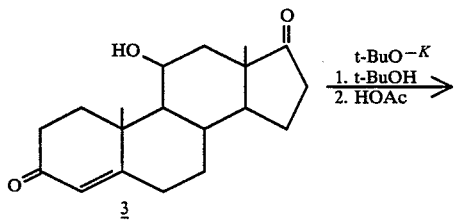

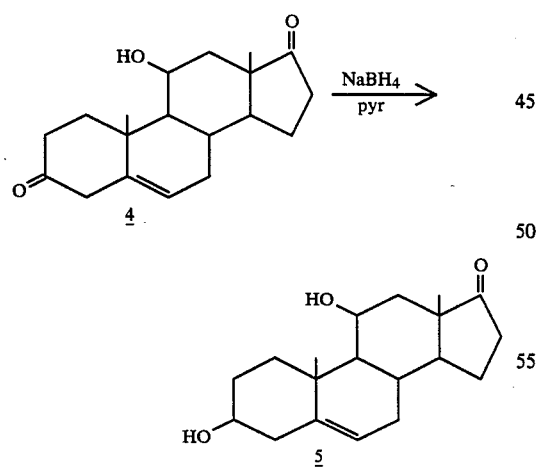

Hydroxylation of testosterone 1 at Carbon-11 using *Aspergillus tamarii* affords 11β,17β-dihydroxyandrost-4-en-3-one 2. Oppenauer oxidation of 2 oxidizes the 17β-alcohol in the presence of the hindered 11β-hydroxyl group to yield 11β-hydroxyandrost-4-en-3,17-dione, 3. Migration of the double bond out of conjunction by treatment with potassium t-butoxide followed by protonation with acetic acid yields 11β-hydroxyandrost-5-en-3,17-dione 4. Selective reduction of 4 yields 3β,11β-dihydroxyandrost-5-en-17-one, 5.

Hydroxylation at Carbon-16

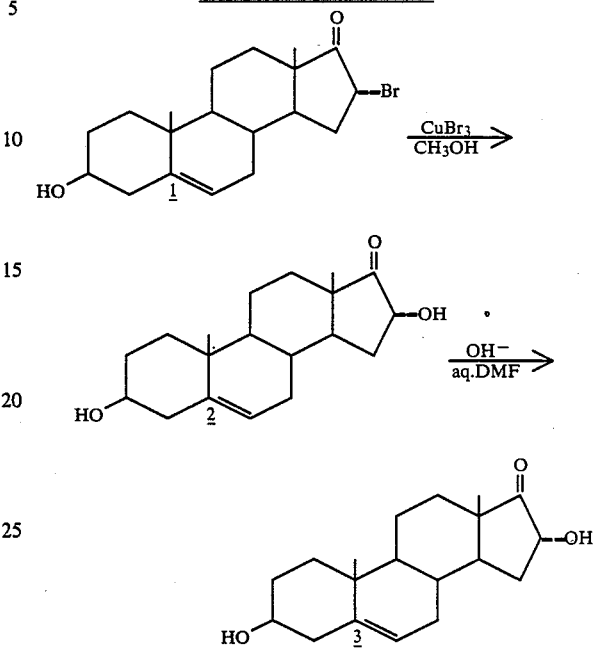

Bromination of DHEA (1) with cupric bromide yields 16α-bromo-DHEA, 2. Treatment of the bromo ketone 2 with sodium hydroxide in aqueous dimethylformamide gave 3β,16α-dihydroxyandrost-5-en-17-one, 3. See M. Numazawa, M. Nagaoka, Y. Osawa, J. Org. Chem. 1982, 47, 4024.

The following procedures are representative of procedures for halogenation at Carbon-1, 2, 3, 4, 6, 7, 11 or 16.

Halogenation at Carbon-1

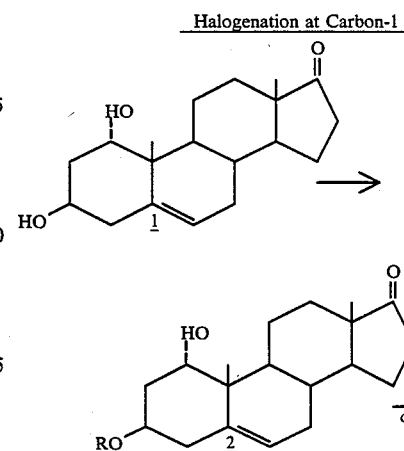

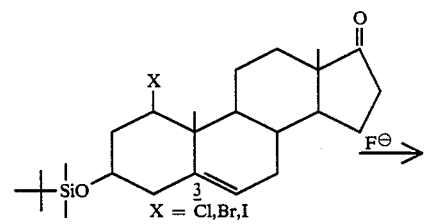

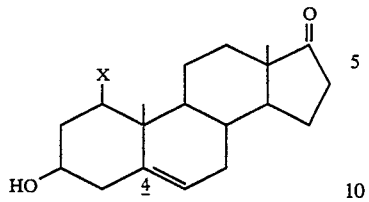

Selective protection of the Carbon-3 hydroxyl in the presence of the 1α-hydroxyl group should yield 2. For example, 1α,3β-dihydroxyandrost-5-en-17-one 1 reacts with t-butyl-dimethyl silyl chloride in the presence of imidazole using dimethylformamide as a solvent to yield 1α,3β-dihydroxyandrost-5-en-17-one 3t-butyl-dimethylsilyl ether, 2. Reaction of 2 with thionyl chloride, or phosphorous tribromide or catechol phosphochloridate followed by iodine yields the corresponding 1β-chloro, bromo or iodo derivatives 3. Reaction of 3 (R=Cl, Br, I) with tetrabutyl ammonium fluoride yields 1β,-halo-3β-hydroxyandrost-5-en-17-one, 4 (R=Cl, Br or I). The fluoride (4, R=F) may be synthesized via a similar route using an ester as the protecting group at C-3 and reacting the 1α-hydroxyl group with diethyl (2-chloro-1,1,2-trifluoroethyl)amine. Hydrolysis should yield 1,β-fluoro-3β-hydroxyandrost-5-en-17-one, 4, R=F.

Halogenation at Carbon-2

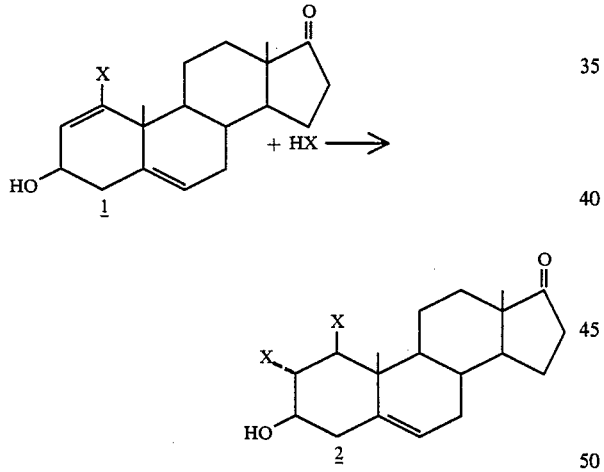

Addition of HX across the C-1 double bond in 3β-hydroxyandrosta-1,5-diene-17-one, 1, yields a mixture of the C-1 and C-2 halogenated steroids. Separation affords 2-halo-3β-hydroxyandrost-5-en-17-one (2, R=F, Cl, Br, I).

Halogenation at Carbon-2

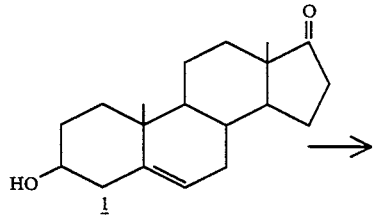

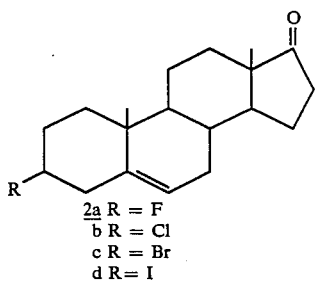

Reaction of 3β-hydroxyandrost-5-en-17-one 1 with diethyl (2-chloro-1,1,2-trifluoroethyl) amine yields 3β-fluoroandrost-5-en-17-one 1. Reaction of 1 with thionyl chloride yields 3β-chloroandrost-5-en-17-one, 2b. Reaction of 1 with phosphorus tribromide yields 3β-bromoandrost-5-en-17-one, 2c. Reaction of 1 with catechol phosphochloridate followed by iodine yields 3β-iodoandrost-5-en-17-one 2d.

Halogenation at Carbon-4

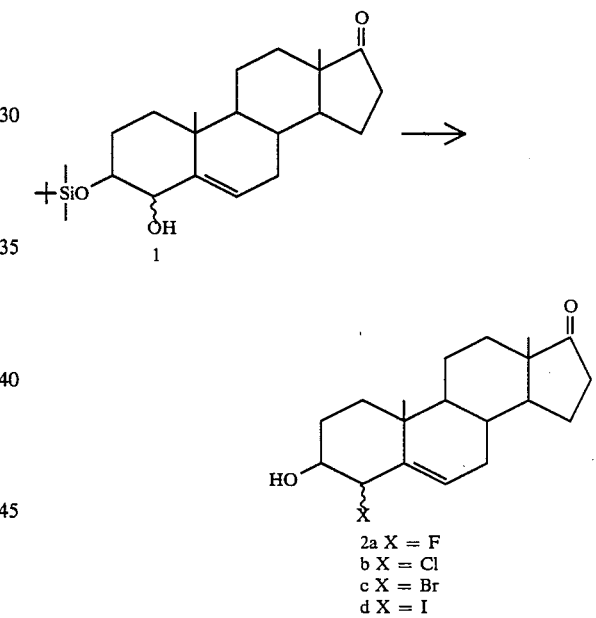

With the 3β-hydroxyl group protected as its t-butyl-dimethylsilyl ether the C-4 hydroxyl may be chlorinated using thionyl chloride. Treatment with fluoride ion cleaves the silyl ether to yield 4ξchloro-3β-hydroxyandrost-5-en-17-one, 2b. Reaction of 3,4-dihydroxyandrost-5-en-17-one 3-t-butyldimethylsilyl ether 1 with O-phenylene phosphochloridite, followed by displacement with bromide ion and cleavage of the silyl ether with fluoride ion yields 4ξbromo-3β-hydroxyandrost-5-en-17-one, 2c. Reaction of 1 with catechol phosphochloridate, followed by iodine and cleavage of the silyl ether with fluoride yields 4ξiodo-3β-hydroxyandrost-5-en-17-one, 2d. Fluorination of 3β,4ξdihydroxyandrost-5-en-17-one 3-acetate with diethyl (2-chloro-1,1,2-trifluoroethyl) amine followed by hydrolysis of the ester yields 4ξfluoro-3β-hydroxyandrost-5-en-17-one, 2a.

Halogenation at Carbon-6

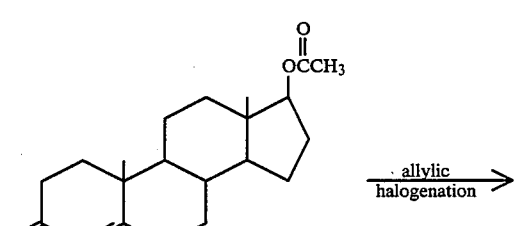

1

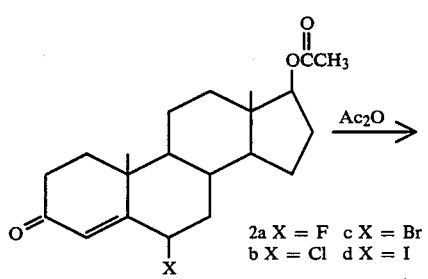

2a X = F    c X = Br
b X = Cl   d X = I

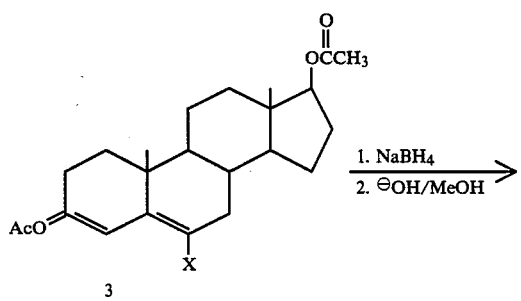

3

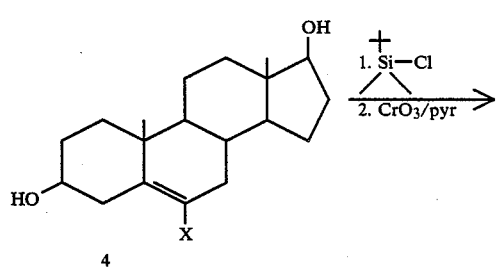

4

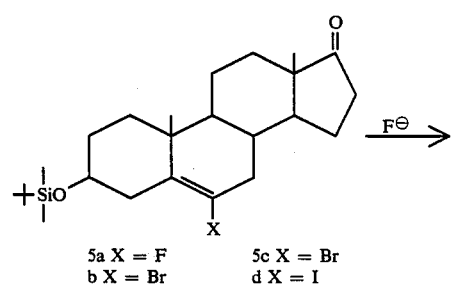

5a X = F    5c X = Br
b X = Br    d X = I

-continued
Halogenation at Carbon-6

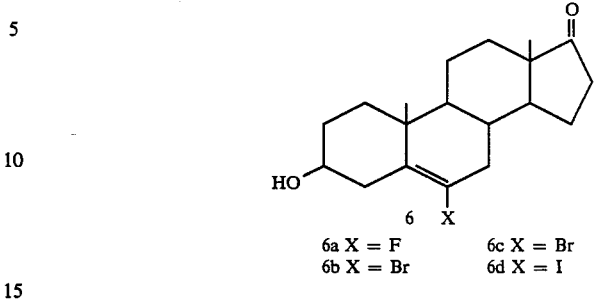

6a X = F    6c X = Br
6b X = Br   6d X = I

Allylic bromination of 17β-hydroxyandrost-4-en-3-one 17-acetate 1 using N-bromosuccinimide together with a radical initiator such as light or benzoyl peroxides or aliphatic azo compounds [RR'C(CN)—N=N—C(CN)RR'] e.g. azobisisobutyronitrile yields 6β-bromo-17β-hydroxyandrost-4-en-3-one 17-acetate, 2. Allylic chlorination of 1 using sulfuryl chloride together with a radical initiator such as light or benzoyl peroxide or aliphatic azo compounds yields 6β-chloro-17β-hydroxyandrost-4-en-3-one 17-acetate, 2c. Allylic iodination of 1 using mercuric iodide and light yields 6β-iodo-17β-hydroxyandrost-4-en-3-one-17-acetate, 2d. Acetylation of 2 with acetic anhydride and p-toluene sulfonic acid in toluene yields 6-halo-3,17β-dihydroxyandrosta-3,5-diene 3,17-diacetate 3. Sodium borohydride reduction of 3 followed by basic hydrolysis of the C-17 acetate yields 6-haloandrost-5-en-3β,17β-diol, 4. Selective protection of the C-3 hydroxyl group as its t-butyldimethylsilyl ether followed by chromium trioxide oxidation of the C-17-hydroxyl group yields 6-halo-3β-hydroxyandrost-5-en-17-one 3-t-butyldimethylsilyl ether 5. Treatment of 5 with fluoride ion yields 6-halo-3β-hydroxyandrost-5-en-17-one, 6. The C-6 fluoro analogue may be synthesized from the C-6 bromo diacetate, 3c, by treatment with silver fluoride. Following the above sequence, reaction of 6-fluoro-3,17β-dihydroxyandrosta-3,5-diene-3,17-diacetate, 3a with sodium borohydride yields, 6-fluoro-3β-hydroxyandrost-5-en-17-one, 6a.

Halogenation at Carbon-7

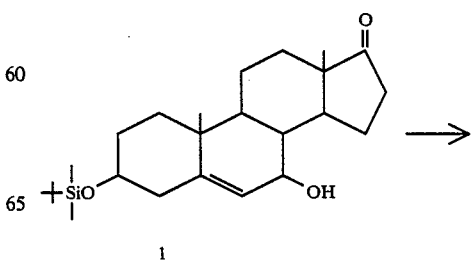

1

-continued
Halogenation at Carbon-7

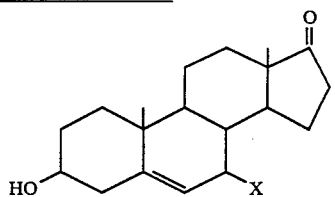

2a X = F
b X = Cl
c X = Br
d X = I

Reaction of 3β,7-dihydroxyandrost-5-en-17-one-3-t-butyldimethylsilyl ether 1 with thionyl chloride yields the C-7 chloro-steroid. Deprotection of the 3β-hydroxyl group affords 7-chloro-3β-hydroxyandrost-5-en-17-one, 2b. Reaction of 1 with catechol phosphochloridate followed by displacement with bromide ion and deprotection yields 7-bromo-3β-hydroxyandrost-5-en-17-one, 2c. Similarly reaction of 1 with catechol phosphochloridate followed by displacement with iodine and deprotection yields 7-iodo-3β-hydroxyandrost-5-en-17-one, 2d. Fluorination of 3β,7-dihydroxyandrost-5-en-17-one 3-acetate with diethyl (2-chloro-1,1,2trifluoro-ethyl) amine followed by hydrolysis of the ester yields 7-fluoro-3β-hydroxyandrost-5-en-17-one, 2a.

Halogenation at Carbon-9

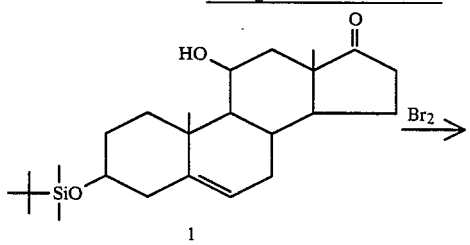
1

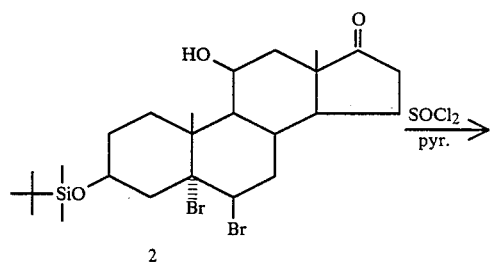
2

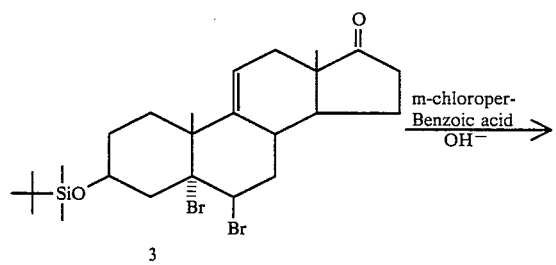
3

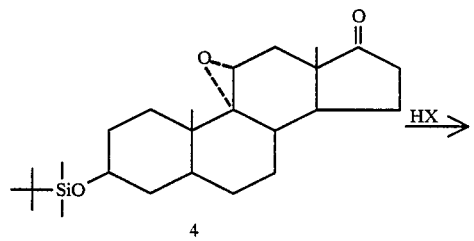
4

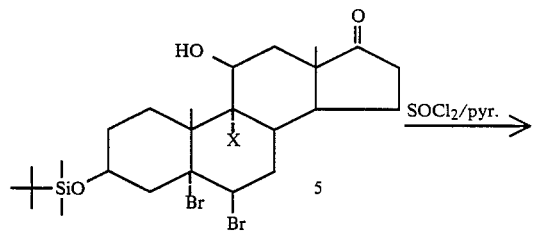
5

Halogenation at Carbon-9

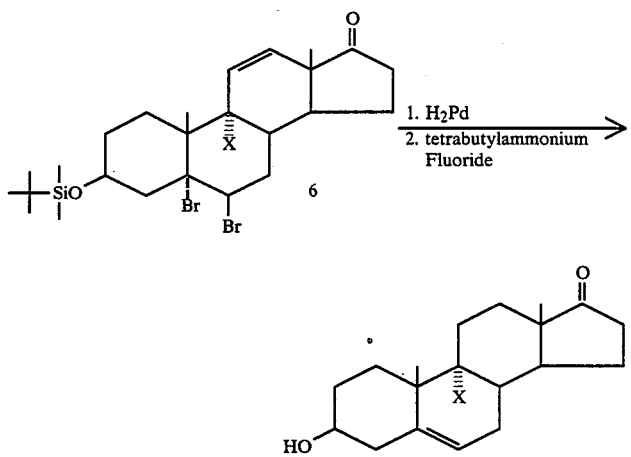

Bromination of 3β,11α-dihydroxyandrost-5-en-17-one 3-t-butyldimethylsilyl ether 1 yields the dibromide 2. Reaction of 2 with thionyl chloride produces the unsaturated compound, 3β-hydroxy-5,6-dibromo-9(11)-androsten-17-one-3-t-butyl-dimethylsilyl ether 3. 3 is epoxidized with perbenzoic acid forming 4. Reaction of 4 with hydrohalic acid, such as HCl, HBr, forms the 9α-halo derivative 5. Dehydration of 5 with thionyl chloride produces the unsaturated compound, the 3β-hydroxy-5,6-dibromo-11-androsten-17-one-3-t-butyl-dimethylsilyl ether 6. Catalytic hydrogenation of 6 followed by removal of the protecting group forms the 3-βhydroxy-9-α-halo-5-androsten-17-one.

Halogenation at Carbon-11

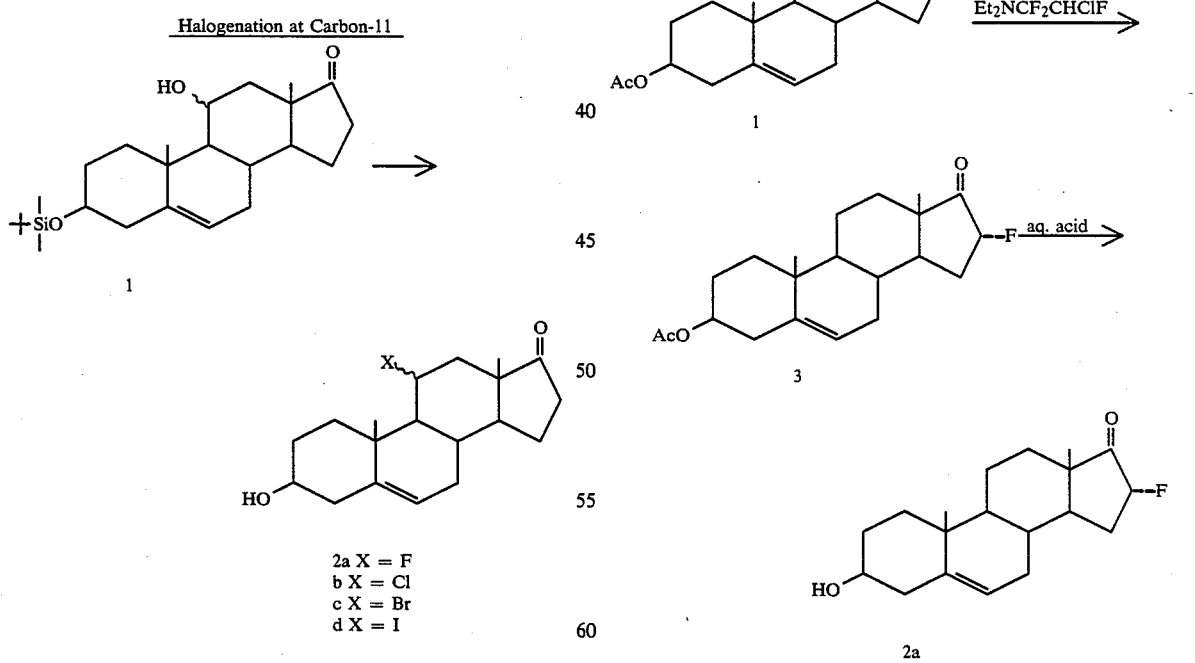

2a X = F
b X = Cl
c X = Br
d X = I

Reaction of 3β,11α-dihydroxyandrost-5-en-17-one 3-t-butyldimethylsilyl ether 1 with OPPC followed by chloride yields the C-11 chloro steroid. Deprotection of the 3β-hydroxyl group affords 11ξ-chloro-3β-hydroxyandrost-5-en-17-one, 2b. Reaction of 1 with OPPC followed by displacement with bromide ion and deprotection yields 11ξ-bromo-3β-hydroxy-androst-5-en- 17-one, 2c. Similarly reaction of 1 with OPPC followed by displacement with iodine and deprotection yields 11ξ-iodo-3β,hydroxyandrost-5-en-17-one 2d. Fluorination of 3β,11α-dihydroxyandrost-5-en-17-one 3-acetate with diethyl (2-chloro-1,1,2-trifluoroethyl)amine followed by hydrolysis of the ester yields 11ξ-fluoro-3β-hydroxy-androst-5-en-17-one, 2a.

Halogenation at Carbon-16

Reaction of 3β,16α-dihydroxyandrost-5-en-17-one 3β-acetate 1 with a fluorinating agent such as diethyl (2-chloro-1,1,2-trifluoroethyl)amine affords 16α-fluoro-3β-hydroxyandrost-5-en-17-one 3-acetate 3. Hydrolysis of the ester with aqueous acid yields 16α-fluoro-3β-hydroxyandrost-5-en-17-one, 2a.

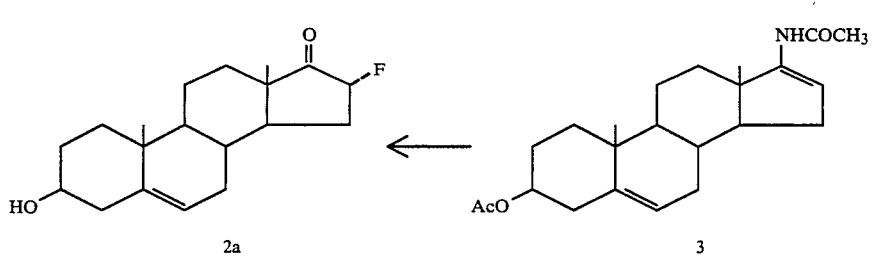

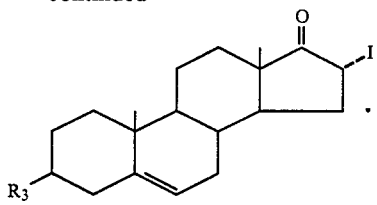

Alternatively, 2a could be prepared by treating an enamide, e.g., the enamide of Formula 3 with a fluorinating agent, such as perchloryl fluoride. Hydrolysis of the fluoro enamide acetate with aqueous acid gives 2a.

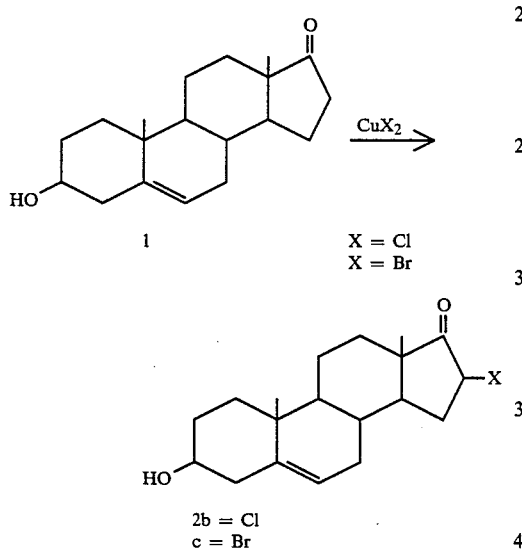

Reaction of 3β-hydroxyandrost-5-en-17-one 1 with cupric bromide yields 16α-bromo-3βhydroxyandrost-5-en-17-one, 2c[1]. Reaction of 1 with cupric chloride and lithium chloride yields 16α-chloro-3β-hydroxyandrost-5-en-17-one, 2b[2]

[1] E. R. Glazier, J. Org. Chem. 1962, 27, 4397
[2] E. M. Kosower, et al., J. Org. Chem., 1963, 28, 630

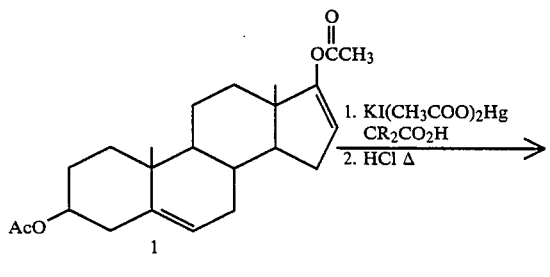

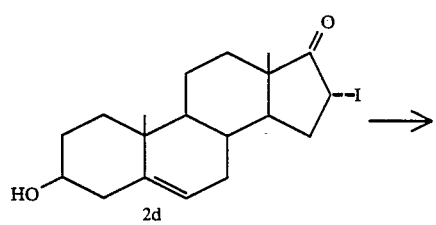

Reaction of 3β,17-dihydroxyandrosta-5,16-diene 17-acetate 1 with mercuric acetate followed by treatment with potassium iodide yields the C-16αiodide which hydrolyses with acid to yield 3β-hydroxy-16α-iodoandrost-5-en-17-one, 2d. Reaction of 2d with silver fluoride yields 3β-hydroxy-16α-fluoroandrost-5-en-17-one, 2a.

Alternatively, 2d can be formed from the reaction of 1 with N-iodo-succinimide. In addition, the reaction of 2c with NaI/acetone overnight results in a mixture of 16α and 16βI-3β-hydroxy-5-androsten-17-ones.

ALKOXYLATION

The alkoxy groups are derived from the corresponding alcohols. The methoxy substituent for example is formed by reacting the corresponding alcohol in methylene chloride with boron trifluoride and etheral diazomethane according to the procedure of Caserio, et al. JACS, 80, 2584 (1958). Similarly, the ethoxy substituent is formed by reacting the corresponding alcohol in methylene chloride with boron trifluoride and etheral diazoethane, generated in situ. Alternatively, the alkoxy substituents can also be added to the steroid ring by reacting the alcohol under Williamson reaction conditions with RX, where X is an organic leaving group such as halide tosylate or mesylate and R is loweralkyl. Any base normally employed to deprotonate an alcohol may be used, such as sodium hydride, sodium amide, sodium, sodium, sodium hydroxide, triethylamino or disopropyl ethylamine. Reaction temperatures are in the range of −78° C. to reflux. The reaction is carried out in a solvent that will dissolve both reactants and is inert to both reactants and products as well. Solvents include, but are not limited to, diethyl ether, tetrahydrofuran, N,N-dimethylformamide, methylene chloride, and the like.

The ketone should be protected with protecting groups known in the art. Examples of many of the possible protecting groups that may be utilized are found in "Protective Groups in Organic Synthesis," by T. W. Green, John Wiley and Sons, 1981. For example, the ketone may be protected as the ethylene ketal.

CATALYTIC HYDROGENATION

Catalytic hydrogenation of 3β-substituted androst-5-enes yields almost exclusively 3β-substituted 5α- androstanes (for references see J. R. Lewis and C. W. Shoppee, *J. Chem. Soc.* 1955, 1365). Therefore all the syntheses of the substituted androst-5-enes described above can be used for the syntheses of the substituted 5α-androstanes, except those molecules which contain reducible double bonds such as the ethenyl and alkynyl derivatives. For these molecules the following syntheses are described.

Firstly an example of catalytic hydrogenation for the synthesis of 5α-androstanes from androst-5-enes is the synthesis of 3β-methyl-5α-androstan-17-one 2 from 3β-methylandrost-5-en-17-one 1. 3β-Methylandrost-5-en-17-one 1 (400 mg), prepared as described previously was dissolved in glacial acetic acid (80 ml). Palladium on carbon (10%, 100 mg) was added and the solution maintained under an atmosphere of hydrogen. When hydrogen uptake ceased, the solution was filtered through celite and evaporated to give solid which was recrystallized from methanol to yield 3β-methyl-5α-androstan-17-one, 2, (320 mg, 80% yield). MP 107°–108° C., $^1$H NMR (CDCl$_3$)δ 0.86 (d, 3H, J-5Hz, methyl at C-3), 0.85 (s, 3H, C-19 Me), 0.79 (s, 3H, C-18 Me).

Anal Calc for C$_{20}$H$_{32}$O: C, 83.26%, H 11.18%
Found: C, 82.99%, H 11.35%

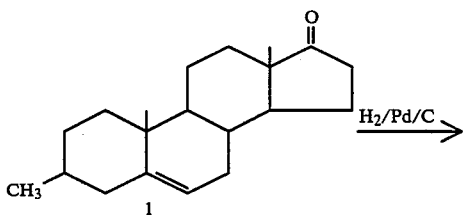

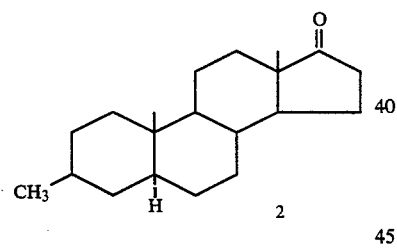

The following examples further illustrate the invention:

EXAMPLE 1

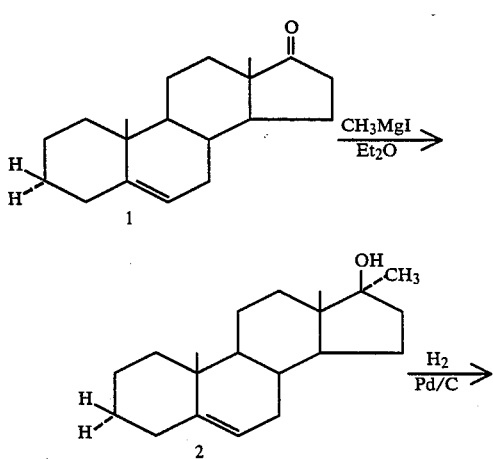

-continued

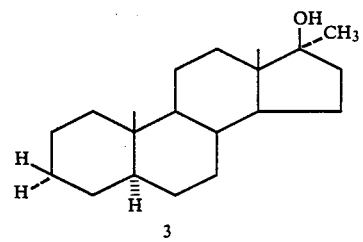

A. 17α-Methyl-5-Androsten-17 β-ol (2) from 1

Treatment of 5-androsten-17-one in ether with methyl magnesium iodide by the method of Miescher and Harer (Helv. Chem. Acta, 22, 962 (1939)) affords 2 as the major product.

B. 17α-Methyl-5α-Androstan-17β-ol (3) from 2

Catalytic hydrogenation of the olefin 2 using palladium on carbon furnishes the saturated product 3.

EXAMPLE 2

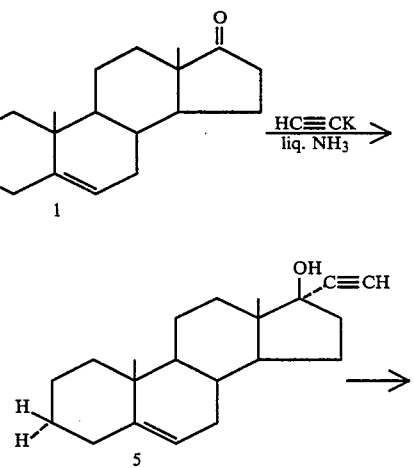

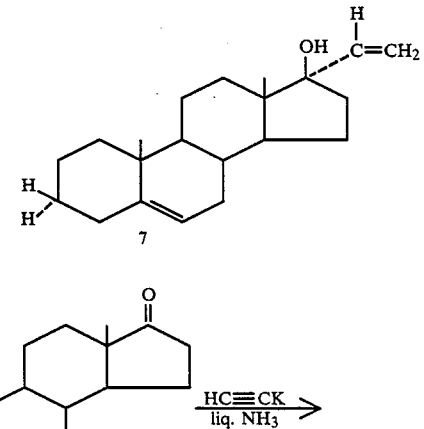

-continued

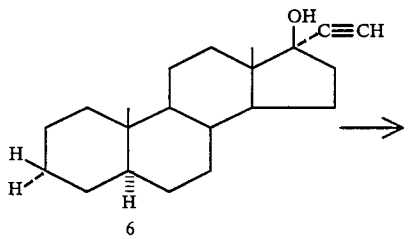
6

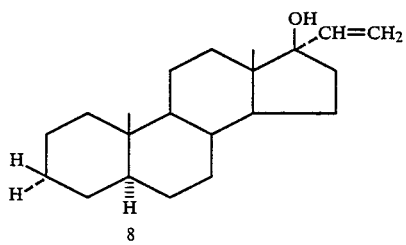
8

A. 17α-Ethynyl-5-Androsten-17β-ol (5) and 17α-Ethynyl-5α-Androstan-17β-ol (6) from 1 and 4

Reaction of the appropriate 17-one with potassium acetylide in liquid ammonia (Inhoffen, et al., Chem. Ber., 71, (1938)) affords the corresponding 17α-ethynyl-17β-ols.

B. 17α-Ethenyl-5-Androsten-17β-ol (7) and 17α-Ethenyl-5α-Androstan-17β-ol (8)

Partial hydrogenation of the 17-ethynyl carbinols 5 and 6 over deactivated palladium (Sandoval, et al., JACS, 77, 148 (1955)) affords the 17-ethenyl carbinols 7 and 8 since this reaction occurs more readily than the saturation of any other functional group (See Hershberg, et al., JACS, 73, 5073 (1951)).

EXAMPLE 3

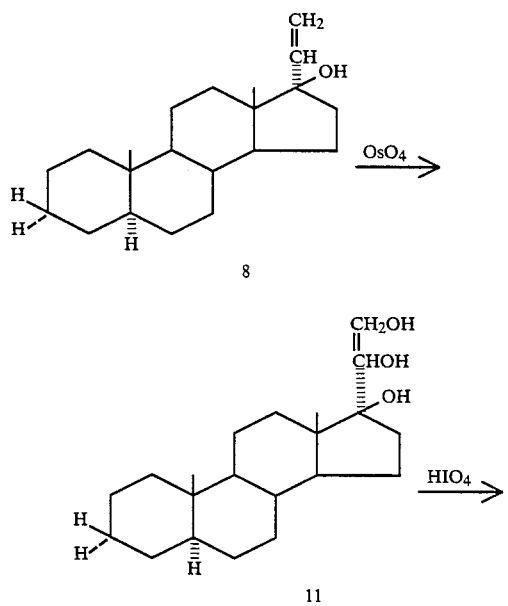

-continued

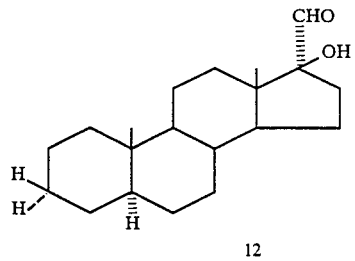
12

17α-Formyl-5α-androstan-17β-ol (12) from 8

Treatment of the 17α-ethenyl carbinol in pyridine with one equivalent of osmium tetroxide followed by addition of sodium bisulfite to decompose the 20,21-osmate ester affords the 17α-pregnane-triol 11. Treatment of 11 with one equivalent of periodic acid in aqueous ethanol furnishes the aldehyde 12.

EXAMPLE 4

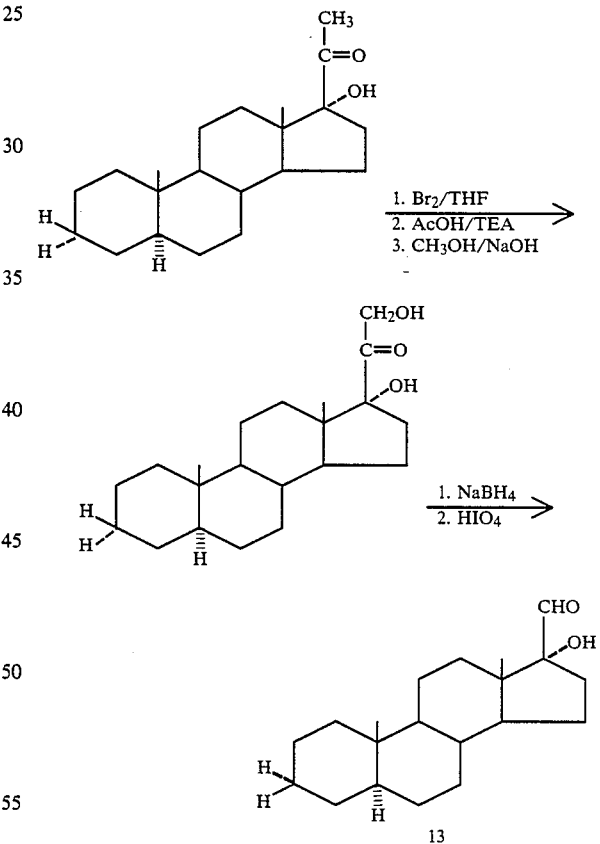

17β-Formyl-5α-androstan-17α-ol (13)

Sequential bromination, acetoxylation and deacetylation of 17α-hydroxy-5α-pregnan-20-one by published methods affords the α-ketol, 17,21-dihydroxy-5α-pregnan-20-one. Reduction of this diolone with sodium borohydride gives chiefly 5α-pregnane-17,20β,21-triol. Treatment of the glycerol with one equivalent of periodic acid as in the preparation of 12 provides the epimeric aldehyde 13.

EXAMPLE 5

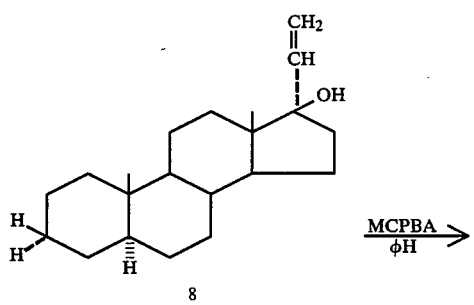

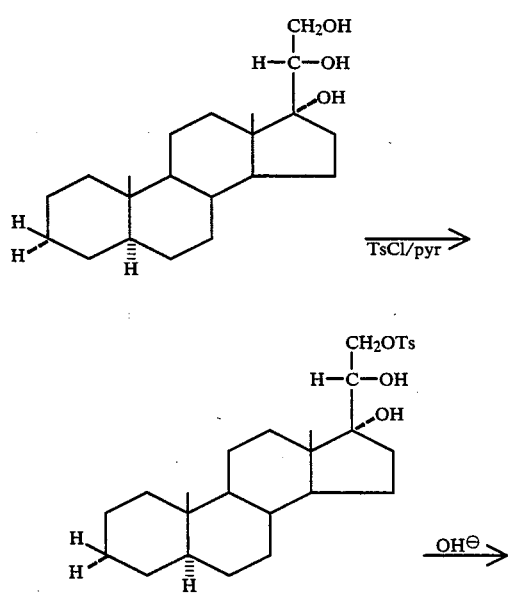

20,21-Epoxy-5α,17α-pregnan-17β-ol (14)

Treatment of the 17α-ethenyl carbinol with m-chloroperbenzoic acid in benzene affords the 20,21-epoxide 14.

EXAMPLE 6

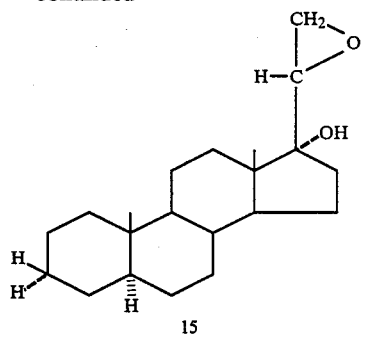

20,21-Epoxy-5α-pregnan-17α-ol (15)

Treatment of the previously described glycerol with one equivalent of p-toluenesulfonyl chloride in pyridine affords the 21-monotosylate. Alkaline treatment gives the 20α,21-epoxide 15 (See M. L. Lewbart, JOC, 33, 1695 (1968)).

EXAMPLE 7

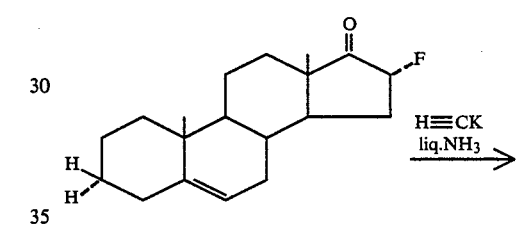

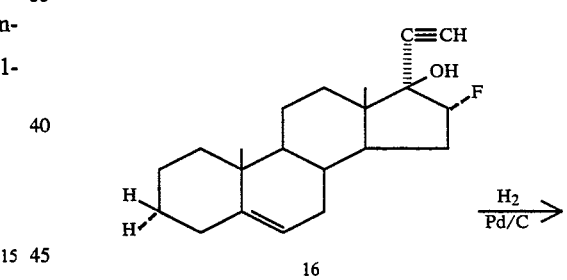

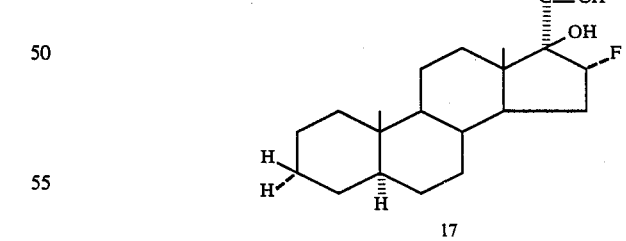

16α-Fluoro-17α-ethynyl-5-androsten-17β-ol (16) and 16α-Fluoro-17α-ethynyl-5α-androstan-17β-ol (17)

Treatment of 16α-fluoro-5-androsten-17-one with potassium acetylide in liquid ammonia as in the preparation of 5 gives the 17α-ethynyl carbinol 16. Selective catalytic hydrogenation of 16 or direct reaction of 16α-fluoro-5α-androstan-17-one with potassium acetylide in liquid ammonia supplies the ethynyl carbinol 17.

EXAMPLE 8

16α-Fluoro-5-Androsten-17-one

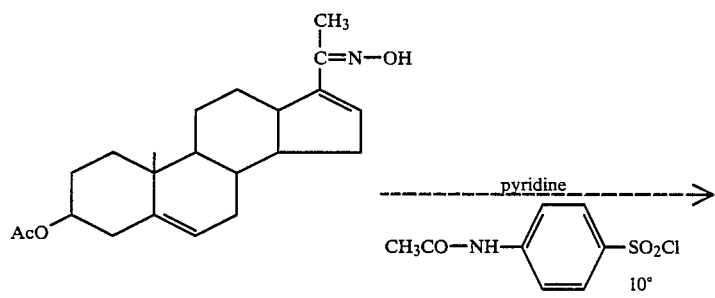

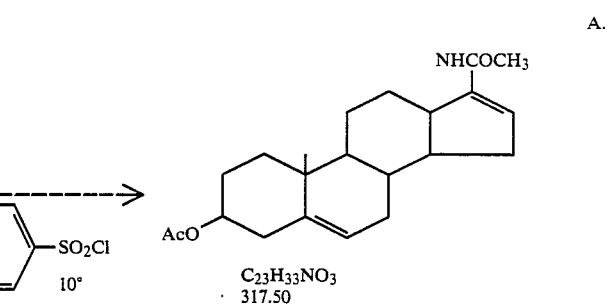

To a solution of the oxime (30.0 g) in 120 ml of pyridine at 10° while stirring magnetically was added 30.0 g of p-acetamidobenzenesulfonyl chloride. The solution was stirred for 2 hours while maintaining the temperature at 10°±2° C. The clear yellow-orange reaction mixture was added to 1L of ice water and the resulting orange, oily suspension was extracted with 500 ml of methylene chloride. The organic layer was washed with water, filtered through anhydrous sodium sulfate, and concentrated to dryness. Several additions of toluene followed by drying in vacuo served to remove most of the pyridine. The orange, semi-crystalline residue was digested with 500 ml of methylene chloride. The insoluble fraction was filtered off, washed with methylene chloride, and discarded. To the filtrate was added an equal volume of ethanol. Concentration in an air stream to approximately 300 ml afforded 21.1 g of yellow needles. mp 228°-230°. Fractional crystallization of the mother liquors gave an additional 1.90 g, mp 227°-230°. Yield=23.0 g (76.7%); λ max 3320, 1530 (NHCOCH$_3$), 1732, 1240, 1030 cm$^{-1}$ (3β-acetate).

B. Reaction of 17-acetamide-5,16-androstadien-3B-ol Acetate with Perchloryl Fluoride in Pyridine (See S. Nakanishi, J. Med. Chem 7, 108 (1964))

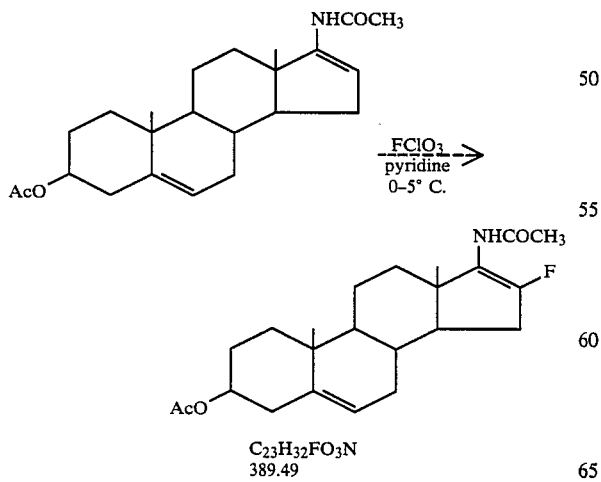

Into a solution of the enamide (7.50 g) in pyridine (400 ml) at 0°-5° C. was bubbled perchloryl fluoride for 4 minutes. The reaction mixture was added to 1500 ml of ice water and concentrated hydrochloric acid was added slowly with magnetic stirring to pH 1-2. The colorless, crystalline percipitate was filtered off and washed thoroughly with water. Recrystallization from methylene chloride-isooctane gave 4.40 g of light yellow prisms, mp 165°-169°, λ max 3250, 1635 (NHCOCH$_3$) 1735, 1240, 1030 cm$^{-1}$ (3B acetate). Fractional crystallization of the mother liquors gave an additional 0.52 g, mp 162-165. Yield=4.92 g (66%). The final mother liquor residue (3.03 g) was sufficiently pure for acid hydrolysis to the 16α-fluoro 17-one (see C).

C. Acid Hydrolysis of fluroenamide Acetate to 16α-Fluoro-3β-Hydroxy-5-androsten-17-one

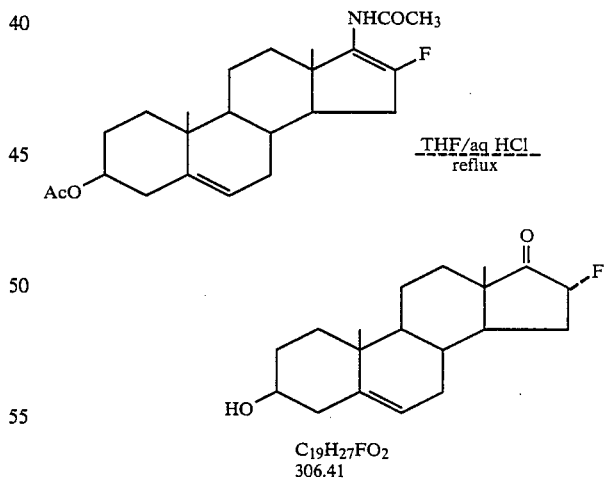

To a solution of the fluroenamide acetate (4.20 g) in 150 ml each of anhydrous tetrahydrofuran and water was added 15 ml of concentrated hydrochloric acid. The mixture was refluxed for 14 hours, then partitioned between methylene chloride and water. The organic layer was washed with water, filtered through anhydrous sodium sulfate, and concentrated to dryness. Crystallization from acetone-isooctane furnished 3.16 g of fine needles, mp 145°-147° (96% yield), λ max 3350 (hydroxyl), 1752 cm$^{-1}$ (16-fluoro-17-one).

D. Preparation of 3β-Iodo-16α-Fluoro-5-Androsten-17-one (See Corey and Anderson, JOC 32, 4160, 1967)

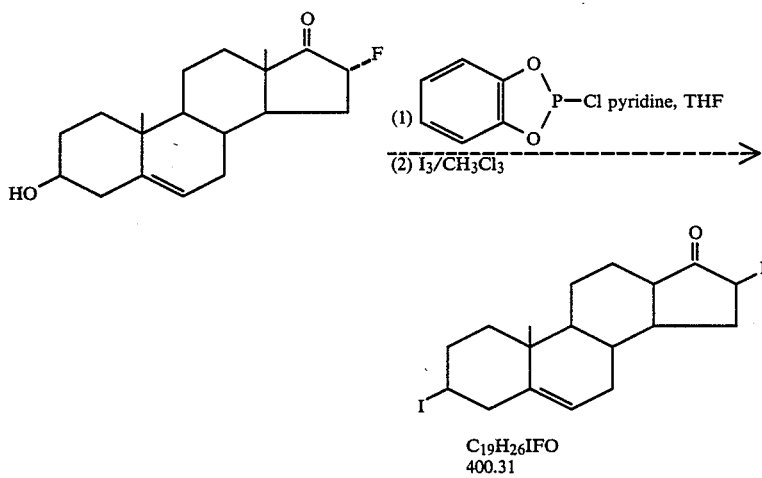

To a solution of pyridine (0.41 ml) and 0-phenylenephosphorochloridite (0.6 ml) in anhydrous THF (10 ml) at 0° was added 1.53 g (5 mmoles) of the hydroxyfluoroketone in 10 ml of THF. After stirring for two hours at room temperature, the pyridinium chloride was filtered off and washed with THF. After removal of the solvent in vacuo, the crude phosphite ester was dissolved in 25 ml of methylene chloride and treated with 1.27 g of iodine for three hours at room temperature. The reaction mixture was washed successively with 15 ml of 1N sodium hydroxide and water, filtered through anhydrous sodium sulfate, and the product was crystallized from methylene chloride/methanol in a yield of 1.85 g (92.5%), mp 165°–167° (dec.) λ max 1755 cm$^{-1}$ (16-fluoro-17-one).

E. Reaction of Iodofluoroketone with Zinc/Acetic Acid

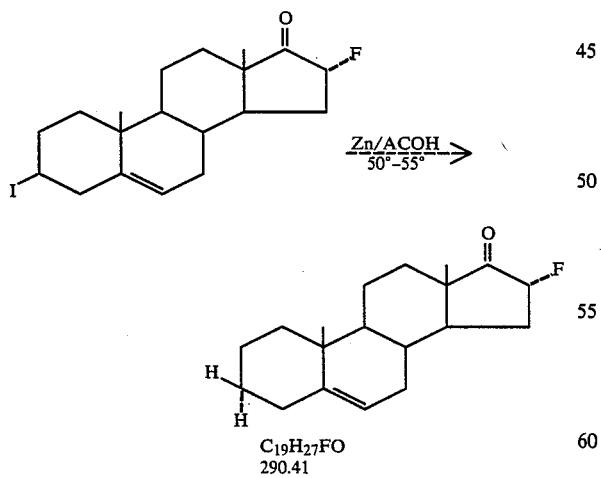

To a solution of 3β-iodo-16α-fluoro-5-androsten-17-one (1310 mg, 3.28 mmoles) in 40 ml of glacial acetic acid was added 2.62 g of zinc dust. The mixture was stirred magnetically at 50°–55° for one hour, then partitioned between methylene chloride and water. The organic layer was washed with dilute sodium hydroxide and water, filtered through anhydrous sodium sulfate and concentrated to dryness. Crystallization from methylene chloride-methanol gave 630 mg of a colorless platelet mp 167°–169°. Fractional crystallization of the mother liquors gave an additional 140 mg, mp 165°–167°, raising the yield to 770 mg (81.0%); λ max 1752 cm$^{-1}$ (16-fluoro-17-one).

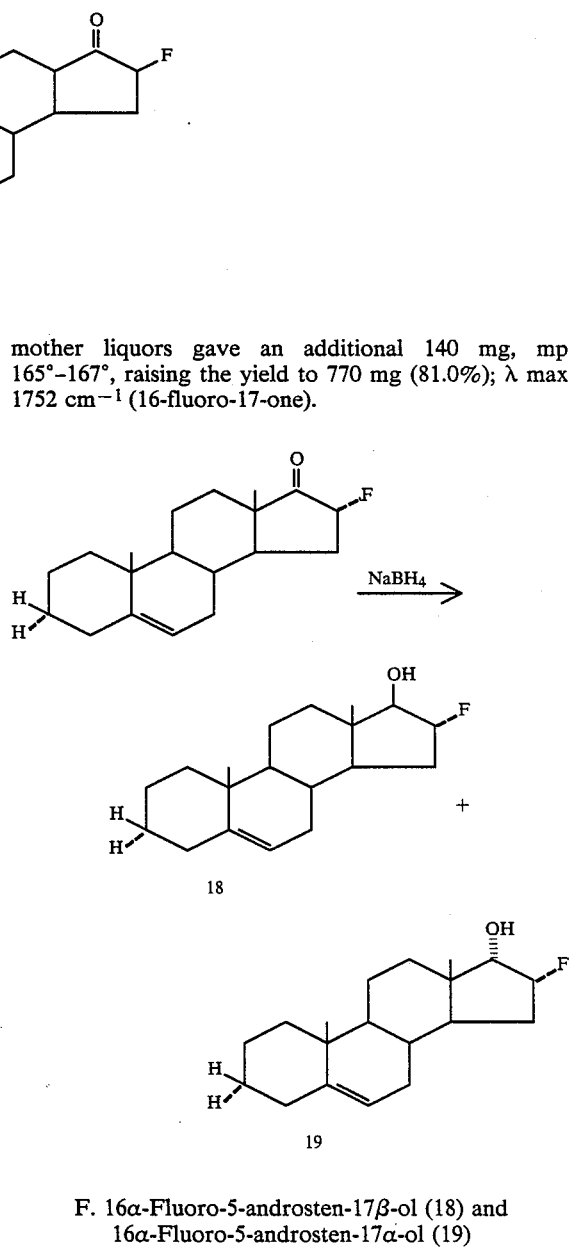

F. 16α-Fluoro-5-androsten-17β-ol (18) and 16α-Fluoro-5-androsten-17α-ol (19)

To 1.45 g (5 mmoles) of 16α-fluoro-5-androsten-17-one in 100 ml each of methylene chloride and methanol at 0° was added 250 mg of sodium borohydride. After stirring the mixture for 50 minutes at 0° excess acetic acid was added and the reaction mixture was partitioned between methylene chloride and water. Analysis of the reaction mixture by thin-layer chromatography in isooctane-ethyl acetate (20:5) disclosed roughly equal amounts of two products with Rf's 0.21 and 0.32, respectively. The mixture was subjected to silica gel column chromatography in isooctane ethyl acetate (85:15) on a 38×900 mm bed, collecting 12 ml/20 minutes.

Mobile Fraction. Tubes 52-80. Fine needles from acetone-isooctane: 280 mg, mp 125°-127° C. 100 mg, mp 124°-126°. Based on relative chromatographic mobilities this is 16α-fluoro-5-androsten-17α-ol 19. Treatment of an aliquot of 19 with Jones reagent gave starting material.

Polar Fraction. Tubes 91-120. Gelatinous needles from acetone isooctane: 185 mg, mp 167°-169°; 350 mg (from acetonitrile), mp 159°-160°; 100 mg, mp 154°-156°. This is 16α-fluoro-5-androsten-17β-ol (18). Treatment of 18 with Jones reagent gave starting material.

EXAMPLE 9

16αBromo-5-androsten-17β-ol/and 16α Bromo-5-androsten 17α-ol

A. Preparation of 16α Bromo-5-androsten-17-one

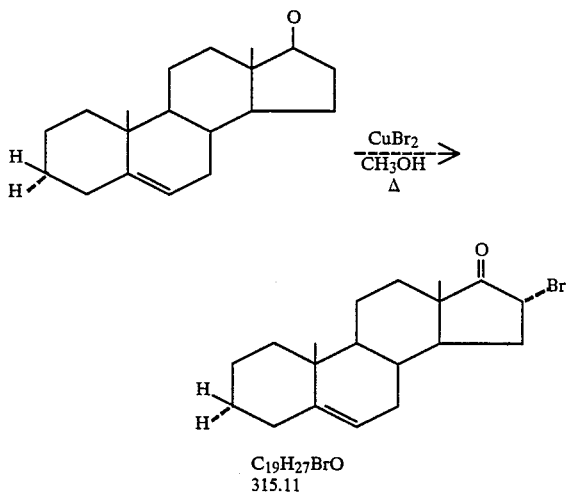

$C_{19}H_{27}BrO$
315.11

A solution of 5-androsten-17-one (10.88 g, 40 mmoles) in methanol (2L) was refluxed with 26.8 g (120 mmoles) of CuBr₂ for 17 hours. The reaction mixture was added to 2L of water and the resulting crystalline suspension was stirred several hours at 5° C. The product was filtered off, washed with water and recrystallized from methanol as colorless needles: 7.95 g, mp 172°-174°, 2.00 g, m.p. 165°-168°. High performance liquid chromatography (HPLC) of the mother liquor using ethyl acetate-n-hexane as eluent, afforded an additional 0.58 g of 16α-Bromide, raising the yield to 10.53 g (75.0%). In addition, 800 mg (5.7%) of 16B-Bromo-5-androsten-17-one, mp 149.5° to 152°, was obtained. Also obtained was 75 mg of 16, 16-dibromo-5-androsten-17-one, mp 194°-195°.

Preparation of 16α Bromo-5-androsten-17β-ol and 16α-Bromo-5-androsten-17α-ol

Sodium borohydride is added to the product of A according to the procedure described in Example 8F to afford the above-identified final products.

EXAMPLE 10

A. 16α-Hydroxy-5-androsten-17β-ol and 16α-Bromo-5-androsten-17α-ol

B. Synthesis of 16α Hydroxy-5-androsten-17-one

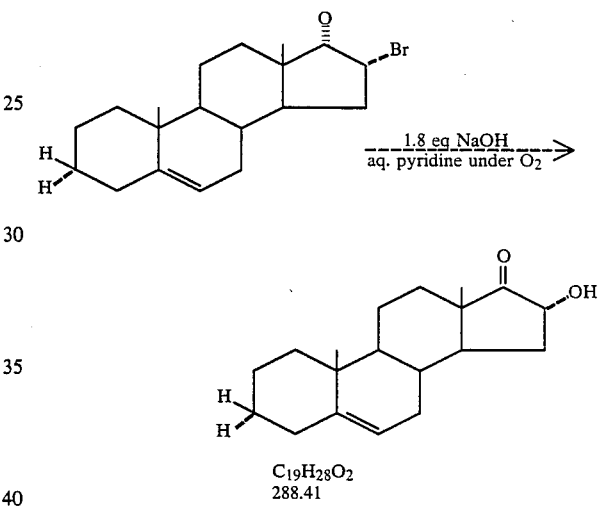

$C_{19}H_{28}O_2$
288.41

To a solution of 16α-Bromo-5-androsten-17-one (7.92 g, 20 mmoles) in pyridine (300 ml) and water (64 ml) in an oxygen atmosphere was added 36 ml (36 mmoles) of 1N NaOH. After stirring the mixture for 15 minutes at room temperature under O₂, it was added to 1L of ice water containing 330 ml of concentrated HCl. The crystallized precipitate which formed was filtered off, washed with water, and recrystallized from methanol as leaflets (2,80 g), mp 168°-172°. HPLC of the mother liquor on a silica gel column using isopropyl alcohol n-hexane as eluent furnished an additional 1.4 g of light yellow prisms, mp 170°-174°. The total yield of 16α-ol was 3.94 g (68.4%).

B. 16α-Hydroxy-5-androsten-17β-ol and 16α-Bromo-5-androsten-17α-ol

Sodium borohydride is added to the product of A according to the procedure described in Example 8F to afford the above-identified final products.

EXAMPLE 11

Preparation of 16α-methyl-5-androsten-17α-ol,
16β-methyl-5-androsten-17β-ol,
16β-methly-16α-fluoro-5-androsten-17β-ol, and
16β-methyl-16α-fluoro-5-androsten 17α-ol drous sodium sulfate, and concentration to dryness in vacuo gave the crude oxime.

B. Beckmann Rearrangement of I.

Treatment of the crude oxime from 3.70 g of 20-one in 15 ml of pyridine with 3.75 g of p-acetamidobenzene-

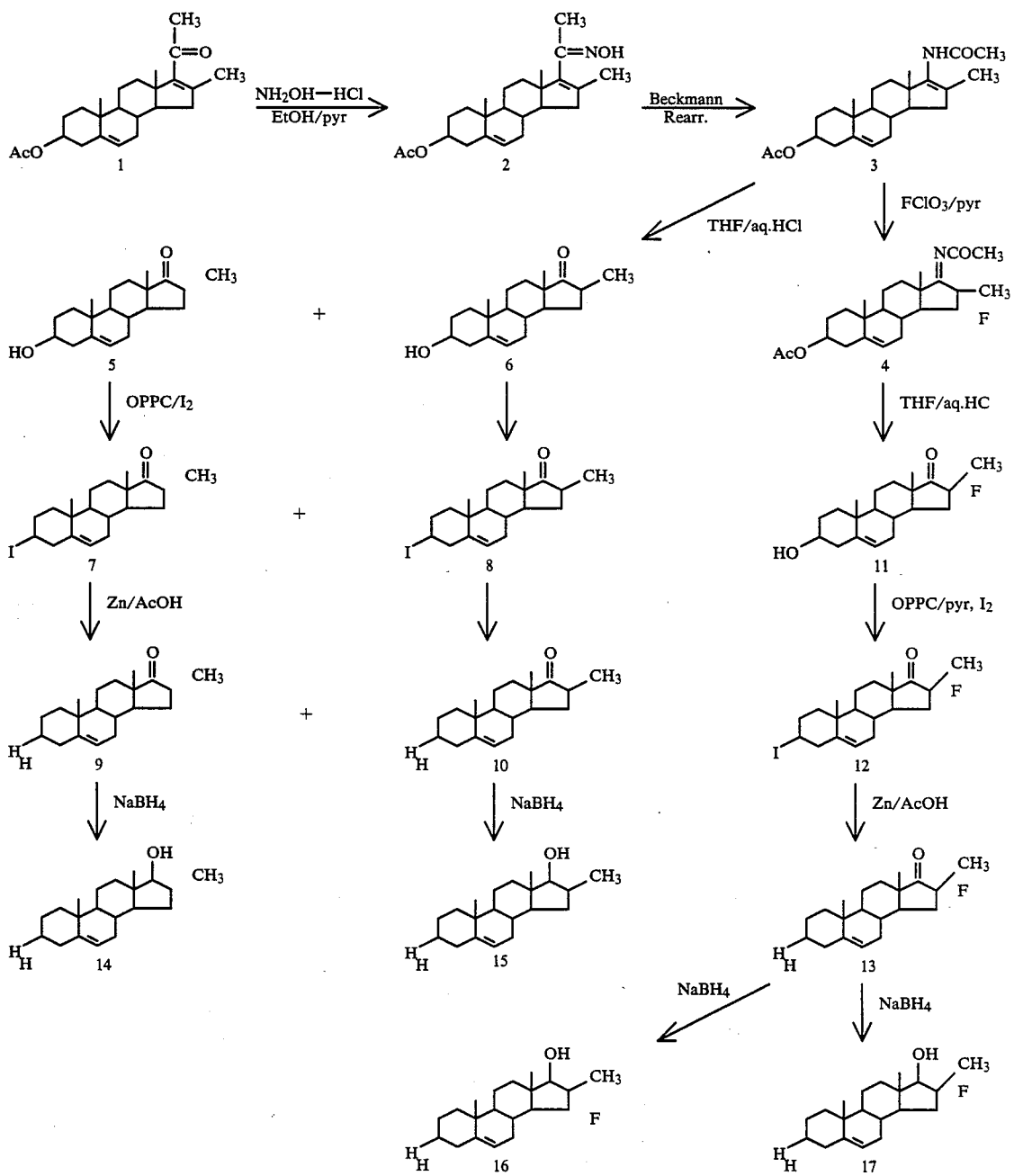

A. Preparation of 16-methyl-3-acetoxy-5,16-pregnadien-20-one-oxime (2).

A solution of 16-methyl-3β-acetoxy-5,16-pregnadien-20-one (3.70 g, 10 mmoles) was refluxed in a mixture of ethanol (100 ml) and pyridine (10 ml) containing 3.50 g (50 mmoles) of hydroxylamine hydrochloride for one hour. The reaction mixture was added to water and the crude product was filtered and washed with water. Solution in methylene chloride, filtration through anhysulfonyl chloride was carried out for 2 hours at 10°. The reaction mixture was added to ice water, furnishing a filterable solid which was washed thoroughly with water. The dried product was 17-acetamido-16-methyl-5,16-androstadien-3β-ol acetate (3), weighing 3.88 g.

C. Reaction of 3 with Perchloryl Fluoride/Pyridine.

A solution of the 16-methyl enamide acetate (1.94 g) in pyridine (100 ml) was treated with FClO₃ for 4 minutes as described in Example IB. The reaction mixture was added to ice water and cold, concentrated HCl was added until the reaction mixture has a pH 1. The resulting precipitate was filtered off and washed with water. The product was dissolved in methylene chloride and filtered through anhydrous sodium sulfate, affording the crude fluoro methyl enamide acetate (4).

D. Preparation of 16β-methyl-16α-fluoro-3-hydroxy-5-androsten-17-one (11).

A solution of (4) in tetrahydrofuran (100 ml) and water (100 ml) was refluxed in 10 ml of concentrated hydrochloride acid for 14 hours. The reaction mixture was partitioned between methylene chloride and water and the organic layer was filtered through anhydrous sodium sulfate. The crude hydroxy methyl fluoro ketone was subjected to preparative HPLC on a silica gel column in isopropyl alcohol/n-hexane. Crystallization of the major product from methanol gave long needles (420 mg, mp 177–180; 90 mg, mp 170–173). The mother liquor residue (350 mg) from the crystalline product was employed in the next step.

E. Preparation of 16-methyl-16-fluoro-5-androsten-17-one (13)

The crude 3-ol (4, 350 mg) from the previous step was added in 5 ml of methylene chloride to 5 ml of methylene chloride containing 90 μl of pyridine and 130 μl of 0-phenylenephosphorochloridite at 0° C. After standing for 2 hours at room temperature the crude phosphite was treated with 280 mg of iodine and the resulting mixture was stirred magnetically at room temperature for 2½ hours. The reaction mixture was washed successively with 1N NaOH (6 ml) and water (10 ml) filtered through sodium sulfate and dried. The crude 3-iodide (12) mixture (140 mg) was treated in 2 ml of acetic acid with 300 mg of zinc dust for 1 hour at 65°–70° C. After partitioning the reaction mixture between methylene chloride and water, the crude product was subjected to preparative HPLC on a silica gel column in ethyl acetate hexane.

A minor, more mobile product crystallized from aqueous acetone as platelets (12.5 mg), mp 122°–123°. Its infrared spectrum was consistent with a 16α-methyl-16β-fluoro-5-androsten-17-one structure. The major, less mobile product crystallized from methanol as needles (48.5 mg), mp 173°–175°. Its infrared spectrum was consistent with 16β-methyl-16α-fluoro-5-androsten-17-one (13).

F. Preparation of 16-α and 16β-methyl-5-androsten-17-ones

The crude methyl enamide acetate (1.94 g) was refluxed in 100 ml each of THF and water with 10 ml of concentrated HCl for 3½ hours. Following the usual work-up the crude hydroxy methyl ketones (5 and 6) were analyzed as the 3-acetates. In isooctane-ethyl acetate (21:4) there was a roughly 3:1 mixture of polar ($R_f$ 0.17) and mobile ($R_f$ 0.21) products, representing a mixture of the 16α-methyl and 16β-methyl-17-ones, respectively. Crystallization of the original 3-hydroxy mixture gave 425 mg of pure 16β-methyl-5-androsten-17-one (6), mp 168°–170°. The mother liquor residue (660 mg) represented a mixture of 16-α and 16β-methyl-3-hydroxy-17-ones (5 and 6). A solution of this mixture plus 6 ml of methylene chloride was added to 6 ml of methylene chloride containing 180 μl of pyridine and 260 μl of 0-phenylenephosphorochloridite at 0° C. and the mixture stood at room temperature for 2 hours. After addition of iodine (560 mg) to the crude phosphite, the reaction proceeded for 2½ hours at room temperature. The reaction mixture was washed with 10 ml of 1N NaOH and 10 ml of water. The mixture of iodides (7 and 8) was subjected to preparative HPLC on a silica gel column in ethyl acetate hexane. The more mobile product, designated 16α-methyl-3β-iodo-5-androsten-17-one (7) crystallized from methanol as needles (120 mg), mp 150°–151.5°.

λ max 1728 cm$^{-1}$ (16α-methyl-17-one) (See Noef, et al. JOC 43, 4579, 1978).

The less mobile product, designated 16β-methyl-3β-iodo-5-androsten-17-one (8) crystallized as needles (200 mg) from methanol, mp 151–153, λ max 1734 cm$^{-1}$ (16β-methyl-17-one according to Noef).

Treatment of 16α-methyl-3β-iodo-5-androsten-17-one (7) (90 mg) in 2.5 ml of acetic acid with 180 mg of zinc dust was carried out for one hour at 65°–70°. Crystallization of the product from aqueous acetone gave 40 mg of needles, mp 92°–95° C. Infrared analysis was consistent with 16α-methyl-5-androsten-17-one (9).

Treatment of 16β-methyl-3β-iodo-5-androsten-17-one (8, 200 mg) in 5 ml of acetic acid with 400 mg of zinc as in the preparation of 9 gave 95 mg of platelets from methanol, mp 102–103. IR analysis confirmed the 16β-methyl-5-androsten-17-one (10) structure.

G. 16α-methyl-5-androsten-17α-ol

Sodium borohydride is added to the 16α-method-5-androsten-17-one(produced in F hereinabove) according to the procedure described in Example 3 to form mostly the above-identified final product and a smaller amount of 16α-methyl-5-androsten-17β-ol, which are separated by HPLC or a silica gel column.

H. 16β-methyl-5-androsten-17β-ol

Sodium borohydride is added to the 16β-methly-5-androsten-17-one(produced in F hereinabove) according to the procedure described in Example 8F to form mostly the above-identified final product and a smaller amount of 16β-methly-5-androsten-17α-ol which are separated by HPLC on a silica gel column.

I. 16β-methyl-16α-fluoro-5-androsten-17βol and 16β-methyl 16α-fluoro-5-androsten-17αol Sodium borohydride is added to the product produced in E according to the procedure described in Example 8F afford the above-identified products.

EXAMPLE 12

Preparation of 16α Bromo-5-androstan-17α-ol and 16α Bromo-5α-androsten 17-β-ol

A. Method 1. Preparation of 3α-Iodo-5α-Androstan-17-one

Epiandrosterone (1.45 gms, 5 mmole) and 10 ml of THF was added to 0.41 ml of pyridine, 0.60 ml of 0-Phenylenephosphorochloridite and 10 ml of THF at 0° C. The mixture was stirred for two hours at room temperature. After filtering off the precipitated pyridinium chloride, the solvent was removed in vacuo, affording the crude phosphite ester. The residue was treated in 25 ml of methylene chloride with 1.27 grams (5.0 mmole) of iodine, and the mixture was stirred at room temperature for two and one half hours. Successive washings with 15 ml of 1N NaOH and water followed by filtration of the organic layer through anhydrous sodium thiosulfate afforded the crude 3α-iodide derivative. Crystallization from methanol combined with the HPLC of the mother liquor afforded a total of 0.82 grams of the above-identified product, melting point 124°–127°. Significant dehydrohalogenation by-products of the reaction were the 2-androstene-17-one and 3-androstene-17-one.

Method 2. Preparation of 3β-Iodo-5α-Androstan-17-one

To a solution of 1.6 g of epiandrosterone in 12 ml of pyridine was added 1.6 g of TsCl. The mixture stood for 13 hours at room temperature. After the addition of water, the product was extracted with methylene chloride. The organic layer was washed with cold dilute HCl, then water, affording a crude semi-crystalline tosylate. This material was refluxed in 100 ml acetone containing 10 grams of sodium iodide for 22 hours. The reaction mixture was partitioned between methylene chloride and water and the crude product was crystallized from methanol, yielding 920 mg of 3β Iodo-5-α-androstan-17-one opaque prisms, mp 147°–150° C. The TLC of the crystalline material and its mother liquor in isooctane ethyl acetate (22:3) showed the crystalline material to be homogenous. ($R_f$=0.16).

The material absorbed in the UV at 254 nm. (UV positive).

The mother liquor consisted of a ternary mixture, with the crystalline product being the most polar (lowest $R_f$). A second UV positive component with a similar $R_f$ ($R_f$=0.20) as the 3α-Iodide and a third (UV negative) more mobile component with a larger $R_f$ ($R_f$=0.25) as the olefinic mixture obtained in Method I were also isolated.

B. Preparation of 5α androstan-17-one

Method 1.

0.84 grams of the 3α-iodoantrostane-17-one in 25 ml of acetic acid was heated with 1.68 grams of zinc dust at 70°–75° for one hour with magnetic stirring. The reaction mixture was cooled, diluted with water and the crystalline precipitate resulting therefrom was filtered off and washed with water. The residue was leached with methylene chloride and the product was crystallized from aqueous methanol as platelets (480 mg) in a yield of 83.5%. Melting point 121°–121.5°. Similar reaction of 3β-iodo-5α-androstan-17-one with zinc in acetic acid, afforded 5α-androstan-17-one in comparable yields.

Method 2.

To a solution of 2.5 g of 5-androstene-17-one in 500 ml of ethanol was added 500 mg of 5% Pd on C and the mixture was exposed to a hydrogen atomsphere while stirring for 2.5 hours. The catalyst was filtered off and the residue from the filtrate had the same IR spectra as the material produced in B, Method 1.

C. 16α-Bromo-5-α-androstan-17-one 2.5 grams of the product from part B in 450 ml of methanol was refluxed with 6.06 grams (27.18 mmole) of CuBr$_2$ for 17½ hours. After the addition of an equal volume of water, the crystalline precipitate was filtered off and washed with water. Crystallization from methylene chloride/methanol gave 2.03 grams of the bromide as colorless prismatic needles, melting point 194°–196° (63% yield).

Alternatively, the above product may be prepared by catalytic hydrogenation over 5% palladium on carbon of 16α-Bromo-5-androsten-17-one, in accordance with the procedure in 12 B, Method 2 hereinabove.

D. 16αBromo-5α-androstan-17α-ol and 16αBromo-5α-androstan-17β-ol

METHOD 1.

Sodium borohydride is added to the product produced in C according to the procedure described in Example 8F to afford the above-identified final products.

METHOD 2.

Alternatively, catalytic hydrogenation over 5% palladium on carbon of the products produced in Example 9 in accordance with the procedure in B, Method 2 hereinabove affords the above-identified products.

EXAMPLE 13

16α-hydroxy-5α-androsten-17α-ol and 16α-hydroxy-5α-androsten-17β-ol

A. Preparation of 16α-hydroxy-5α-androstan-17-one

A solution of 16α-Bromo-5-androstan-17-one (706 mg, 2 mmole,), as prepared in accordance with the procedure in Example V, 60 ml of pyridine and 16 ml of water was treated with 3.6 ml (3.6 mmole) of 1N sodium hydroxide under oxygen. After stirring magnetically at room temperature for 15 minutes in an oxygen atmosphere, the clear yellow reaction mixture resulting thereform was added to ice water containing 66 ml of concentrated HCl. The product was extracted with methylene chloride and was crystallized as large prisms from methanol 375 mg, melting point 157°–158° C.

B. 16α-hydroxy-5αandrosten-17α-ol and 10α-hydroxy-5α-androstan-17β-ol

METHOD 1

Sodium borohydride treatment of the product produced in A according to the procedure described in Example 8F affords the above-identified products.

METHOD 2

Catalytically hydrogenation over 5% palladimon carbon of the products produced in Example 10 in accordance with the procedure of Example 12B, method 2 also affords the above-identified products.

EXAMPLE 14

16α-methyl-5α-androstan-17-α-ol,
16β-methyl-5α-androstan-17-β-ol,
16β-methyl-16α-fluoro-5α-androstan-17-β-ol and
16β-methyl-16α-fluoro-5α-androstan-17α-ol

METHOD 1

Catalytic hydrogenation one 5% palladium on carbon of the 16α-methyl-5 androsten-17α-ol produced in Example 11 in accordance with the procedure of Example 12B, Method 2 affords the 16α-methyl-5α-androstan-17α-ol.

Similarly, catalytic hydrogenation over 5% palladium on carbon of 16β-methyl-5-androsten-17β-ol, 16β-methyl-16α-fluoro-5-androsten-17β-ol and 16β-methyl-16α-fluoro-5-androsten-17α-ol produced in Example 5 affords 16β-methyl-5α-androstan-17-β-ol, 16β-methly-16α-fluoro-5α-androstan-17β-ol, and 16β-methyl-16α-fluoro-5α-androstan-17α-ol, respectively.

METHOD 2

Catalytic hydrogenation over 5% palladium on carbon of the 16α-methly-5-androsten-17-one produced in Example 5 in accordance with the procedure of Example 12B, Method 2 followed by treatment with sodium borohydride also affords 16α-methyl-5-androstan-17α-ol and 16α-methyl-5α-androstan-17-β-ol.

Similarly, catalytic hydrogenation over 5% palladium on carbon of the 16β-methyl-5-androsten-17-one produced in Example 5 followed by treatment with sodium borohydride affords 16β-methyl-5α-androstan-17α-ol and 16β-methyl-5α-androstan-17β-ol.

Similary, catalytic hydrogenation over 5% palladium on carbon of the 16β-methyl-16α-fluoro-5-androsten-17-one produced in Example 5 followed by treatment with sodium borohydrid affords 16β-methyl-16α-fluoro-5α-androstan-17α-ol and 16β-methyl-16α-fluoro-5α-androstan-17β-ol.

EXAMPLE 15

16α-fluoro-5α-androstan-17α-ol and
α-fluoro-5α-androstan-17-β-ol

A. Preparation of 16α-fluoro-5-αandrostan-17

Method 1

To a stirred solution of 500 mg of 16α-Bromo-5-androstan-17-one, prepared in accordance with the procedure of Example 12, in 10 ml of DMSO was added 500 mg of 18-crown-6 ether and 1500 mg of KF. The solution was heated to 85°-90°. After 6 hours, the mixture was partitioned between methylene chloride and water and was subjected to HPLC in an ethyl acetate-hexane gradient system. Crystallization from methanol of the more mobile component gave 23 mg of starting material (melting pint 188°-190° C.). Crystallization from methanol of the less mobile component gave 41 mg of plates, the IR of which is consistent with the final product.

Method 2

250 mg of 16βfluoro-5-α-androsten-17-one in 50 ml of ethanol was treated with 50 mg of 5% palladium on carbon and hydrogen gas for 2½ hours. The reaction mixture, as indicated by the IR, is compatible with 16β-fluoro-5α-androstan-17-one. This crude product was treated with 5 ml methanol and 5 ml of 1N methanolic KOH for one hour. The mixture was partitioned between methylene chloride and water and subjected to HPLC as indicated above. Crystallization of the less mobile component from methanol gave 30 mg of 16α-fluoro-5α-androstan-17-one as prismatic needles, melting point 148°-150° C.

Method 3

To a solution of 16α-fluoro-5α-androstene-17-one (1100 mg) in ethanol (220 ml) was added 220 mg of 5% Pd on carbon. The mixture was stirred in a hydrogen atmosphere for 1 hour at room temperature. The catalyst was filtered off and washed with ethanol. The residue from the combined filtrate was recrystallized from methanol, giving 770 mg, m.p. 146°-148.5° C. The IR spectrum was identical with that of 16α-fluoro-5-α-androstan-17-one prepared hereinabove.

B. 16α-fluoro-5α-androstan-17α-ol and
16α-fluoro-5α-androstan-17β-ol

METHOD 1

Sodium borohydride is added to the product produced in A according to the procedure described in Example 8F to afford the above-identified final products.

METHOD 2

Catalytic hydrogenation over 5% palladium on carbon of the products formed in Example 8 in accordance with the procedure of Example 12B, Method 2 affords the above-identified products.

EXAMPLE 16

A. 3β,16β-dimethylandrost-5-en-17-one

To a solution of 16β-methyl-3β-hydroxy-5,16-pregnadien-20-one was added toluene, ethylene glycol, and p-toluene-sulfonic acid. The resulting solution was refluxed overnight forming the 20-ketal. The procedure for this ketalization step is described in *JACS*, 76, 5674 (1954). Tosyl chloride in pyridine was added to the above product to form the 3β-tosylate derivative. The 3β-tosylate was refluxed overnight with 10% NaI/acetone to form the 3β-iodo-16-methyl-5,16-pregnadien-20-one-ethylene ketal. This product was methylated with lithium dimethylcuprate in ether and tetrahydrofuran at −78° C. under a nitrogen atmosphere to form the 3β,16-dimethyl-5,16-pregnadien-20-one ethylene ketal. This product was deketalized by refluxing in the presence of acetone/p-toluenesulfonic acid. The resulting 3β,16-dimethyl,5,16-pregnadien-20-one was converted to the C-20-oxime by refluxing in ethanol and pyridine with an excess of hydroxylamine hydrochloride. This product was subjected to a Beckmann rearrangement in the presence of p-acetamidobenzenesulfonyl chloride/pyridine according to the procedure by Rosenkranz, et al. in *J. Org. Chem.*, 21, 520–522 (1956). The product, 17-acetamido-3β,16-dimethyl-5,16-androstadiene was refluxed in tetrahydrofuran/hydrochloric acid solution. 3β,16β-dimethyl-5-androst-en-17-one was formed, separated and purified by normal phase HPLC using a 1 in. ×25 cm silica gel preparative column at a flow rate of 30 ml/min and using ethyl acetate/hexane (in a gradient ranging from 0 to 20%) as the eluent. The product was recrystallized from methanol and characterized by NMR and IR.

B. Sodium biohydride reduction of the product of A affords, 3β,16β-dimethyl-5-androsten-17-α-ol and 3β,16β-dimethyl-5-androsten-17-β-ol.

C. Catalytic hydrogenation of the products in B. affords 3β,16β-dimethyl-5-androsten-17α-ol and 3β, 16β-dimethyl-5α-androstan-17β-ol.

EXAMPLE 16A

A. 3β-methyl-16α-fluoro-5-androsten-17-one

Starting from 3β-hydroxy-5,16 pregnadien-20-one and following the procedure of Example 16, the 20-oxime of 3β-methyl-5,16 pregnadien-20-one was formed. Beckmann rearrangement of this product in the presence of p-acetamidobenzenesulfonyl chloride/pyridine according to the procedure by Rosenkranz, et al. in *J. Org. Chem.* 21, 520–522 (1956) followed by treatment of the resulting enamide with perchloryl fluoride and acid hydrolysis affords the above-identified product.

B. 3β-methyl-16α-fluoro-5-androsten-17α-ol and
3β-methyl-16α-fluoro-5-androsten-17β-ol The above products are prepared by sodium borohydride treatment of the product produced in A.

EXAMPLE 17

16α-fluoro-3β,16β-dimethyl-5-androsten-17α-ol; and
16α-fluoro-3β,16β-dimethyl-5-androsten-17-β-ol A. 16α-fluoro-3β,16β-dimethyl-5-androst-en-17-one The procedure is identical to the formation of 3-βmethyl-16α-fluoro-androst-5-en-17-one except that the starting material is 3β,16-dimethyl-5,16-pregnadien-20-one. The final product which was purified by normal phase HPLC using ethylacetate-hexane as eluent, and recrystallized from methanol, formed a colorless crystal which melted at 129°–130° C.

B. 16α-fluoro-3β,16β-dimethyl-5-androsten-17α-ol and 16α-fluoro-3β,16β-dimethyl-5-androsten-17β-ol Treatment of the product formed in A hereinabove this above-identified product.

EXAMPLE 18

16α-bromo-3β-methyl-5-androsten-17α-ol and
16α-bromo-3β-methyl-5-androsten-17β-ol A. 16α-bromo-3β-methyl-5-androsten-17-one 3β-methyl-5-androsten-17-one (4.0 g, 14 mmol) and $CuBr_2$ (9.4 g, 4.2 mmol) were dissolved in methanol (250 ml) and refluxed for 24 hours. The hot solution was filtered to remove the white precipitate and the filtrate was cooled to yield 3.1 g (61%) of 16α-bromo-3β-methylandrost-5-en-17-one. An analytical sample was prepared by passing an ether solution of the steroid through a small plug of neutral alumina. Evaporation and recrystallization from methanol gave white needles: mp 193°–195° C.; NMR ($CDCl_3$) δ 5.30 (br.d, 1H, H-6), 4.52 (t, 1H, 16β-H), 0.98 (s, 3H, C-19-Me), 0.90 (s, 3H, C-18 Me); IR (KBr) 2910, 1735, 1445, 1365, 1020; MS: 366 (M+, 100), 364 (96), 351 (75), 349 (70), 285 (35), 283 (44), 282 (23), 281 (46), 267 (25); Anal. Calcd for $C_{20}H_{29}OBr$:C, 65.70; H, 8.00. Found C, 65.54, H, 8.11.

B. 16α-bromo-3β-methyl-5-androsten-17α-ol and
16α-bromo-3β-methyl-5-anrosten-17β-ol Treatment of the product produced in with sodium borohydride affords the above-identified products.

EXAMPLE 19

16β-bromo-3β-methyl-5-androsten-17α-ol and
16β-bromo-3β-methyl-5-androsten-17β-ol A. 16β-bromo-3β-methyl-5-androsten-17-one The 16α-bromo derivative (365 mg, 1 mmole) that was formed in Example 18 was refluxed in 10 ml isopropanol and 30 ml toluene 635 mg (5 mmole) of AgF for 18 hours. The reaction mixture was washed with brine and filtered through anhydrous $Na_2SO_4$ and dried. The reaction mixture was subjected to preparative HPLC on a silica gel column. The most mobile product was obtained as platelets from $CH_3OH$ in a yield of 130 mg m.p. 186°–188°.

B. 16β-bromo-3β-methyl-5-androsten-17α-ol and
16β-bromo-3β-methyl-5-androsten-17β-ol The above products are prepared by treating the product formed in A with sodium borohydride.

EXAMPLE 20

3β,16β-dimethyl-5-androsten-17α-ol and
3β,16β-dimethyl-5-androsten-17β-ol

Treatment of the product formed in A of Example 16 with sodium borohydride affords the above-identified products.

EXAMPLE 21

3β,16β-dimethyl-5-α-androstan-17-α and
3β,16β-dimethyl-5α-androstan-17β-ol

To a solution of 3β,16β-dimethylandrost-5-en-17-α-ol or 3β,16β-dimethyl-5-androstan-17β-ol in 500 ml of ethanol is added 5% Pd on C and the mixture is exposed to a hydrogen atmosphere while stirring. The catalyst is filtered off and the above-identified product is isolated.

Similarly, using the appropriate starting materials the following compounds are prepared:
3β-methyl-16αfluoro-5α-androstan-17α-ol
16αfluoro-3β,16β-dimethyl-5α-androstan-17α-ol
3β-methyl-16α-hydroxy-5α-androstan-17-α-ol
3β,16β-dimethyl-16β-bromo-5α-androstan-17α-ol
3β-methyl-16α-fluoro-5α-androstan-17β-ol
16α-fluoro-3β,16β-dimethyl-5α-androstan-17β-ol
3β-methyl-16α-hydroxy-5α-androstan-17β-ol
3β,16β-dimethyl-16α-bromo-5-α-androstan-17β-ol
3β,16β-dimethyl-16α-bromo-5-α-androstan-17β-ol

EXAMPLE 22

A. 3β-methyl-16α-chloro-5-androsten-17-one 800 mg of 3β-methyl-16β-trifluoromethylsulfonyloxy-5-androsten-17-one, prepared from 3β-methyl-16β-hydroxy-5-androsten-17-one and trifluoromethane sulfonic acid was placed in 16 ml DMF and was treated with 100 mg Lithium chloride at room temperature. The reaction mixture was stirred magnetically for 21 hours. Water is then added and the resulting crystalline ppt was collected. The crystals were washed with additional water and were then dissolved in $CH_2Cl_2$, filtered through anhydrous sodium sulfate and the solvent was evaporated off. The resulting crystals were recrystallized from $CH_3OH$, yielding 570 mg of final product. m.p. 159°–165° C.

B. 3β-methyl-16α-chloro-5α-androsten-17-α-ol and
3β-methly-16α-chloro-5α-androsten-17β-ol Treatment of the product formed in A with sodium borohydride affords the above-identified product.

C. 3β-methly-16α-chloro-5α-androstan-17α-ol and
3β-methyl-16α-chloro-5α-androstan-17β-ol To a solution of the products formed in B in 500 ml of ethanol is added 5% Pd or C and the mixture is exposed to a hydrogen atmosphere while stiring. The catalyst is filtered off and the desired products are isolated.

A. 16α,16β-difluoro-3β-methyl-5-androsten-17-one

Formylation of 3-methyl-5-androsten-17-one using the procedure of C. H. Robinson, et al., J. Org. Chem. 28, 975 (1963) gives the corresponding 16-hydroxymethylenes. Fluorination of the hydroxy methylene-17-one in a t-butyl alcohol/potassium t-butoxide system (six moles of butoxide per mole of steroid) with perchloryl fluoride, according to the procedure of Robinson, et al., JOC 28, 975, 1963, affords the 16, 16-difluoro-3β-methyl-5-androsten-17-one.

B. 16α,16β-difluoro-3β-methly-5-androsten-17α-ol and 16α,16β-difluoro-3β-methyl-5α-androsten-17β-ol Treatment of the products formed in A with sodium borohydride affords the above-identified products.

EXAMPLE 24

16α,16β-difluoro-3β-methyl-5α-androstan-17-α-ol and 16α-,16β-difluoro-3β-methyl-5α-androstan-17β-ol Using the procedure of Example 22C, the products of B are catalytically hydrogenated to afford the above-identified products.

EXAMPLE 25

A. 3β,16,16-Trimethyl-5-Androsten-17-one

Treatment of 3β-methyl-5-androsten-17-one in t-butyl alcohol and potassium t-butoxide with excess methyl iodide gives the above identified product.

B. 3β,16,16-Trimethyl-5α-androsten-17α-ol and 3β,16,16-Trimethyl-5α-androsten-17β-ol Treatment of the product produced in A with sodium borohydride affords the above-identified products.

EXAMPLE 26

A. 3β,16,16-Trimethyl-5α-Androstan-17-one

Treatment of 3β-methyl-5-androstan-17-one in t-butyl alcohol and potassium t-butoxide with excess methyl iodide gives the above-identified product.

B. 3β,16,16-Trimethyl-5α-Androstan-17α-ol and 3β,16,16-Trimethyl-5α-androstan-17β-ol Treatment of the above product in A with sodium borohydride affords the above-identified products

EXAMPLE 27

A.
6β-Bromo-17β-hydroxy-4-methylandrost-4-en-3-one 4-methyltestosterone (1 g, 3.31 mmol), N-bromosuccinimide (0.589 g, 3.31 mmol) and benzoyl peroxide (20 mg) were refluxed in dry carbon tetrachloride (50 ml) for 15 min. The reaction mixture was then cooled to 0° C. and the precipitated material was separated by filtration. The filtrate was washed with 5% sodium bicarbonate, then water and the organic layer was then dried and the solvent removed to give 6β-bromo-4-methylandrost-4-en-3-one, m.p. 124°–125° C., H NMR:δ5.4 (m, 1H), 3.68 (t, 3H), 1.86 (s, 3H), 1.52 (s, 3H), 0.85 (s, 3H).

B. 4α-methylandrost-5-en-3β,17β-diol

The 6β-bromide (190 mg, 0.5 mmol) was added to a solution of Red-Al (300 eq) in toluene (40 ml). The reaction mixture was stirred at 80° C. for 24 hours, cooled to 0° C. and sodium hydroxide (20 ml of a 20% sol.) was added slowly. The mixture was extracted with ethyl acetate (2×100 ml), and the organic layer washed with water, and then brine. The organic layer was then dried, and evaporated to yield 4α-methylandrost-5-en-3β,17β-diol, m.p. 210°–214° C. IR:3500 cm$^{-1}$ (OH strong), no C=O. M.S. m/e 304.2 (100%), 286 (52), 271 (38), 105(35).

Similar results were obtained when the 6β-bromide was reduced with a large excess of LAH (80 mmol) using ether as a solvent.

C. 3β-Hydroxy-4α-methylandrost-5-en-17-one

To the diol formed in B above, (0.723 g, 2.38 mmol) dissolved in dimethylformamide (140 ml) was added manganese dioxide and the mixture stirred for four days. The maganese dioxide was filtered off and ethyl acetate added to the filtrate. The organic layer was washed with aqueous sodium bicarbonate, brine, and dried. Evaporation of the solvents followed by intensive chromatography of the residue over silica gel afforded 3β-hydroxy-4α-methylandrost-5-en-17-one. IR 3493 (OH), 1745 (C=O), $^1$H NMR (CDCl$_3$): δ5.64 (m, 1H, H-6), 3.06 (m, 1H,H-3α), 1.72 (bis, 4 CH$_3$), 1.07 (s, 3H, 19-CH$_3$) 0.89 (s, 3H, 18-CH$_3$). M.W., calculated for C$_{20}$H$_{30}$O$_2$=302.2247; Found 302.2242.

D. 3β-hydroxy-4α-methly-5-androsten-17α-ol and 3β-hydroxy-4α-methly-5-androsten-17β-ol Treatment of the products in C with sodium borohydride affords the above-identified products.

E. 3β-hydroxy-4α-methyl-5α-androstan-17α-ol and 3β-hydroxy-4α-methyl-5α-androstan-17β-ol Catalytic hydrogenation of the product formed in D according to the procedure of Example 21 affords the above-identified products

EXAMPLE 28

A. 3,17β-Dihydroxy-1α-methylandrosta-3,5-diene diacetate

17β-Hydroxy-1α-methylandrost-4-en-3-one (1α-methyltestosterone, 1.0 g, 3.3 mmol) was dissolved in pyridine (10 ml) and acetic anhydride (10 ml) and stirred at room temperature under a drying tube for 18 hours. The mixture was poured into cold water and the precipitate collected and washed with additional cold water. After drying, the solid was chromatographed on flash SiO$_2$ and eluted with 5% ether - 95% hexane. There was obtained 1.18 g (93%) of 3,17β-dihydroxy-1α-methylandrosta-3,5-diene diactate 51, which was recrystallized from methanol-water: mp 111°–112° C.; NMR (CDCl$_3$) δ5.65 (d, J=3 Hz, 1H, H-4), 5.52 (br s, 1H, H-6), 4.64 (t, 1H, H-17), 2.10 (s, 3H, Ac), 2.02 (s, 3H, Ac), 1.05 (s, 3H, C-18 Me), 0.83 (s, 3H, C-19 Me), 0.86 (d, 3H, C-1 Me); IR (KBr) 2910, 1745, 1730, 1360, 1245, 1215; MS 386 (M+, 4), 358(1) ), 344(100), 329(2), 315M* (344–329), 301(1), 151(1), 43(13); Anal. Calcd for C$_{24}$H$_{34}$O$_4$: C, 74.57; H, 8.86. Found: C, 74.39; H, 8.62.

B.
3α,17β-Dihydroxy-1α-methylandrost-5-en-17-acetate

The diacetate formed hereinabove (1.00 g, 2.67 mmol) was dissolved in 95% ethanol (100 ml). Sodium borohydride (1.00 g, 26.3 mmol) was added and the mixture stirred at room temperature under a drying tube for 8 hours. Acetic acid (1.5 ml) was carefully added and the solution was evaporated to dryness. The solid was taken up in methylene chloride (30 ml) and washed with dilute hydrochloric acid, water, then dried over magnesium sulfate, filtered, evaporated, and chromatographed on flash SiO$_2$. Elution with 10% ethyl acetate - 90% hexane gave 465 mg (52%) of 3α,17β-dihydroxy-1α-methylandrost-5-en-17-acetate: NMR (CDCl$_3$) δ5.51 (br d, 1H, H-6), 4.61 (t, 1H, H-17), 4.04 (br s, 1H, OH), 2.01 (s, 3H, Ac), 1.08 (s, 3H, C-18 Me), 0.79 (d, J=4 Hz, 3H, C-1 Me), 0.81 (s, 3H, C-19 Me); IR (KBr), 3400, 2890, 1725, 1360, 1245, 1035; MS 346 (M+, 26), 328(77), 313(12), 286(12), 262(10), 253(14), 202(11), 43(100); Anal. Calcd for $C_{22}H_{34}O_3$: C, 76.26; H, 9.89. Found: C, 76.08; H, 9.72.

C. 3α,17β-Dihydroxy-1α-methylandrost-5-en-3-t-butyldimethylsilyl-17-acetate

3α,17β-Dihydroxy-1α-methylandrost-5-en-17-acetate formed hereinabove (3.4 g, 0.98 mmol) was dissolved in freshly distilled dimethylformamide (10 ml). Imidazole (0.61 g) and tert-butyldimethylsilyl chloride (0.77 g, 5.1 mmol) were added and the mixture stirred for 18 hours at room temperature. Water (30 ml) was added and the solution extracted with ether (2×100 ml). The combined organic layers were dried over magnesium sulfate, filtered, and evaporated to dryness to afford 0.44 g (97%) of 3α,17β-dihydroxy-1α-methylandrost-5-en-3-t-butyldimethylsilyl-17-acetate: NMR (CDCl$_3$) δ5.38 (br d, 1H, H-6), 4.60 (t, 1H, H-17), 3.91 (s, 1H, H-3), 2.01 (s, 3H, 17-Ac), 1.05 (s, 3H, C-19 Me), 0.91 (s, 9H, t-Bu), 1.06 (s, 3H, C-18 Me), 0.80 (d, J=4 Hz, 3H, C-1 Me); IR (KBr) 2950, 1740, 1460, 1365, 1250, 1055; MS 460 (M+, 16), 445(3), 403(100), 343(6), 327(35), 269(17), 199(17), 142(34); Anal. Calcd for $C_{28}H_4O_3Si$: C, 72.99; H, 10.50. Found: C, 73.17; H, 10.48.

D. 3α,17β-Dihydroxy-1α-methylandrost-5-en-3-t-butyldimethylsilyl ether

3α,17β-Dihydroxy-1α-methylandrost-5-en-3-t-butyldimethylsilyl-17-acetate formed hereinabove (0.44 g, 0.95 mmol) was dissolved in tetrahydrofuran (5 ml), methanol (20 ml), water (5 ml) and potassium bicarbonate (1 g) and refluxed for 18 hours. The solution was filtered, evaporated to dryness, taken up in chloroform (20 ml) and washed with dilute hydrochloric acid and then water. The organic layer was dried over magnesium sulfate, filtered and evaporated to give 3α,17β-dihydroxy-1α-methylandrost-5-en-3-t-butyldimethylsilyl ether, 0.39 g (97%): mp 126°-127° C.; NMR (CDCl$_3$) δ5.39 (br s, 1H, H-6), 4.01 (br s, 1H, H-3β), 3.57 (t, 1H, H-17), 1.12 (s, 3H, C-19 Me), 0.92 (s, 9H, t-butyl), 1.10 (s, 3H, C-18 Me), 0.79 (d, 3H, C-1 Me); IR (KBr) 3420, 2920, 1460, 1250, 1050; MS 418 (M+, 3), 403(2), 361(100), 343(3), 286(63), 271(10), 253(9); Anal. Calcd for $C_{26}H_{46}O_2Si$: C, 74.58; H, 11.07. Found: C, 74.36; H, 11.29.

E. 3α-Hydroxy-1α-methylandrost-5-en-17-one

3α,17β-Dihydroxy-1α-methylandrost-5-en-3-t-butyldimethylsilyl ether formed hereinabove (0.20 g, 0.478 mmol) and sodium acetate (20 mg, 0.24 mmol) were dissolved in dry methylene chloride (15 ml). Pyridinium chlorochromate (0.3 g, 1.43 mmol) was added in one portion and the mixture stirred for 2 hours. The solution was diluted with ether (30 ml) and passed through a small plug of florisil. Evaporation of the solvent gave 200 mg (100%) of 3α-hydroxy-1α-methylandrost-5-en-17-on-3-tertbutyldimethyl silyl ether which was used without further purification. Several runs were combined. This compound (1.1 g, 2.64 mmol) was dissolved in dry tetrahydrofuran (20 ml) tetra n-butylammonium fluoride (8.0 ml, 7.9 mmol) was added and the solution stirred for 2 hours. An additional portion (5.0 ml) of (n-Bu)$_4$NF was added and the solution refluxed for 48 hours. Water (60 ml) was added and the mixture extracted with ethyl acetate (100 ml). The organic layer was separated, dried, filtered and evaporated. The residue was chromatographed on SiO$_2$ and eluted with 5% ether - 95% hexane. There was obtained 0.64 g (80%) of 3α-hydroxy-1α-methylandrost-5-en-17-one: mp 167°-169° C.; NMR (CDCl$_3$) δ5.55 (br s, 1H, H-6), 4.07 (br s, 1H, H-3β), 1.11 (s, 3H, C-18 Me), 0.89 (s, 3H, C-19 Me), 0.81 (s, 3H, C-1 Me); IR (KBr) 3460, 2930, 1715, 1450, 1360; Anal. Calcd for $C_{20}H_{30}O_2$: C, 79.42; H, 9.99. Found: C, 79.18; H, 10.17.

F. 3α-hydroxy-1α-methyl-5-androsten-17α-ol and 3α-hydroxy-1α-methyl-5-androsten-17β-ol Treatment of the products formed in E with Sodium borohydride forms the above-identified products.

G. 3α-hydroxy-1α-methyl-5α-androstan-17α-ol and 3α-hydroxy-1α-methyl-5α-androstan-17β-ol Catalytic hydrogenation of the product formed in F in accordance with the procedure described in Example 21 affords the above-identified product.

EXAMPLE 29

16αHydroxy-3β-methylandrost-5-en-17-one

16α-Bromo-3β-methylandrost-5-en-17-one (1.00 g, 2.74 mmol) was dissolved in dimethylformamide (90 mL). Sodium hydroxide (165 mg, 4.1 mmol) in water (10 mL) was added and the solution stirred for 2 h. at room temperature. The solution was poured into 1% HCl (200 mL) and extracted with ethyl acetate (2×50 mL). The organic layer was washed with 5% sodium biocarbonate, water, then dried over magnesium sulfate and filtered. Evaporation gave a pale yellow solid which was chromatographed on flash silica gel and eluted with ether/hexane (10/90). Recrystallization from ether gave 0.54 g (65%) 16α-hydroxy-3β-methylandrost-5-en-17-one mp 166°-168° C.; NMR (DMSO-d$_6$) δ5.30 (br s, 1H, H-3), 4.38 (t, 1H, 16β-H), 2.0-1.05 (m, complex), 0.98 (s, 3H, C-19 Me), 0.95 (d, J=8 Hz, 3H, C-3 Me), 0.87 (s, 3H, C-18 Me); IR (KBr) 3440, 2900, 1735, 1445, 1365, 1010; MS 302 (M+,100), 287(24), 274(7), 259(7), 241(7), 230(72), 215(41), 159(31); Anal. Calcd for $C_{20}H_{30}O_2$: C, 79.42; H, 9.99. Found: C, 79.24; H, 10.04.

B. 16α-hydroxy-3β-methyl-5-androsten-17αol and 16αhydroxy-3β-methyl-5androsten-17β-ol Treatment of the product formed in A with sodium borohydride affords the above-identified products.

C. 16α-hydroxy-3βmethyl-5α-androstan-17α-ol and 16α-hydroxy-3β-methyl-5αandrostan-17β-ol Catalytic hydrogenation of the product formed in B according to the procedure of Example 21 affords the above-identified products.

EXAMPLE 30

A. 3β-16α-Dimethylandrost-5-en-17-one

Diisopropyl amine (1.165 g, 11.5 mmol) was dissolved in dry tetrahydrofuran (30 mL) at −78° C. under N$_2$. n-Butyl lithium (4.44 mL of a 2.6 M solution in hexane, 11.5 mmol) was added via syringe and the solution warmed to −23° C. (CO$_2$, CCl$_4$) for 0.25 h. 3β-Methylandrost-5-en-17-one (3.0 g, 10.4 mmol) in dry tetrahydrofuran (30 mL) was added via syringe and the solution stirred for 0.25 h. Methyl iodide (7.0 g, 49.33 mmol) in dry tetrahydrofuran (30 mL) was added dropwise and the mixture stirred at room temperature for 1.5 h. The solution was quenched with saturated ammonium chloride and the organic layer separated, dried over magnesium sulfate, filtered, and evaporated. The residual solid was chromatographed on flash silica gel (120 g) and eluted with 1/99 (v/v) ether hexane to give 3β, 16α-dimethylandrost-5-en-17-one (2.32 g, 74%). mp 109°–110° C. (recrystallized from methanol); NMR (CDCl$_3$) δ5.29 (br s, J=5 Hz, 1H, H-6), 2.52 (m, 1-H, H-16), 1.07 (d J=8 Hz, 3H, C-16 Me), 0.99 (s, 3H, C-19 Me), 0.91 (s, 3H, C-18 Me); IR (KBr) 2900, 1730, 1450, 1430, 1370; MS 300 (M+,100), 285(62), 282(2), 272(12), 267(17), 229(20), 217(30), 159(17); Anal. Calcd for C$_{21}$H$_{32}$O: C, 83.93; H, 10.73. Found: C, 83.79; H, 10.52.

B. 3β, 16α-dimethyl-5-androsten-17α-ol and 3β, 16α-dimethyl-5-androsten-17β-ol

Treatment of the product formed in A with sodium borohydride affords the above-identified products.

C. 3β, 16α-dimethyl-5α-androstan-17α-ol and 3β, 16α-dimethyl-5α-androstan-17β-ol Catalytic hydrogenation of the product formed in B in accordance with the procedure of Example 21 affords the above-identified products.

EXAMPLE 31

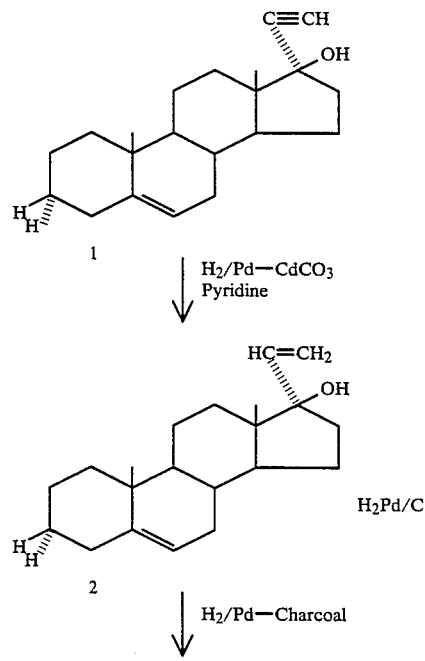

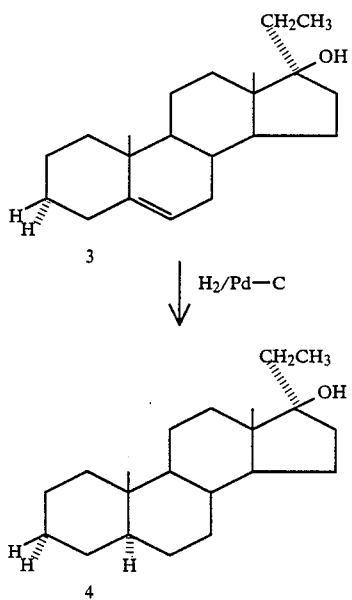

Using the procedure of Hershberg, et al JACS 73, 5073 (1951), 4 can be prepared. More specifically, selective hydrogenation of 17αethinyl-5-androsten-17β-ol (1) in pyridine with 5% palladium on Calcium Carbonate affords the vinyl carbinol (2) in high yield. Reduction of 2 in ethanol with 5% palladium on carbon gives the ethyl carbinol 3 without reducing the 5, 6-double bond. Alternatively, 3 can be prepared directly from 1 using H$_2$/Pd/C. Exhaustive Catalytic hydrogenation of 3 in ethanol with 5% Pd on C gives the fully saturated pregnanol, 4

Similarly, using the procedure hereinabove, and starting with the appropriate starting materials, the following compounds can also be prepared:

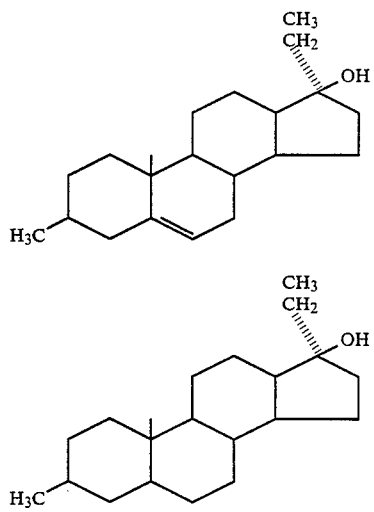

A compound's efficacy in the inhibition of mammalian glucose 6-phosphate dehydrogenase (G6 PDH inhibition) is an accurate indicator of its cancer prophylatic activity. The assay for testing the inhibition of purified bovine adrenal G6PDH is described by Oertel, G. W.

and Rebebun, F., in *Biochem. Biophys. Acta,* 184, 459–460 (1969).

Compounds of the present invention are effective in the prophylaxis treatment of cancer. It has been shown that compounds of this sort are effective inhibitors of G6PDGH dehydrogenase.

The results of representative compounds are shown below:

| COMPOUND | CONC. | PERCENT G6PDH INHIBITION |
|---|---|---|
| DHEA | $10^{-5}$ M | 50, 49 |
|  | $10^{-6}$ M | 28, 30 |
| 16α-fluoro-5-androsten-17β-ol | $10^{-5}$ M | 16, 24 |
| 16α-fluoro-5-androsten-17β-ol | $10^{-5}$ M | 42, 43 |
|  | $10^{-6}$ M | 11, 6 |

Compounds of the present invention are also effective in the prophylaxis and treatment of obesity. In fact, the compounds wherein the B ring of the steroid contains a double bond in the 5,6 position are more effective with respect to obesity than the saturated counterpart, which has some effectiveness in the obesity test.

The compounds of the present invention are also effective anti-hyperglycemic agents, anti-hypercholesterolemic agents and anti-aging agents both with respect to the prophylaxis and treatment of said diseases, conditions and disorders. Moreover, the compounds of the present invention are effective anti-auto-immune agents, and are effective in the prophylaxis and treatment of auto-immune diseases such as lupus erythematosis and Coomb's positive hemolytic anemia.

The compounds of the present invention do not possess the side effects that are exhibited by other steroids. Unlike other steroids such as DHEA, the compounds of the present invention do not exhibit an estrogen effect. Furthermore, the compounds of the present invention do not exhibit liver enlargement, which is prevalent with other steroids, such as DHEA.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. For parental administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages, substantially less than the optimum dose of the compound and increase the dosage by small increments until the optimum effect under the circumstances is reached.

It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with those other therapeutic agents.

When given orally, the therapeutic doses of the compounds of the present invention are generally in the range of from about 4 to about 450 mg/kg/day depending upon the particular mammalian host and the particular effect desired, e.g. cancer preventive, anti-obesity, anti-diabetes, etc. When given parenterally, the compounds are administered generally in dosages of, for example, 0.5 to about 15 mg/kg/day, also depending upon the host and effect desired.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils, The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Obviously, other modifications and variations of the present invention are possible in light of the above teachings. It is, therefore, to be understood that changes may be made in the particular embodiments of this invention which are within the full intended scope of the invention as defined by the appended claims.

What is claimed is:

1. Compounds of the formulae:

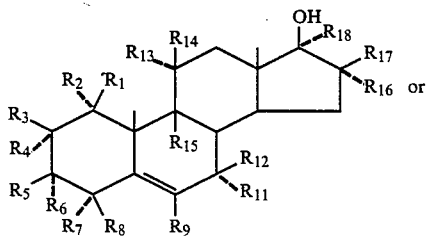

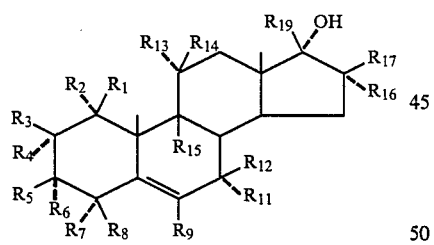

wherein
$R_1$, $R_2$, $R_3$, $R_4$, $R_7$, $R_8$, $R_{11}$, $R_{12}$, $R_{13}$, $R_{14}$, $R_{15}$, and $R_{17}$ are each independently hydrogen, lower alkyl, halogen, or lower alkoxy; $R_5$ and $R_6$ are independently hydrogen, lower alkyl or lower alkoxy;
$R_{16}$ is lower alkyl, halogen, or lower alkoxy;
$R_9$ is hydrogen, lower alkyl or halogen; and
$R_{18}$ and $R_{19}$ are each independently hydrogen, lower alkyl, lower alkenyl, lower alkynyl, formyl, lower alkanoyl or epoxy.

2. The compound according to claim 1 wherein the lower alkyl and lower alkoxy group contain 1-3 carbon atoms.

3. The compound according to claim 1 wherein lower alkyl is methyl.

4. The compound according to claim 1 wherein halogen is fluorine.

5. The compound according to claim 1 wherein $R_5$ is hydrogen or methyl.

6. The compound according to claim 1 wherein at most one of $R_1$, $R_2$, $R_3$, $R_4$, $R_7$, $R_8$, $R_9$, $R_{11}$, $R_{12}$, $R_{13}$, $R_{14}$ or $R_{15}$ is other than hydrogen.

7. The compound according to claim 1 wherein $R_1$, $R_2$, $R_3$, $R_4$, $R_7$, $R_8$, $R_9$, $R_{11}$, $R_{12}$, $R_{13}$, $R_{14}$ and $R_{15}$ are hydrogen.

8. The compound according to claim 1 wherein $R_{16}$ and $R_{17}$ are independently hydrogen, halogen or lower alkyl.

9. The compound according to claim 1 wherein $R_{18}$ and $R_{19}$ are independently hydrogen, methyl, ethyl, ethenyl, ethynyl, formyl, acetyl or epoxy.

10. Compounds of the formulae:

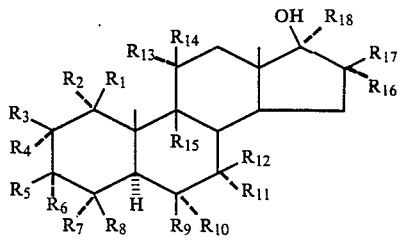

or

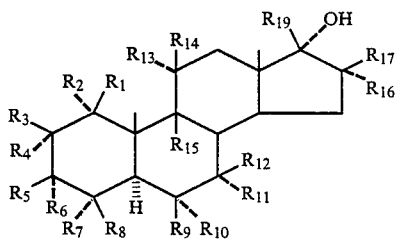

wherein
$R_1$, $R_2$, $R_3$, $R_4$, $R_7$, $R_8$, $R_{11}$, $R_{12}$, $R_{13}$, $R_{14}$ (and) $R_{15}$ and $R_{17}$ are each independently hydrogen, lower alkyl, halogen, hydroxy, or lower alkoxy; and $R_5$ and $R_6$ are independently hydrogen, lower alkyl or lower alkoxy;
$R_{16}$ is lower alkyl, halogen, or lower alkoxy;
$R_9$ and $R_{10}$ are independently hydrogen, lower alkyl or halogen; and
$R_{18}$ and $R_{19}$ are each independently hydrogen, lower alkyl, lower alkenyl, lower alkynyl, formyl, lower alkanoyl or epoxy.

11. The compound according to claim 10 wherein the lower alkyl and lower alkoxy group contain 1-3 carbon atoms.

12. The compound according to claim 10 wherein lower alkyl is methyl.

13. The compound according to claim 10 wherein halogen is fluorine.

14. The compound according to claim 10 wherein $R_5$ is hydrogen or methyl.

15. The compound according to claim 10 wherein at most one of $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ is other than hydrogen.

16. The compound according to claim 10 wherein $R_1$, $R_2$, $R_3$, $R_4$, $R_7$, $R_8$, $R_9$, $R_{10}$, $R_{11}$, $R_{12}$, $R_{13}$, $R_{14}$ and $R_{15}$ are hydrogen.

17. The compound according to claim 10 wherein $R_{16}$ and $R_{17}$ are independently hydrogen, halogen or lower alkyl.

18. The compound according to claim 10 wherein $R_{18}$ and $R_{19}$ are independently hydrogen, methyl, ethyl, ethenyl, ethynyl, formyl, acetyl or epoxy.

19. Compounds of the formulae:

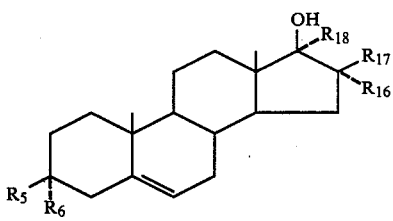

or

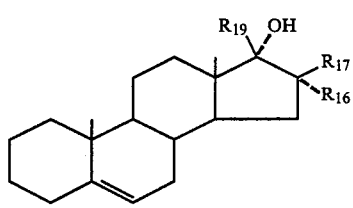

wherein $R_5$ and $R_6$ are independently hydrogen or lower alkyl;

$R_{16}$ is lower alkyl, halogen or lower alkoxy, $R_{17}$ is hydrogen, lower alkyl, halogen, or lower alkoxy; and $R_{18}$ and $R_{19}$ are each independently hydrogen, lower alkyl, lower alkenyl, lower alkynyl, formyl, lower alkanoyl or epoxy.

20. The compound according to claim 19 wherein the lower alkyl and lower alkoxy group contain 1-3 carbon atoms.

21. The compound according to claim 19 wherein lower alkyl is methyl.

22. The compound according to claim 19 wherein halogen is fluorine.

23. The compound according to claim 19 wherein $R_5$ is hydrogen or methyl.

24. The compound according to claim 19 wherein $R_{16}$ and $R_{17}$ are independently hydrogen, halogen or lower alkyl.

25. The compound according to claim 19 wherein $R_{18}$ and $R_{19}$ are independently hydrogen, methyl, ethyl, ethenyl, ethynyl, formyl, acetyl or epoxy.

26. Compounds of the formulae:

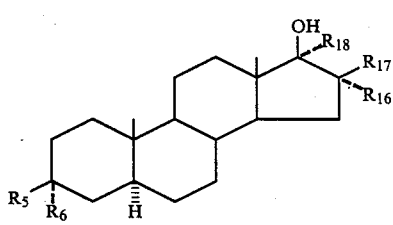

or

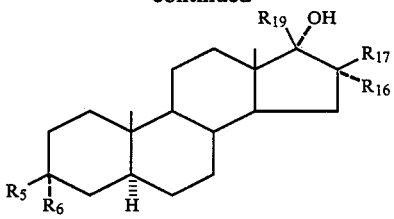

wherein $R_5$ and $R_6$ are independently hydrogen or lower alkyl;

$R_{16}$ is lower alkyl, halogen or lower alkoxy;

$R_{17}$ is hydrogen, lower alkyl, halogen, hydroxy or lower alkoxy; and $R_{18}$ and $R_{19}$ are each independently hydrogen, lower alkyl, lower alkenyl, lower alkynyl, formyl, lower alkanoyl or epoxy.

27. The compound according to claim 26 wherein the lower alkyl and lower alkoxy group contain 1-3 carbon atoms.

28. The compound according to claim 26 wherein lower alkyl is methyl.

29. The compound according to claim 26 wherein halogen is fluorine.

30. The compound according to claim 26 wherein $R_5$ is hydrogen or methyl.

31. The compound according to claim 26 wherein $R_{16}$ and $R_{17}$ are independently hydrogen, halogen or lower alkyl.

32. The compound according to claim 26 wherein $R_{18}$ and $R_{19}$ are independently hydrogen, methyl, ethyl, ethenyl, ethynyl, formyl, acetyl or epoxy.

33. The compound according to claim 19 having the formula:

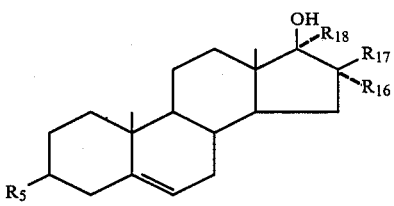

wherein $R_5$ is hydrogen or lower alkyl;

$R_{16}$ is lower alkyl, halogen, or lower alkoxy;

$R_{17}$ is hydrogen, lower alkyl, halogen, or lower alkoxy; and $R_{18}$ is hydrogen, lower alkyl, lower alkenyl, lower alkynyl, formyl, lower alkanoyl or epoxy.

34. The compound according to claim 33 wherein the lower alkyl and lower alkoxy group contain 1-3 carbon atoms.

35. The compound according to claim 33 wherein lower alkyl is methyl.

36. The compound according to claim 33 wherein halogen is fluorine.

37. The compound according to claim 33 wherein $R_5$ is hydrogen or methyl.

38. The compound according to claim 33 wherein $R_{16}$ and $R_{17}$ are independently hydrogen, halogen or lower alkyl.

39. The compound according to claim 33 wherein $R_{18}$ is independently hydrogen, methyl, ethyl, ethenyl, ethynyl, formyl, acetyl or epoxy.

40. The compound according to claim 19 having the formula:

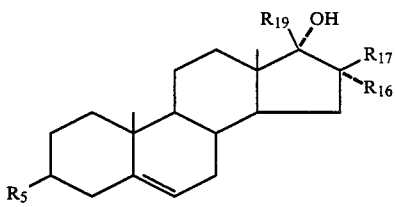

wherein $R_5$ is hydrogen or lower alkyl;
$R_{16}$ is lower alkyl, halogen or lower alkoxy;
$R_{17}$ is hydrogen, lower alkyl, halogen, or lower alkoxy; and
$R_{19}$ is hydrogen, lower alkyl, lower alkenyl, lower alkynyl, formyl lower alkanoyl or epoxy.

41. The compound according to claim 40 wherein the lower alkyl and lower alkoxy group contain 1-3 carbon atoms.

42. The compound according to claim 40 wherein lower alkyl is methyl.

43. The compound according to claim 40 wherein halogen is fluorine.

44. The compound according to claim 40 wherein $R_5$ is hydrogen or methyl.

45. The compound according to claim 40 wherein $R_{16}$ and $R_{17}$ are independently hydrogen, halogen or lower alkyl.

46. The compound according to claim 40 wherein $R_{19}$ is independently hydrogen, methyl, ethyl, ethenyl, ethynyl, formyl, acetyl or epoxy.

47. The compound according to claim 26 having the formula:

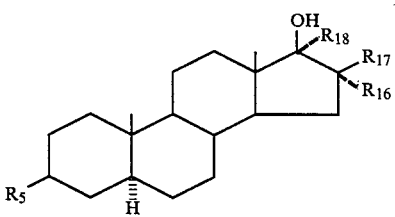

wherein
$R_5$ is hydrogen or lower alkyl;
$R_{16}$ is lower alkyl, halogen, or lower alkoxy;
$R_{17}$ is hydrogen, lower alkyl, halogen, hydroxy or lower alkoxy; and
$R_{18}$ is hydrogen, lower alkyl, lower alkenyl, lower alkynyl, formyl, lower alkanoyl or epoxy.

48. The compound according to claim 47 wherein the lower alkyl and lower alkoxy group contain 1-3 carbon atoms.

49. The compound according to claim 47 wherein lower alkyl is methyl.

50. The compound according to claim 47 wherein halogen is fluorine.

51. The compound according to claim 47 wherein $R_5$ is hydrogen or methyl.

52. The compound according to claim 47 wherein $R_{16}$ and $R_{17}$ are independently hydrogen, halogen or lower alkyl.

53. The compound according to claim 47 wherein $R_{18}$ is independently hydrogen, methyl, ethyl, ethenyl, ethynyl, formyl, acetyl or epoxy.

54. The compound according to claim 26 having the formula:

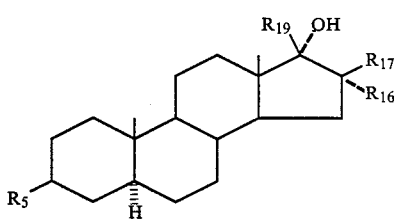

wherein
$R_5$ is hydrogen or lower alkyl;
$R_{16}$ is lower alkyl, halogen, or lower alkoxy;
$R_{17}$ is hydrogen, lower alkyl, halogen, or lower alkoxy; and
$R_{19}$ is hydrogen, lower alkyl, lower alkenyl, lower alkynyl, formyl, lower alkanoyl or epoxy.

55. The compound according to claim 54 wherein the lower alkyl and lower alkoxy group contain 1-3 carbon atoms.

56. The compound according to claim 54 wherein lower alkyl is methyl.

57. The compound according to claim 54 wherein halogen is fluorine.

58. The compound according to claim 54 wherein $R_5$ is hydrogen or methyl.

59. The compound according to claim 54 wherein $R_{16}$ and $R_{17}$ are independently hydrogen, halogen or lower alkyl.

60. The compound according to claim 54 wherein $R_{19}$ is independently hydrogen, methyl, ethyl, ethenyl, ethynyl, formyl, acetyl or epoxy.

61. The compound having the formula:

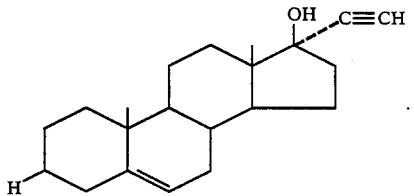

62. The compound having the formula:

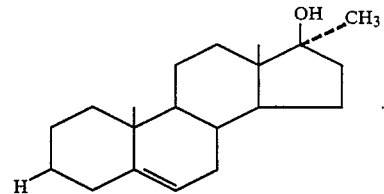

63. The compound having the formula:

64. The compound having the formula:

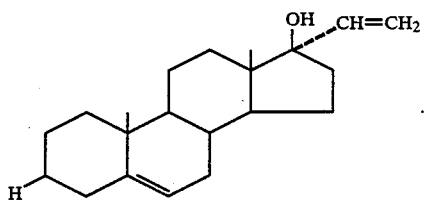

65. The compound having the formula:

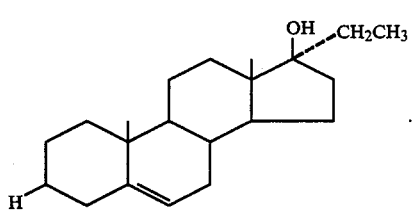

66. The compound having the formula:

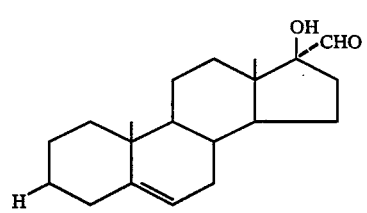

67. The compound having the formula:

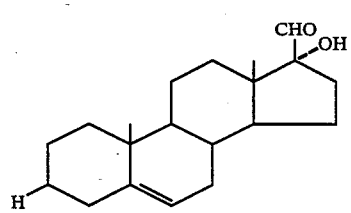

68. The compound according to claim 1 having the formula:

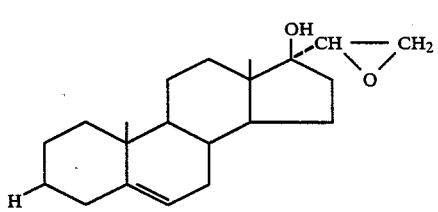

69. The compound according to claim 1 having the formula:

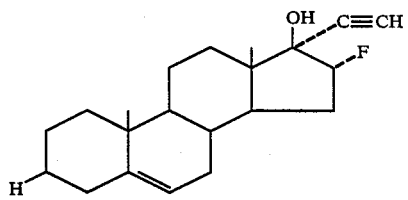

70. The compound according to claim 1 having the formula:

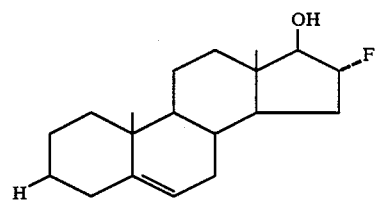

71. The compound having the formula:

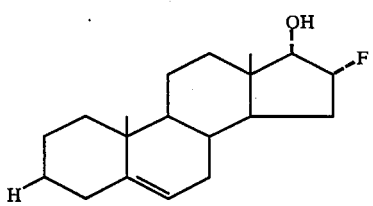

72. The compound having the formula:

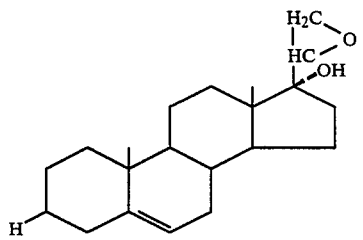

73. The compound having the formula:

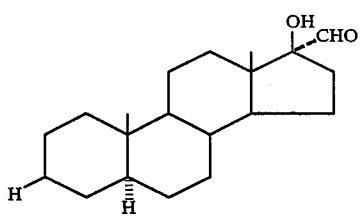

74. The compound having the formula:

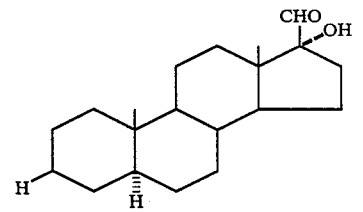

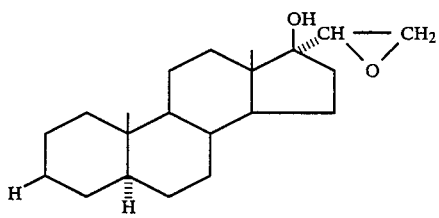

75. The compound according to claim 9 having the formula:

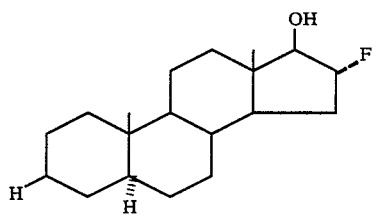

76. The compound according to claim 10 having the formula:

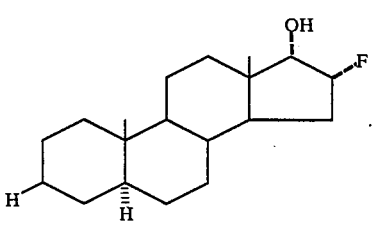

77. The compound according to claim 10 having the formula:

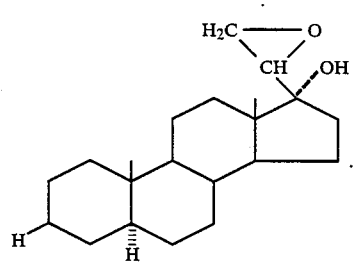

78. The compound having the formula:

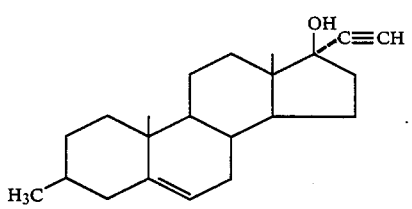

79. The compound having the formula:

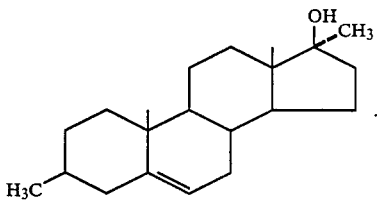

80. The compound having the formula:

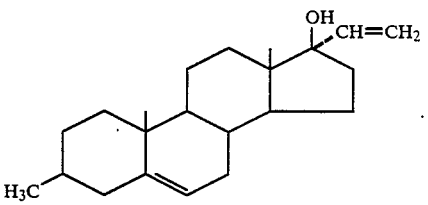

81. The compound having the formula:

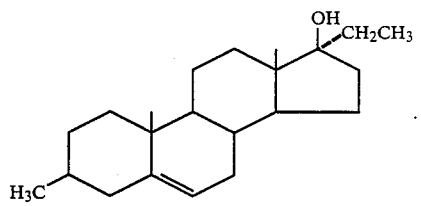

82. The compound having the formula:

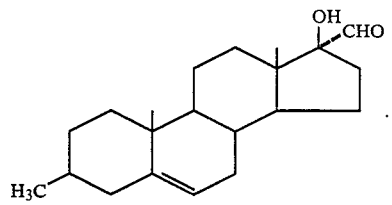

83. The compound having the formula:

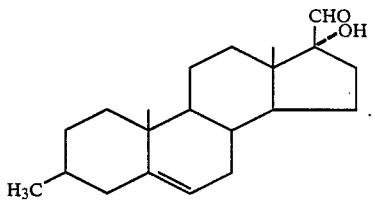

84. The compound having the formula:

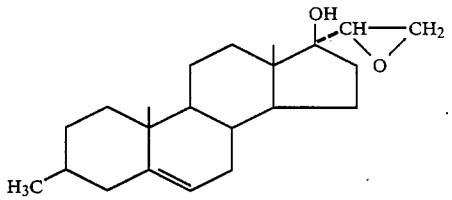

85. The compound according to claim 1 having the formula:

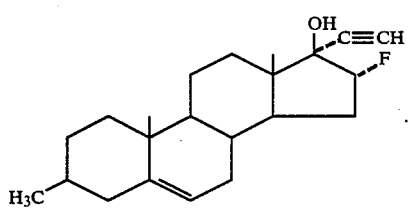

86. The compound according to claim 1 having the formula:

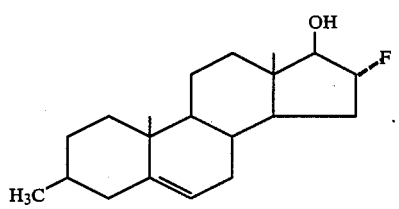

87. The compound according to claim 1 having the formula:

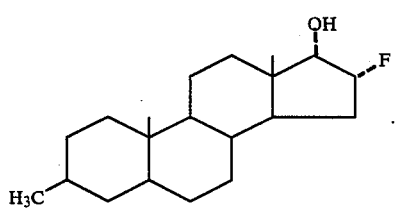

88. The compound having the formula:

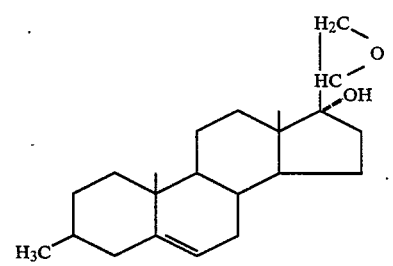

89. The compound having the formula:

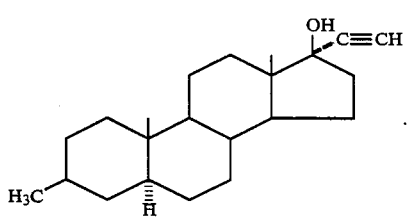

90. The compound having the formula:

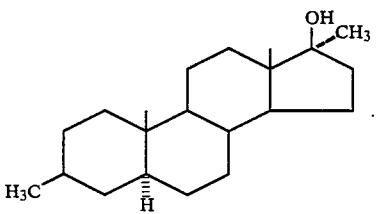

91. The compound having the formula:

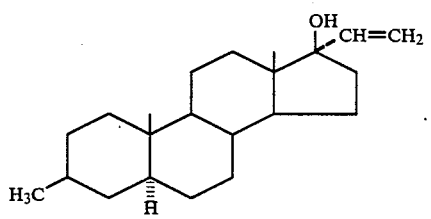

92. The compound having the formula:

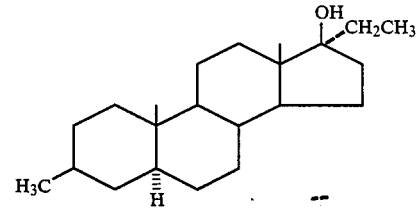

93. The compound having the formula:

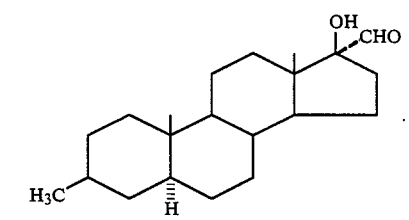

94. The compound having the formula:

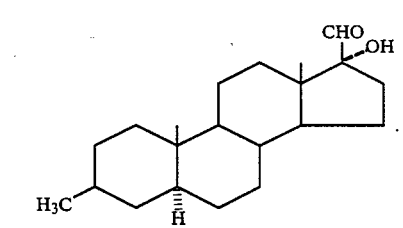

95. The compound having the formula:

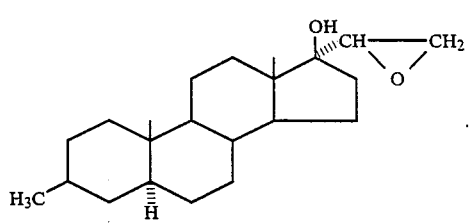

96. The compound according to claim 10 having the formula:
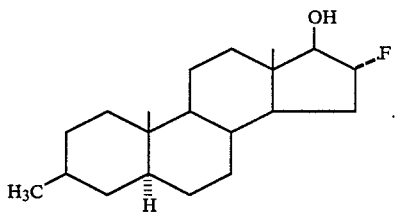
97. The compound according to claim 10 having the formula:
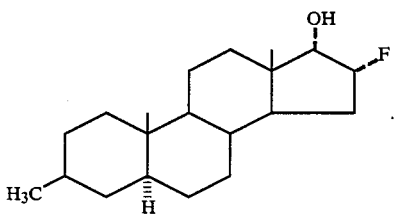
98. The compound having the formula:
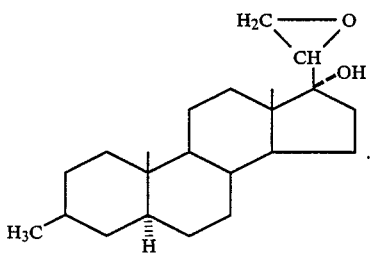
99. The compound which is:
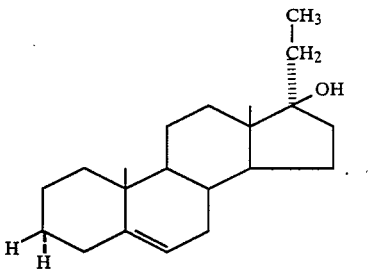
100. The compound which is:
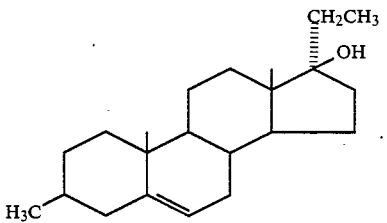
101. The compound which is:
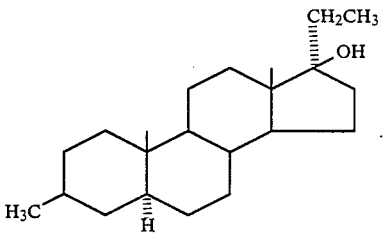
* * * * *

UNITED STATES PATENT AND TRADEMARK OFFICE
CERTIFICATE OF CORRECTION

PATENT NO. : 4,898,694

DATED : February 6, 1990

INVENTOR(S) : Arthur G. Schwartz

It is certified that error appears in the above-identified patent and that said Letters Patent is hereby corrected as shown below:

Column 30, Line 49, delete "⟶".

Column 32, Line 32, above "∥", insert --O--.

Column 33, Line 10, "O" should read as --OH--.

Column 33, Line 19, "O" should read as --OH--.

Column 34, Lines 5-20,

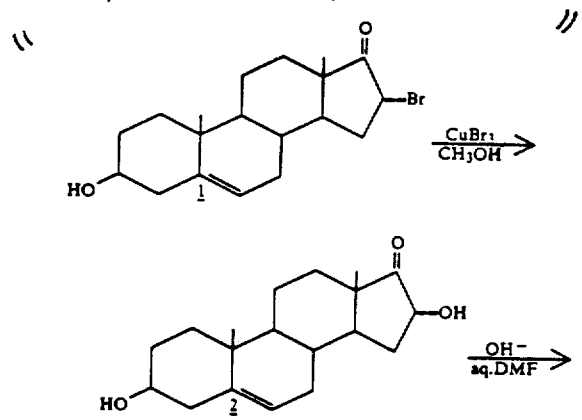

should read as

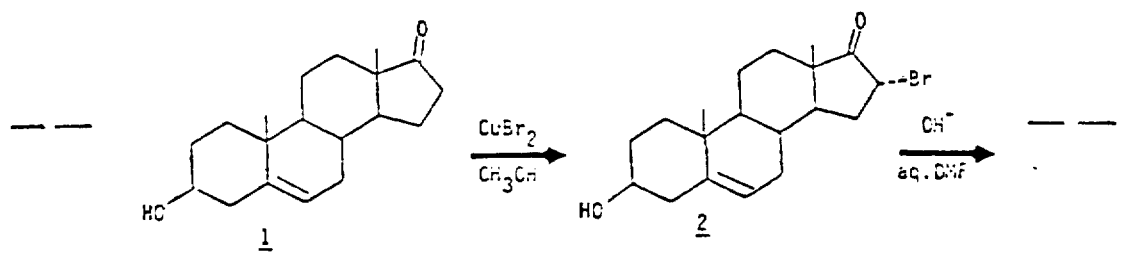

UNITED STATES PATENT AND TRADEMARK OFFICE
CERTIFICATE OF CORRECTION

PATENT NO. : 4,898,694

DATED : February 6, 1990

INVENTOR(S) : Arthur G. Schwartz

It is certified that error appears in the above-identified patent and that said Letters Patent is hereby corrected as shown below:

Column 35, Line 45,

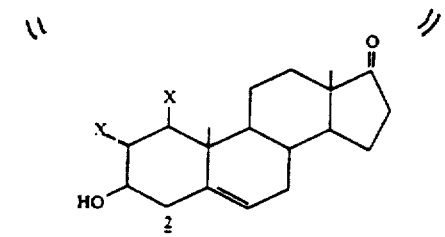

should read as

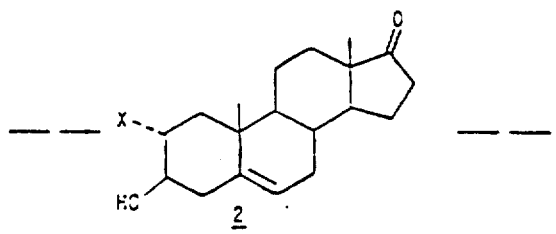

Column 35, Line 58, "Carbon-2" should read as --Carbon-3--.

Column 63, Line 2, "methly" should read as --methyl--.

Column 63, Line 34, "pint" should read as --point--.

UNITED STATES PATENT AND TRADEMARK OFFICE
CERTIFICATE OF CORRECTION

PATENT NO. : 4,898,694

DATED : February 6, 1990

INVENTOR(S) : Arthur G. Schwartz

It is certified that error appears in the above-identified patent and that said Letters Patent is hereby corrected as shown below:

Column 65, Line 44, "anrosten" should read as --androsten--.

Column 66, Line 47, "methly" should read as --methyl--.

Column 66, Line 52, "methly" should read as --methyl--.

Column 67, Line 1, "methly" should read as --methyl--.

Column 68, Line 17, "methly" should read as --methyl--.

Column 68, Line 18, "methly" should read as --methyl--.

Signed and Sealed this

First Day of December, 1992

*Attest:*

DOUGLAS B. COMER

*Attesting Officer*      *Acting Commissioner of Patents and Trademarks*